(12) United States Patent
Presta et al.

(10) Patent No.: US 7,846,443 B2
(45) Date of Patent: Dec. 7, 2010

(54) ANTIBODIES TO IL-17A

(75) Inventors: Leonard G. Presta, San Francisco, CA (US); Edward P. Bowman, Redwood City, CA (US)

(73) Assignee: Schering Corporation, Kenilworth, NJ (US)

( * ) Notice: Subject to any disclaimer, the term of this patent is extended or adjusted under 35 U.S.C. 154(b) by 457 days.

(21) Appl. No.: 11/836,318

(22) Filed: Aug. 9, 2007

(65) Prior Publication Data

US 2009/0175881 A1 Jul. 9, 2009

Related U.S. Application Data

(60) Provisional application No. 60/837,197, filed on Aug. 11, 2006.

(51) Int. Cl.
*A61K 39/395* (2006.01)
*A61K 39/44* (2006.01)
*C07K 16/24* (2006.01)
*C12N 15/63* (2006.01)

(52) U.S. Cl. ............. 424/145.1; 424/158.1; 530/387.3; 530/387.9; 530/388.23; 530/389.2; 435/69.6; 435/320.1; 435/325; 536/23.53

(58) Field of Classification Search ........................ None
See application file for complete search history.

(56) References Cited

U.S. PATENT DOCUMENTS

| 6,274,711 B1 | 8/2001 | Golstein et al. |
|---|---|---|
| 2003/0166862 A1 | 9/2003 | Golstein et al. |

FOREIGN PATENT DOCUMENTS

| WO | WO2004/071517 | 8/2004 |
|---|---|---|
| WO | WO2004/106377 | 12/2004 |
| WO | WO2005/051422 | 6/2005 |
| WO | WO2005/108616 | 11/2005 |
| WO | WO2006/013107 | 2/2006 |
| WO | WO2006/054059 | 5/2006 |
| WO | WO2007/070750 | 6/2007 |
| WO | WO2007/106769 | 9/2007 |
| WO | WO2007/147019 | 12/2007 |
| WO | WO2007/149032 | 12/2007 |
| WO | WO2008/001063 | 1/2008 |

OTHER PUBLICATIONS

Lederman et al. Mol Immunol 28: 1171-1181, 1991.*
Li et al. Proc Natl Acad Sci USA 77: 3211-3214, 1980.*
Prosci Inc., Anti-Human IL-17, Catalog No. XP-5171, Apr. 2004.*
Prosci Inc., Anti-Human IL-17, Catalog No. XP-5172, Apr. 2004.*
Prosci Inc., Anti-Human IL-17, Catalog No. XW-7289, Jul. 2004.*
Chabaud, Martine et al., "Contribution of Interleukin 17 to Synovium Matrix Destruction in Rheumatoid Arthritis", *Cytokine* 12 (7):1092-1099 (2000).
Epitomics, IL-17 Rabbit Monoclonal Antibody, Epitomics Catalog No. 1656-1.
Gorman, Scott D., et al.; "Reshaping a Therapeutic CD4 Antibody"; *Proc. Natl. Acad. Sci. USA*; 88:4181-4185 (1991).
Hodgson, John.; "Making Monoclonals in Microbes"; *Nature Biotechnology* (NY); 9:421-425 (1991).
Jones, Peter T., et al.; "Replacing the Complementarity-determining regions in a human antibody with those from a mouse"; *Nature*; 321(29):522-525 (1986).
Kabat, Elvin A., et al.; "Identical V Region Amino Acid Sequences and Segments of Sequences in Antibodies of Different Specificities"; *The Journal of Immunology*; 147(5):1709-1719 (1991).
Koenders, Marije, I.; et al., "Interleukin-17 Acts Independently of TNF-α under Arthritic Conditions[1]"; *The Journal of Immunology*; 176:6262-6269 (2006).
Langrish, Claire L.; et al.; "IL-23 drives a pathogenic T cell population that induces autoimmune inflammation"; *The Journal of Experimental Medicine*; 201(2):233-240 (2005).
Liu, Alvin Y., et al; "Chimeric mouse-human IgG1 antibody that can mediate lysis of cancer cells"; *Proc. Natl. Acad. Sci. USA*; 84:3439-3443 (1987).
Mackay, Ian R., et al.; "T-Cell Function and Migration"; *The New England Journal of Medicine*; 343(14):1020-1034 (2000).
Mackay, Ian R.; et al.; "Autoimmune Diseases"; *The New England Journal of Medicine*; 345(5):340-350 (2001).
McKenzie, Brent S.; et al.; "Understanding the IL-23-1L-17 immune pathway"; *Trends in Immunology*; 27(1):17-23 (2006).
Queen, Cary, et al.; "A humanized antibody that binds to the interleukin 2 receptor"; *Proc. Natl. Acad. Sci. USA*; 86:10029-10033 (1989).
R&D Systems, Monoclonal Anti-Human IL-17 Antibody, R&D Systems Catalog No. MAB3171, Clone 41802 (2004).
R&D Systems, Monoclonal Anti-Human IL-17 Antibody, R&D Systems Catalog No. MAB317, Clone 41809 (2006).
Verhoeyen, Martine, et al.; "Reshaping Human Antibodies: Grafting an Antilysozyme Activity"; *Science*; 239:1534-1536 (1988).
International Search Report for corresponding International Application No. PCT/US2007/017679 dated May 20, 2008.
Product Information; Functional Grade Purified anti-human IL-17A (Interleukin-17A); eBioscience (2006).

* cited by examiner

*Primary Examiner*—Bridget E Bunner
*Assistant Examiner*—Fozia M Hamud

(57) ABSTRACT

Engineered antibodies to human IL-17A are provided, as well as uses thereof.

19 Claims, 11 Drawing Sheets

```
                                      ------CDRL1------
            1         10        20        30abcdef
rat  16C10  DIVMTQSPSSLAVSIGETVTLNC   KSSQSLLFSENQKNYLA
hum  16C10  DIVMTQSPLSLPVTPGEPASISC   KSSQSLLFSENQKNYLA
rat  4C3    DIVMTQSPSSLAVSVGETVTLNC   KSSQSLLFSENQKNYLA
hum  4C3    DIVMTQSPLSLPVTPGEPASISC   KSSQSLLFSENQKNYLA
rat  23E12  DIQMTQSPASLSASLGETVTIQC   QASEDI-YSG-----LA
rat  30C10  DIVMTQSPSSLAVSPGETVTINC   KSSQSLFWSESHMNYLA
hum  30C10  DIVMTQSPLSLPVTPGEPASISC   KSSQSLFWSESHMNYLA
rat  12E6   DIQMTQSPSSLSASLGDRVTITC   RTSQDI------GNYLS
rat  1D10   DIQMTQSPSFLSASVGERVTLSC   KASQNI------NKYLD -CDRL2-
            40        50        60        70        80
rat  16C10  WYQHKSGQSPKLLVY   WTSTRQS   GVPDRFMGSGSTDFTLTISSVQA
hum  16C10  WYLQKPGQSPQLLIY   WTSTRQS   GVPDRFSGSGSGTDFTLKISRVEA
rat  4C3    WYQHKSGQSPKLLVY   WTSTRQS   GVPDRFMGSGSTDFTLTISSVQA
hum  4C3    WYLQKPGQSPQLLIY   WTSTRQS   GVPDRFSGSGSGTDFTLKISRVEA
rat  23E12  WYHQKPGKSPQLLIL   GASRLHD   GVPSRFSGSGSGIEYSLKINNMQT
rat  30C10  WYQQKPGQSPKLLIY   YASTRQS   GVPDRFIGSGSGTDFTLTISGVQA
hum  30C10  WYLQKPGQSPQLLIY   YASTRQS   GVPDRFSGSGSGTDFTLKISRVEA
rat  12E6   WFQQKPGKSPRLMIY   GASNLED   GVPSRFSGSRSGSDYSLTISSLES
rat  1D10   WFQQKLGEAPKLLIY   NADNLHT   GIPSRFSGSGSFSDFILTISSLQP --CDRL3--
                 90        100
rat  16C10  EDLAIYYC   QQSYYTPYT   FGAGTKLELKR
hum  16C10  EDVGVYYC   QQSYYTPYT   FGQGTKVEIKR
rat  4C3    EDLAIYYC   QQSYYTPYT   FGAGTKLELKR
hum  4C3    EDVGVYYC   QQSYYTPYT   FGQGTKVEIKR
rat  23E12  EDEGIYFC   QQGLKYPPT   FGGGTKLELKR
rat  30C10  EDLAVYYC   HHHYDS-HT   FGAGTKLELKR
hum  30C10  EDVGVYYC   HHHYDS-HT   FGQGTKVEIKR
rat  12E6   EDTAIYYC   LQYDKYPNT   FGAGTKLELKR
rat  1D10   EDDATYFC   LQRESWPYT   FGAGTKLELKR
```

Figure 1A

```
                                    ---CDRH1--
            1         10         20         30         40
rat  16C10  QVELRESGPGLVQPSQTLSLTCTVS  GFSLPSHSVS  WIRQPPGKGLEWMG
hum  16C10  QVQLQESGPGLVKPSETLSLTCTVS  GFSLPSHSVS  WIRQPPGKGLEWIG
rat  4C3    QVELRESGPGLVQPSQTLSLTCTVS  GFSLPSHSVS  WIRQPPGKGLEWMG
hum  4C3    QVQLQESGPGLVKPSETLSLTCTVS  GFSLPSHSVS  WIRQPPGKGLEWIG
rat  23E12  QVQLKESGPGLVQPSQTLSLTCTVF  GFSLTNNGVT  WVRQPPGKGLEWIA
rat  30C10  EVQLVESGGGLVQPGRSQKLSCVVS  GFTFNNYWMT  WIRQAPGKGLEWVA
hum  30C10  QVQLVESGGGVVQPGRSLRLSCAAS  GFTFNNYWMT  WVRQAPGKGLEWVA
rat  12E6   EVQLEESGGGLVQPGRSLKLSCAAS  GFTFRDYYMV  WVRQAPKKGLEWVA
rat  1D10   QVQLKESGPGLVQPSQTLSLTCTVS  GFSLTNYYVH  WVRQPPGKGLEWMG ------CDRH2------
            50    a         60         70         80     abc      90
rat  16C10  IIW-NNGGTDYNSAFKS  RLTISRDTSKSQVFLKMNSLQTEDTAMYFCAR
hum  16C10  IIW-NQGGTDYNSAFKS  RVTISVDTSKNQFSLKLSSVTAADTAVYYCAR
rat  4C3    IIW-NNGGTDYNSAFKS  RLTISRDTSKSQVFLKMNSLQTEDTAMYFCAR
hum  4C3    IIW-NQGGTDYNSAFKS  RVTISVDTSKNQFSLKLSSVTAADTAVYYCAR
rat  23E12  EVS-SGGSTDYNSALKS  RLSISRDTSKSQVFLRMNSLQTEDTAIYFCAR
rat  30C10  SVSNTGSSTYYPASVKG  RFTISRDNAKSTLYLQMNSLRSEDTATYYCTR
hum  30C10  SVSNTGSSTYYPASVKG  RFTISRDNSKNTLYLQMNSLRAEDTAVYYCAR
rat  12E6   SISYEGSSIYYGESVKG  RFTISRDNAKSTLYLQMNSLRSEDTATYYCAR
rat  1D10   GVW-NDGDTSYNSVLRS  RLSITRDTSKSQVLLKMSSLQTEDTATYYCAR -----CDRH3------
                    abcdefgh       110
rat  16C10  NMYITDYYYENYFMDA  WGQGASVTVSS
hum  16C10  NAYITDYYYENYFMDA  WGQGTLVTVSS
rat  4C3    NMYITDYYYENYFMDA  WGQGASVTVSS
hum  4C3    NAYITDYYYENYFMDA  WGQGTLVTVSS
rat  23E12  QEVFTGL-------LDY  WGQGVMVTVSS
rat  30C10  EGAYY---------LDY  WGQGVMVTVSS
hum  30C10  EGAYY---------LDY  WGQGTLVTVSS
rat  12E6   HGFNP---------FDY  WGRGVMVTVSS
rat  1D10   EGREGFVGYYV--MDA   WGPGASVTVSS
```

Figure 1B

```
                          ------CDRL1------
H₂N-DIVMTQSPLSLPVTPGEPASISC KSSQSLLFSENQKNYLA WYLQKPGQSPQLLIY

-CDRL2-                                       --CDRL3--
WTSTRQS GVPDRFSGSGSGTDFTLKISRVEAEDVGVYYC QQSYYTPYT

FGQGTKVEIKR
``` human kappa constant light domain
TVAAPSVFIFPPSDEQLKSGTASVVCLLNNFYPREAKVQWKVDNALQSGNSQESVTEQ
DSKDSTYSLSSTLTLSKADYEKHKVYACEVTHQGLSSPVTKSFNRGEC-COOH

Figure 2A

```
                           ---CDRH1--
H₂N-QVQLQESGPGLVKPSETLSLTCTVS GFSLPSHSVS WIRQPPGKGLEWIG

-----CDRH2------
IIWNQGGTDYNSAFKS RVTISVDTSKNQFSLKLSSVTAADTAVYYCAR

------CDRH3-----
NAYITDYYYENYFMDA WGQGTLVTVSS human IgG1 Fc (CH1-hinge-CH2-CH3)

ASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPE
LLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVY
TLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK-COOH
```

Figure 2B

```
  1  ATG GCC CCC GTG CAG CTG CTG GGC CTG CTG GTG CTG TTC CTG CCC GCC ATG
 52  AGA TGC GAC ATC GTG ATG ACC CAG AGC CCC CTG AGC CTG CCC GTG ACC CCA
103  GGC GAG CCC GCC AGC ATC AGC TGC AAG AGC AGC CAG AGC CTG CTG TTC AGC
154  GAG AAC CAG AAG AAC TAC CTG GCC TGG TAT CTG CAG AAG CCC GGC CAG TCC
205  CCC CAG CTG CTG ATC TAC TGG ACC AGC ACC AGG CAG AGC GGC GTG CCC GAC
256  AGG TTC AGC GGC AGC GGC TCC GGC ACC GAC TTC ACC CTG AAG ATC AGC AGG
307  GTG GAG GCC GAG GAC GTG GGC GTG TAC TAC TGC CAG CAG AGC TAC TAC ACC
358  CCC TAC ACC TTC GGC CAG GGC ACC AAG GTG GAG ATC AAG CGT ACG GTG GCT
409  GCC CCC AGC GTG TTC ATC TTC CCC CCC AGC GAC GAG CAG CTG AAG AGC GGC
460  ACC GCC AGC GTG GTG TGC CTG CTG AAC AAC TTC TAC CCC CGG GAG GCC AAG
511  GTG CAG TGG AAG GTG GAC AAC GCC CTG CAG AGC GGC AAC AGC CAG GAA AGC
562  GTC ACC GAG CAG GAC AGC AAG GAC TCC ACC TAC AGC CTG AGC AGC ACC CTG
613  ACC CTG AGC AAG GCC GAC TAC GAG AAG CAC AAG GTG TAC GCC TGC GAG GTG
664  ACC CAC CAG GGC CTG TCC AGC CCC GTG ACC AAG AGC TTC AAC AGG GGC GAG
715  TGC TAG
```

Figure 5A

```
1    ATG GCC GTG CTG GGC CTG CTG TTC TGC CTG GTG ACC TTC CCC AGC TGC GTG
52   CTG TCC CAG GTG CAG CTG CAG GAA AGC GGC CCA GGC CTG GTG AAG CCC AGC
103  GAG ACC CTG AGC CTG ACC TGC ACC GTG AGC GGC TTC AGC CTG CCC AGC CAC
154  AGC GTG AGC TGG ATC AGG CAG CCC CCA GGC AAG GGC CTG GAA TGG ATC GGC
205  ATC ATC TGG AAC CAG GGC GGC ACC GAC TAC AAC AGC GCC TTC AAG AGC AGG
256  GTG ACC ATC AGC GTG GAC ACC AGC AAG AAC CAG TTC AGC CTG AAG CTG TCC
307  AGC GTG ACA GCC GCC GAC ACC GCC GTG TAC TAC TGC GCC AGG AAC GCC TAC
358  ATC ACC GAC TAC TAC TAC GAG AAC TAC TTC ATG GAC GCC TGG GGC CAG GGC
409  ACC CTG GTG ACC GTG AGC AGC GCT AGC ACC AAG GGC CCA AGC GTG TTC CCC
460  CTG GCC CCC AGC AGC AAG AGC ACC TCC GGC GGC ACA GCC GCC CTG GGC TGT
511  CTG GTG AAG GAC TAC TTC CCC GAG CCC GTG ACC GTG TCC TGG AAC AGC GGA
562  GCC CTG ACC AGC GGC GTG CAC ACC TTC CCC GCC GTG CTG CAG AGC AGC GGC
613  CTG TAC AGC CTG AGC AGC GTG GTG ACA GTG CCC AGC AGC AGC CTG GGC ACC
664  CAG ACC TAC ATC TGC AAC GTG AAC CAC AAG CCC AGC AAC ACC AAG GTG GAC
715  AAG AAG GTG GAG CCC AAG AGC TGC GAC AAG ACC CAC ACC TGC CCC CCC TGC
766  CCT GCC CCA GAG CTG CTG GGC GGA CCC AGC GTG TTC CTG TTC CCC CCC AAG
817  CCC AAG GAC ACC CTG ATG ATC AGC AGG ACC CCC GAG GTG ACC TGC GTG GTG
868  GTG GAC GTG AGC CAC GAG GAC CCA GAG GTG AAG TTC AAC TGG TAC GTG GAC
919  GGC GTG GAG GTG CAC AAC GCC AAG ACC AAG CCC AGA GAG GAA CAG TAC AAC
970  AGC ACC TAC AGG GTG GTG TCC GTG CTG ACC GTG CTG CAC CAG GAC TGG CTG
1021 AAC GGC AAG GAG TAC AAG TGC AAG GTC TCC AAC AAG GCC CTG CCA GCC CCC
1072 ATC GAG AAA ACC ATC AGC AAG GCC AAG GGC CAG CCA CGG GAG CCC CAG GTG
1123 TAC ACC CTG CCC CCC AGC CGG GAC GAG CTG ACC AAG AAC CAG GTG TCC CTG
1174 ACC TGC CTG GTG AAG GGC TTC TAC CCC AGC GAC ATC GCC GTG GAG TGG GAG
1225 AGC AAC GGC CAG CCC GAG AAC AAC TAC AAG ACC ACC CCC CCA GTG CTG GAC
1276 AGC GAC GGC AGC TTC TTC CTG TAC AGC AAG CTG ACC GTG GAC AAG AGC AGG
1327 TGG CAG CAG GGC AAC GTG TTC AGC TGC AGC GTG ATG CAC GAG GCC CTG CAC
1378 AAC CAC TAC ACC CAG AAG AGC CTG AGC CTG TCC CCC GGC AAG TGA
```

Figure 5B

SEQUENCE LISTING

```
<160> NUMBER OF SEQ ID NOS: 65

<210> SEQ ID NO 1
<211> LENGTH: 720
<212> TYPE: DNA
<213> ORGANISM: Artificial
<220> FEATURE:
<223> OTHER INFORMATION: Humanized 16C10 Antibody Light Chain with
      Signal Sequence
<220> FEATURE:
<221> NAME/KEY: CDS
<222> LOCATION: (1)..(717)
<220> FEATURE:
<221> NAME/KEY: sig_peptide
<222> LOCATION: (1)..(57)
<220> FEATURE:
<221> NAME/KEY: mat_peptide
<222> LOCATION: (58)..(717)

<400> SEQUENCE: 1 atg gct cca gtg cag ctg ctg ggg ctg ctg gtg ctg ttc ctg cca gcc      48
Met Ala Pro Val Gln Leu Leu Gly Leu Leu Val Leu Phe Leu Pro Ala
            -15                 -10                  -5 atg aga tgt gat atc gtg atg acc cag tct cca ctg tcc ctg cct gtg      96
Met Arg Cys Asp Ile Val Met Thr Gln Ser Pro Leu Ser Leu Pro Val
        -1   1               5                  10 aca ccc gga gag cca gcc agc atc agc tgc aag agc agc cag agc ctg     144
Thr Pro Gly Glu Pro Ala Ser Ile Ser Cys Lys Ser Ser Gln Ser Leu
     15                  20                  25 ctg ttc agc gag aac cag aag aac tac ctg gcc tgg tat ctg cag aaa     192
```

```
Leu Phe Ser Glu Asn Gln Lys Asn Tyr Leu Ala Trp Tyr Leu Gln Lys
 30                  35                  40                  45 cca ggg cag agc cct cag ctg ctg atc tat tgg acc agc acc cgg cag      240
Pro Gly Gln Ser Pro Gln Leu Leu Ile Tyr Trp Thr Ser Thr Arg Gln
                 50                  55                  60 agc ggg gtg cca gac agg ttc agc ggc agc gga tct ggg aca gat ttc      288
Ser Gly Val Pro Asp Arg Phe Ser Gly Ser Gly Ser Gly Thr Asp Phe
                 65                  70                  75 act ctg aag atc agc cgg gtg gag gcc gaa gat gtg ggc gtg tac tac      336
Thr Leu Lys Ile Ser Arg Val Glu Ala Glu Asp Val Gly Val Tyr Tyr
             80                  85                  90 tgt cag cag agc tat tac aca ccc tac acc ttt gga cag ggg acc aag      384
Cys Gln Gln Ser Tyr Tyr Thr Pro Tyr Thr Phe Gly Gln Gly Thr Lys
             95                 100                 105 gtg gaa atc aaa cgt acg gtg gct gca cca tct gtc ttc atc ttc ccg      432
Val Glu Ile Lys Arg Thr Val Ala Ala Pro Ser Val Phe Ile Phe Pro
110                 115                 120                 125 cca tct gat gag cag ttg aaa tct gga act gcc tct gtt gtg tgc ctg      480
Pro Ser Asp Glu Gln Leu Lys Ser Gly Thr Ala Ser Val Val Cys Leu
                130                 135                 140 ctg aat aac ttc tat ccc aga gag gcc aaa gta cag tgg aag gtg gat      528
Leu Asn Asn Phe Tyr Pro Arg Glu Ala Lys Val Gln Trp Lys Val Asp
                145                 150                 155 aac gcc ctc caa tcg ggt aac tcc cag gag agt gtc aca gag cag gac      576
Asn Ala Leu Gln Ser Gly Asn Ser Gln Glu Ser Val Thr Glu Gln Asp
            160                 165                 170 agc aag gac agc acc tac agc ctc agc agc acc ctg acg ctg agc aaa      624
Ser Lys Asp Ser Thr Tyr Ser Leu Ser Ser Thr Leu Thr Leu Ser Lys
175                 180                 185 gca gac tac gag aaa cac aaa gtc tac gcc tgc gaa gtc acc cat cag      672
Ala Asp Tyr Glu Lys His Lys Val Tyr Ala Cys Glu Val Thr His Gln
190                 195                 200                 205 ggc ctg agc tcg ccc gtc aca aag agc ttc aac agg gga gag tgt taa      720
Gly Leu Ser Ser Pro Val Thr Lys Ser Phe Asn Arg Gly Glu Cys
                210                 215                 220

<210> SEQ ID NO 2
<211> LENGTH: 239
<212> TYPE: PRT
<213> ORGANISM: Artificial
<220> FEATURE:
<223> OTHER INFORMATION: Synthetic Construct

<400> SEQUENCE: 2

Met Ala Pro Val Gln Leu Leu Gly Leu Leu Val Leu Phe Leu Pro Ala
                -15                 -10                  -5

Met Arg Cys Asp Ile Val Met Thr Gln Ser Pro Leu Ser Leu Pro Val
         -1   1               5                  10

Thr Pro Gly Glu Pro Ala Ser Ile Ser Cys Lys Ser Gln Ser Leu
 15                  20                  25

Leu Phe Ser Glu Asn Gln Lys Asn Tyr Leu Ala Trp Tyr Leu Gln Lys
 30                  35                  40                  45

Pro Gly Gln Ser Pro Gln Leu Leu Ile Tyr Trp Thr Ser Thr Arg Gln
                 50                  55                  60

Ser Gly Val Pro Asp Arg Phe Ser Gly Ser Gly Ser Gly Thr Asp Phe
                 65                  70                  75

Thr Leu Lys Ile Ser Arg Val Glu Ala Glu Asp Val Gly Val Tyr Tyr
             80                  85                  90

Cys Gln Gln Ser Tyr Tyr Thr Pro Tyr Thr Phe Gly Gln Gly Thr Lys
```

```
                     95                  100                 105
Val Glu Ile Lys Arg Thr Val Ala Ala Pro Ser Val Phe Ile Phe Pro
110                 115                 120                 125

Pro Ser Asp Glu Gln Leu Lys Ser Gly Thr Ala Ser Val Val Cys Leu
                    130                 135                 140

Leu Asn Asn Phe Tyr Pro Arg Glu Ala Lys Val Gln Trp Lys Val Asp
                145                 150                 155

Asn Ala Leu Gln Ser Gly Asn Ser Gln Glu Ser Val Thr Glu Gln Asp
            160                 165                 170

Ser Lys Asp Ser Thr Tyr Ser Leu Ser Ser Thr Leu Thr Leu Ser Lys
        175                 180                 185

Ala Asp Tyr Glu Lys His Lys Val Tyr Ala Cys Glu Val Thr His Gln
190                 195                 200                 205

Gly Leu Ser Ser Pro Val Thr Lys Ser Phe Asn Arg Gly Glu Cys
                    210                 215                 220

<210> SEQ ID NO 3
<211> LENGTH: 1422
<212> TYPE: DNA
<213> ORGANISM: Artificial
<220> FEATURE:
<223> OTHER INFORMATION: Humanized 16C10 Antibody Heavy Chain with
      Signal Sequence
<220> FEATURE:
<221> NAME/KEY: CDS
<222> LOCATION: (1)..(1419)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1419)

<400> SEQUENCE: 3 atg gct gtg ctg ggg ctg ctg ttc tgc ctg gtg aca ttc cca agc tgt      48
Met Ala Val Leu Gly Leu Leu Phe Cys Leu Val Thr Phe Pro Ser Cys
                -15                 -10                  -5 gtg ctg tcc cag gtg cag ctg cag gag tct gga cca ggc ctg gtg aag      96
Val Leu Ser Gln Val Gln Leu Gln Glu Ser Gly Pro Gly Leu Val Lys
 -1   1               5                  10 cct agc gag acc ctg agc ctg acc tgt acc gtg tct gga ttc agc ctg     144
Pro Ser Glu Thr Leu Ser Leu Thr Cys Thr Val Ser Gly Phe Ser Leu
         15                  20                  25 ccc agc cac agc gtg agc tgg atc aga cag cct cca ggc aag gga ctg     192
Pro Ser His Ser Val Ser Trp Ile Arg Gln Pro Pro Gly Lys Gly Leu
 30                  35                  40                  45 gag tgg atc ggc atc att tgg aat caa ggc ggc act gac tat aac agc     240
Glu Trp Ile Gly Ile Ile Trp Asn Gln Gly Gly Thr Asp Tyr Asn Ser
                 50                  55                  60 gcc ttc aag agc cgc gtg acc atc tcc gtg gac acc tcc aag aac cag     288
Ala Phe Lys Ser Arg Val Thr Ile Ser Val Asp Thr Ser Lys Asn Gln
             65                  70                  75 ttc agc ctg aag ctg agc agc gtg acc gct gcc gac acc gct gtg tat     336
Phe Ser Leu Lys Leu Ser Ser Val Thr Ala Ala Asp Thr Ala Val Tyr
         80                  85                  90 tac tgt gcc aga aat gca tac atc acc gac tac tat gag aac tac         384
Tyr Cys Ala Arg Asn Ala Tyr Ile Thr Asp Tyr Tyr Glu Asn Tyr
     95                 100                 105 ttc atg gat gcc tgg gga cag ggc acc ctg gtg acc gtg agc tcc gct     432
Phe Met Asp Ala Trp Gly Gln Gly Thr Leu Val Thr Val Ser Ser Ala
110                 115                 120                 125
```

```
agc acc aag ggc cca tcg gtc ttc ccc ctg gca ccc tcc tcc aag agc      480
Ser Thr Lys Gly Pro Ser Val Phe Pro Leu Ala Pro Ser Ser Lys Ser
            130                 135                 140 acc tct ggg ggc aca gcg gcc ctg ggc tgc ctg gtc aag gac tac ttc      528
Thr Ser Gly Gly Thr Ala Ala Leu Gly Cys Leu Val Lys Asp Tyr Phe
145                 150                 155 ccc gaa ccg gtg acg gtg tcg tgg aac tca ggc gcc ctg acc agc ggc      576
Pro Glu Pro Val Thr Val Ser Trp Asn Ser Gly Ala Leu Thr Ser Gly
            160                 165                 170 gtg cac acc ttc ccg gct gtc cta cag tcc tca gga ctc tac tcc ctc      624
Val His Thr Phe Pro Ala Val Leu Gln Ser Ser Gly Leu Tyr Ser Leu
175                 180                 185 agc agc gtg gtg acc gtg ccc tcc agc agc ttg ggc acc cag acc tac      672
Ser Ser Val Val Thr Val Pro Ser Ser Ser Leu Gly Thr Gln Thr Tyr
190                 195                 200                 205 atc tgc aac gtg aat cac aag ccc agc aac acc aag gtg gac aag aaa      720
Ile Cys Asn Val Asn His Lys Pro Ser Asn Thr Lys Val Asp Lys Lys
            210                 215                 220 gtt gag ccc aaa tct tgt gac aaa act cac aca tgc cca ccg tgc cca      768
Val Glu Pro Lys Ser Cys Asp Lys Thr His Thr Cys Pro Pro Cys Pro
                225                 230                 235 gca cct gaa ctc ctg ggg gga ccg tca gtc ttc ctc ttc ccc cca aaa      816
Ala Pro Glu Leu Leu Gly Gly Pro Ser Val Phe Leu Phe Pro Pro Lys
240                 245                 250 ccc aag gac acc ctc atg atc tcc cgg acc cct gag gtc aca tgc gtg      864
Pro Lys Asp Thr Leu Met Ile Ser Arg Thr Pro Glu Val Thr Cys Val
            255                 260                 265 gtg gtg gac gtg agc cac gaa gac cct gag gtc aag ttc aac tgg tac      912
Val Val Asp Val Ser His Glu Asp Pro Glu Val Lys Phe Asn Trp Tyr
270                 275                 280                 285 gtg gac ggc gtg gag gtg cat aat gcc aag aca aag ccg cgg gag gag      960
Val Asp Gly Val Glu Val His Asn Ala Lys Thr Lys Pro Arg Glu Glu
                290                 295                 300 cag tac aac agc acg tac cgt gtg gtc agc gtc ctc acc gtc ctg cac     1008
Gln Tyr Asn Ser Thr Tyr Arg Val Val Ser Val Leu Thr Val Leu His
            305                 310                 315 cag gac tgg ctg aat ggc aag gag tac aag tgc aag gtc tcc aac aaa     1056
Gln Asp Trp Leu Asn Gly Lys Glu Tyr Lys Cys Lys Val Ser Asn Lys
                320                 325                 330 gcc ctc cca gcc ccc atc gag aaa acc atc tcc aaa gcc aaa ggg cag     1104
Ala Leu Pro Ala Pro Ile Glu Lys Thr Ile Ser Lys Ala Lys Gly Gln
335                 340                 345 ccc cga gaa cca cag gtg tac acc ctg ccc cca tcc cgg gat gag ctg     1152
Pro Arg Glu Pro Gln Val Tyr Thr Leu Pro Pro Ser Arg Asp Glu Leu
350                 355                 360                 365 acc aag aac cag gtc agc ctg acc tgc ctg gtc aaa ggc ttc tat ccc     1200
Thr Lys Asn Gln Val Ser Leu Thr Cys Leu Val Lys Gly Phe Tyr Pro
            370                 375                 380 agc gac atc gcc gtg gag tgg gag agc aat ggg cag ccg gag aac aac     1248
Ser Asp Ile Ala Val Glu Trp Glu Ser Asn Gly Gln Pro Glu Asn Asn
                385                 390                 395 tac aag acc acg cct ccc gtg ctg gac tcc gac ggc tcc ttc ttc ctc     1296
Tyr Lys Thr Thr Pro Pro Val Leu Asp Ser Asp Gly Ser Phe Phe Leu
            400                 405                 410 tac agc aag ctc acc gtg gac aag agc agg tgg cag cag ggg aac gtc     1344
Tyr Ser Lys Leu Thr Val Asp Lys Ser Arg Trp Gln Gln Gly Asn Val
415                 420                 425 ttc tca tgc tcc gtg atg cat gag gct ctg cac aac cac tac acg cag     1392
Phe Ser Cys Ser Val Met His Glu Ala Leu His Asn His Tyr Thr Gln
430                 435                 440                 445
```

```
aag agc ctc tcc ctg tct ccg ggt aaa tga                              1422
Lys Ser Leu Ser Leu Ser Pro Gly Lys
            450

<210> SEQ ID NO 4
<211> LENGTH: 473
<212> TYPE: PRT
<213> ORGANISM: Artificial
<220> FEATURE:
<223> OTHER INFORMATION: Synthetic Construct

<400> SEQUENCE: 4

Met Ala Val Leu Gly Leu Leu Phe Cys Leu Val Thr Phe Pro Ser Cys
                -15                 -10                  -5

Val Leu Ser Gln Val Gln Leu Gln Glu Ser Gly Pro Gly Leu Val Lys
         -1  1               5                  10

Pro Ser Glu Thr Leu Ser Leu Thr Cys Thr Val Ser Gly Phe Ser Leu
         15                  20                  25

Pro Ser His Ser Val Ser Trp Ile Arg Gln Pro Pro Gly Lys Gly Leu
 30                  35                  40                  45

Glu Trp Ile Gly Ile Ile Trp Asn Gln Gly Thr Asp Tyr Asn Ser
                 50                  55                  60

Ala Phe Lys Ser Arg Val Thr Ile Ser Val Asp Thr Ser Lys Asn Gln
                 65                  70                  75

Phe Ser Leu Lys Leu Ser Ser Val Thr Ala Ala Asp Thr Ala Val Tyr
             80                  85                  90

Tyr Cys Ala Arg Asn Ala Tyr Ile Thr Asp Tyr Tyr Glu Asn Tyr
 95                 100                 105

Phe Met Asp Ala Trp Gly Gln Gly Thr Leu Val Thr Val Ser Ser Ala
110                 115                 120                 125

Ser Thr Lys Gly Pro Ser Val Phe Pro Leu Ala Pro Ser Ser Lys Ser
                130                 135                 140

Thr Ser Gly Gly Thr Ala Ala Leu Gly Cys Leu Val Lys Asp Tyr Phe
                145                 150                 155

Pro Glu Pro Val Thr Val Ser Trp Asn Ser Gly Ala Leu Thr Ser Gly
                160                 165                 170

Val His Thr Phe Pro Ala Val Leu Gln Ser Ser Gly Leu Tyr Ser Leu
175                 180                 185

Ser Ser Val Val Thr Val Pro Ser Ser Ser Leu Gly Thr Gln Thr Tyr
190                 195                 200                 205

Ile Cys Asn Val Asn His Lys Pro Ser Asn Thr Lys Val Asp Lys Lys
                210                 215                 220

Val Glu Pro Lys Ser Cys Asp Lys Thr His Thr Cys Pro Pro Cys Pro
                225                 230                 235

Ala Pro Glu Leu Leu Gly Gly Pro Ser Val Phe Leu Phe Pro Pro Lys
                240                 245                 250

Pro Lys Asp Thr Leu Met Ile Ser Arg Thr Pro Glu Val Thr Cys Val
                255                 260                 265

Val Val Asp Val Ser His Glu Asp Pro Glu Val Lys Phe Asn Trp Tyr
270                 275                 280                 285

Val Asp Gly Val Glu Val His Asn Ala Lys Thr Lys Pro Arg Glu Glu
                290                 295                 300

Gln Tyr Asn Ser Thr Tyr Arg Val Val Ser Val Leu Thr Val Leu His
                305                 310                 315

Gln Asp Trp Leu Asn Gly Lys Glu Tyr Lys Cys Lys Val Ser Asn Lys
```

```
                320                 325                 330
Ala Leu Pro Ala Pro Ile Glu Lys Thr Ile Ser Lys Ala Lys Gly Gln
            335                 340                 345

Pro Arg Glu Pro Gln Val Tyr Thr Leu Pro Pro Ser Arg Asp Glu Leu
350                 355                 360                 365

Thr Lys Asn Gln Val Ser Leu Thr Cys Leu Val Lys Gly Phe Tyr Pro
                370                 375                 380

Ser Asp Ile Ala Val Glu Trp Glu Ser Asn Gly Gln Pro Glu Asn Asn
            385                 390                 395

Tyr Lys Thr Thr Pro Pro Val Leu Asp Ser Asp Gly Ser Phe Phe Leu
        400                 405                 410

Tyr Ser Lys Leu Thr Val Asp Lys Ser Arg Trp Gln Gln Gly Asn Val
    415                 420                 425

Phe Ser Cys Ser Val Met His Glu Ala Leu His Asn His Tyr Thr Gln
430                 435                 440                 445

Lys Ser Leu Ser Leu Ser Pro Gly Lys
                450

<210> SEQ ID NO 5
<211> LENGTH: 114
<212> TYPE: PRT
<213> ORGANISM: Artificial
<220> FEATURE:
<223> OTHER INFORMATION: Humanized 16C10 and 4C3 Light Chain Variable
      Domain

<400> SEQUENCE: 5

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Phe Ser
            20                  25                  30

Glu Asn Gln Lys Asn Tyr Leu Ala Trp Tyr Leu Gln Lys Pro Gly Gln
        35                  40                  45

Ser Pro Gln Leu Leu Ile Tyr Trp Thr Ser Thr Arg Gln Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Tyr Thr Pro Tyr Thr Phe Gly Gln Gly Thr Lys Val Glu Ile
            100                 105                 110

Lys Arg

<210> SEQ ID NO 6
<211> LENGTH: 124
<212> TYPE: PRT
<213> ORGANISM: Artificial
<220> FEATURE:
<223> OTHER INFORMATION: Humanized 16C10 and 4C3 Heavy Chain Variable
      Domain

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Pro Ser His
            20                  25                  30

Ser Val Ser Trp Ile Arg Gln Pro Pro Gly Lys Gly Leu Glu Trp Ile
        35                  40                  45
```

```
Gly Ile Ile Trp Asn Gln Gly Gly Thr Asp Tyr Asn Ser Ala Phe Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asn Ala Tyr Ile Thr Asp Tyr Tyr Glu Asn Tyr Phe Met Asp
            100                 105                 110

Ala Trp Gly Gln Gly Thr Leu Val Thr Val Ser Ser
            115                 120

<210> SEQ ID NO 7
<211> LENGTH: 114
<212> TYPE: PRT
<213> ORGANISM: Rattus norvegicus

<400> SEQUENCE: 7

Asp Ile Val Met Thr Gln Ser Pro Ser Ser Leu Ala Val Ser Ile Gly
1               5                   10                  15

Glu Thr Val Thr Leu Asn Cys Lys Ser Ser Gln Ser Leu Leu Phe Ser
                20                  25                  30

Glu Asn Gln Lys Asn Tyr Leu Ala Trp Tyr Gln His Lys Ser Gly Gln
            35                  40                  45

Ser Pro Lys Leu Leu Val Tyr Trp Thr Ser Thr Arg Gln Ser Gly Val
    50                  55                  60

Pro Asp Arg Phe Met Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Ser Tyr Tyr Thr Pro Tyr Thr Phe Gly Ala Gly Thr Lys Leu Glu Leu
            100                 105                 110

Lys Arg

<210> SEQ ID NO 8
<211> LENGTH: 124
<212> TYPE: PRT
<213> ORGANISM: Rattus norvegicus

<400> SEQUENCE: 8

Gln Val Glu Leu Arg Glu Ser Gly Pro Gly Leu Val Gln Pro Ser Gln
1               5                   10                  15

Thr Leu Ser Leu Thr Cys Thr Val Ser Gly Phe Ser Leu Pro Ser His
                20                  25                  30

Ser Val Ser Trp Ile Arg Gln Pro Pro Gly Lys Gly Leu Glu Trp Met
            35                  40                  45

Gly Ile Ile Trp Asn Asn Gly Thr Asp Tyr Asn Ser Ala Phe Lys
    50                  55                  60

Ser Arg Leu Thr Ile Ser Arg Asp Thr Ser Lys Ser Gln Val Phe Leu
65                  70                  75                  80

Lys Met Asn Ser Leu Gln Thr Glu Asp Thr Ala Met Tyr Phe Cys Ala
                85                  90                  95

Arg Asn Met Tyr Ile Thr Asp Tyr Tyr Glu Asn Tyr Phe Met Asp
            100                 105                 110

Ala Trp Gly Gln Gly Ala Ser Val Thr Val Ser Ser
            115                 120
```

```
<210> SEQ ID NO 9
<211> LENGTH: 220
<212> TYPE: PRT
<213> ORGANISM: Artificial
<220> FEATURE:
<223> OTHER INFORMATION: Chimeric 16C10 Light Chain

<400> SEQUENCE: 9
```

Asp Ile Val Met Thr Gln Ser Pro Ser Ser Leu Ala Val Ser Ile Gly
 1               5                  10                  15

Glu Thr Val Thr Leu Asn Cys Lys Ser Ser Gln Ser Leu Leu Phe Ser
                20                  25                  30

Glu Asn Gln Lys Asn Tyr Leu Ala Trp Tyr Gln His Lys Ser Gly Gln
            35                  40                  45

Ser Pro Lys Leu Leu Val Tyr Trp Thr Ser Thr Arg Gln Ser Gly Val
        50                  55                  60

Pro Asp Arg Phe Met Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Ser Tyr Tyr Thr Pro Tyr Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

```
<210> SEQ ID NO 10
<211> LENGTH: 454
<212> TYPE: PRT
<213> ORGANISM: Artificial
<220> FEATURE:
<223> OTHER INFORMATION: Chimeric 16C10 Heavy Chain

<400> SEQUENCE: 10
```

Gln Val Glu Leu Arg Glu Ser Gly Pro Gly Leu Val Gln Pro Ser Gln
 1               5                  10                  15

Thr Leu Ser Leu Thr Cys Thr Val Ser Gly Phe Ser Leu Pro Ser His
                20                  25                  30

Ser Val Ser Trp Ile Arg Gln Pro Pro Gly Lys Gly Leu Glu Trp Met
            35                  40                  45

Gly Ile Ile Trp Asn Asn Gly Gly Thr Asp Tyr Asn Ser Ala Phe Lys
        50                  55                  60

Ser Arg Leu Thr Ile Ser Arg Asp Thr Ser Lys Ser Gln Val Phe Leu
65                  70                  75                  80

Lys Met Asn Ser Leu Gln Thr Glu Asp Thr Ala Met Tyr Phe Cys Ala
                85                  90                  95

```
Arg Asn Met Tyr Ile Thr Asp Tyr Tyr Glu Asn Tyr Phe Met Asp
            100                 105                 110
Ala Trp Gly Gln Gly Ala Ser Val Thr Val Ser Ser Ala Ser Thr Lys
        115                 120                 125
Gly Pro Ser Val Phe Pro Leu Ala Pro Ser Ser Lys Ser Thr Ser Gly
    130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
            180                 185                 190
Val Thr Val Pro Ser Ser Ser Leu Gly Thr Gln Thr Tyr Ile Cys Asn
        195                 200                 205
Val Asn His Lys Pro Ser Asn Thr Lys Val Asp Lys Lys Val Glu Pro
    210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Ser Arg Asp Glu Leu Thr Lys Asn
        355                 360                 365
Gln Val Ser Leu Thr Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450

<210> SEQ ID NO 11
<211> LENGTH: 17
<212> TYPE: PRT
<213> ORGANISM: Rattus norvegicus

<400> SEQUENCE: 11

Lys Ser Ser Gln Ser Leu Leu Phe Ser Glu Asn Gln Lys Asn Tyr Leu
```

```
1               5                  10                  15
Ala

<210> SEQ ID NO 12
<211> LENGTH: 7
<212> TYPE: PRT
<213> ORGANISM: Rattus norvegicus

<400> SEQUENCE: 12

Trp Thr Ser Thr Arg Gln Ser
1               5

<210> SEQ ID NO 13
<211> LENGTH: 9
<212> TYPE: PRT
<213> ORGANISM: Rattus norvegicus

<400> SEQUENCE: 13

Gln Gln Ser Tyr Tyr Thr Pro Tyr Thr
1               5

<210> SEQ ID NO 14
<211> LENGTH: 10
<212> TYPE: PRT
<213> ORGANISM: Rattus norvegicus

<400> SEQUENCE: 14

Gly Phe Ser Leu Pro Ser His Ser Val Ser
1               5                  10

<210> SEQ ID NO 15
<211> LENGTH: 16
<212> TYPE: PRT
<213> ORGANISM: Rattus norvegicus

<400> SEQUENCE: 15

Ile Ile Trp Asn Asn Gly Gly Thr Asp Tyr Asn Ser Ala Phe Lys Ser
1               5                  10                  15

<210> SEQ ID NO 16
<211> LENGTH: 16
<212> TYPE: PRT
<213> ORGANISM: Artificial
<220> FEATURE:
<223> OTHER INFORMATION: Humanized 16C10 CDRH2 (N54Q)

<400> SEQUENCE: 16

Ile Ile Trp Asn Gln Gly Gly Thr Asp Tyr Asn Ser Ala Phe Lys Ser
1               5                  10                  15

<210> SEQ ID NO 17
<211> LENGTH: 16
<212> TYPE: PRT
<213> ORGANISM: Artificial
<220> FEATURE:
<223> OTHER INFORMATION: Rat 16C10 CDRH2 (N54N/Q/A)
<220> FEATURE:
<221> NAME/KEY: VARIANT
<222> LOCATION: (5)..(5)
<223> OTHER INFORMATION: Xaa can be Ala, Asn or Gln

<400> SEQUENCE: 17

Ile Ile Trp Asn Xaa Gly Gly Thr Asp Tyr Asn Ser Ala Phe Lys Ser
1               5                  10                  15
```

```
<210> SEQ ID NO 18
<211> LENGTH: 16
<212> TYPE: PRT
<213> ORGANISM: Rattus norvegicus

<400> SEQUENCE: 18

Asn Met Tyr Ile Thr Asp Tyr Tyr Tyr Glu Asn Tyr Phe Met Asp Ala
1               5                   10                  15

<210> SEQ ID NO 19
<211> LENGTH: 16
<212> TYPE: PRT
<213> ORGANISM: Artificial
<220> FEATURE:
<223> OTHER INFORMATION: Humanized 16C10 CDRH3 (M96A)

<400> SEQUENCE: 19

Asn Ala Tyr Ile Thr Asp Tyr Tyr Tyr Glu Asn Tyr Phe Met Asp Ala
1               5                   10                  15

<210> SEQ ID NO 20
<211> LENGTH: 16
<212> TYPE: PRT
<213> ORGANISM: Artificial
<220> FEATURE:
<223> OTHER INFORMATION: Rat 16C10 CDRH3 (M96M/L/A/K/F, M100hM/L/F)
<220> FEATURE:
<221> NAME/KEY: VARIANT
<222> LOCATION: (2)..(2)
<223> OTHER INFORMATION: Xaa can be Met, Leu, Ala, Lys or Phe
<220> FEATURE:
<221> NAME/KEY: VARIANT
<222> LOCATION: (14)..(14)
<223> OTHER INFORMATION: Xaa can be Met, Leu or Phe

<400> SEQUENCE: 20

Asn Xaa Tyr Ile Thr Asp Tyr Tyr Tyr Glu Asn Tyr Phe Xaa Asp Ala
1               5                   10                  15

<210> SEQ ID NO 21
<211> LENGTH: 114
<212> TYPE: PRT
<213> ORGANISM: Artificial
<220> FEATURE:
<223> OTHER INFORMATION: Rat 4C3 Light Chain Variable Domain

<400> SEQUENCE: 21

Asp Ile Val Met Thr Gln Ser Pro Ser Ser Leu Ala Val Ser Val Gly
1               5                   10                  15

Glu Thr Val Thr Leu Asn Cys Lys Ser Ser Gln Ser Leu Leu Phe Ser
                20                  25                  30

Glu Asn Gln Lys Asn Tyr Leu Ala Trp Tyr Gln His Lys Ser Gly Gln
            35                  40                  45

Ser Pro Lys Leu Leu Val Tyr Trp Thr Ser Thr Arg Gln Ser Gly Val
        50                  55                  60

Pro Asp Arg Phe Met Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Ser Tyr Tyr Thr Pro Tyr Thr Phe Gly Ala Gly Thr Lys Leu Glu Leu
            100                 105                 110

Lys Arg

<210> SEQ ID NO 22
```

```
<211> LENGTH: 113
<212> TYPE: PRT
<213> ORGANISM: Artificial
<220> FEATURE:
<223> OTHER INFORMATION: Humanized 30C10 Light Chain Variable Domain

<400> SEQUENCE: 22

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Phe Trp Ser
            20                  25                  30

Glu Ser His Met Asn Tyr Leu Ala Trp Tyr Leu Gln Lys Pro Gly Gln
        35                  40                  45

Ser Pro Gln Leu Leu Ile Tyr Tyr Ala Ser Thr Arg Gln Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys His His
                85                  90                  95

His Tyr Asp Ser His Thr Phe Gly Gln Gly Thr Lys Val Glu Ile Lys
            100                 105                 110

Arg

<210> SEQ ID NO 23
<211> LENGTH: 117
<212> TYPE: PRT
<213> ORGANISM: artificial
<220> FEATURE:
<223> OTHER INFORMATION: Humanized 30C10 Heavy Chain Variable Domain

<400> SEQUENCE: 23

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Ser Val Ser Asn Thr Gly Ser Ser Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ala Tyr Tyr Leu Asp Tyr Trp Gly Gln Gly Thr Leu
            100                 105                 110

Val Thr Val Ser Ser
        115

<210> SEQ ID NO 24
<211> LENGTH: 113
<212> TYPE: PRT
<213> ORGANISM: Rattus norvegicus

<400> SEQUENCE: 24

Asp Ile Val Met Thr Gln Ser Pro Ser Ser Leu Ala Val Ser Pro Gly
1               5                   10                  15

Glu Thr Val Thr Ile Asn Cys Lys Ser Ser Gln Ser Leu Phe Trp Ser
            20                  25                  30
```

Glu Ser His Met Asn Tyr Leu Ala Trp Tyr Gln Gln Lys Pro Gly Gln
            35                  40                  45

Ser Pro Lys Leu Leu Ile Tyr Tyr Ala Ser Thr Arg Gln Ser Gly Val
        50                  55                  60

Pro Asp Arg Phe Ile Gly Ser Gly Ser Gly Thr Asp Phe Thr Leu Thr
65                  70                  75                  80

Ile Ser Gly Val Gln Ala Glu Asp Leu Ala Val Tyr Tyr Cys His His
                85                  90                  95

His Tyr Asp Ser His Thr Phe Gly Ala Gly Thr Lys Leu Glu Leu Lys
                100                 105                 110

Arg

<210> SEQ ID NO 25
<211> LENGTH: 117
<212> TYPE: PRT
<213> ORGANISM: Rattus norvegicus

<400> SEQUENCE: 25

Glu Val Gln Leu Val Glu Ser Gly Gly Gly Leu Val Gln Pro Gly Arg
1               5                   10                  15

Ser Gln Lys Leu Ser Cys Val Val Ser Gly Phe Thr Phe Asn Asn Tyr
            20                  25                  30

Trp Met Thr Trp Ile Arg Gln Ala Pro Gly Lys Gly Leu Glu Trp Val
        35                  40                  45

Ala Ser Val Ser Asn Thr Gly Ser Ser Thr Tyr Tyr Pro Ala Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Glu Gly Ala Tyr Tyr Leu Asp Tyr Trp Gly Gln Gly Val Met
                100                 105                 110

Val Thr Val Ser Ser
        115

<210> SEQ ID NO 26
<211> LENGTH: 17
<212> TYPE: PRT
<213> ORGANISM: Rattus norvegicus

<400> SEQUENCE: 26

Lys Ser Ser Gln Ser Leu Phe Trp Ser Glu Ser His Met Asn Tyr Leu
1               5                   10                  15

Ala

<210> SEQ ID NO 27
<211> LENGTH: 7
<212> TYPE: PRT
<213> ORGANISM: Rattus norvegicus

<400> SEQUENCE: 27

Tyr Ala Ser Thr Arg Gln Ser
1               5

<210> SEQ ID NO 28
<211> LENGTH: 8
<212> TYPE: PRT
<213> ORGANISM: Rattus norvegicus

```
<400> SEQUENCE: 28

His His His Tyr Asp Ser His Thr
1               5

<210> SEQ ID NO 29
<211> LENGTH: 10
<212> TYPE: PRT
<213> ORGANISM: Rattus norvegicus

<400> SEQUENCE: 29

Gly Phe Thr Phe Asn Asn Tyr Trp Met Thr
1               5                   10

<210> SEQ ID NO 30
<211> LENGTH: 17
<212> TYPE: PRT
<213> ORGANISM: Rattus norvegicus

<400> SEQUENCE: 30

Ser Val Ser Asn Thr Gly Ser Ser Thr Tyr Tyr Pro Ala Ser Val Lys
1               5                   10                  15

Gly

<210> SEQ ID NO 31
<211> LENGTH: 8
<212> TYPE: PRT
<213> ORGANISM: Rattus norvegicus

<400> SEQUENCE: 31

Glu Gly Ala Tyr Tyr Leu Asp Tyr
1               5

<210> SEQ ID NO 32
<211> LENGTH: 108
<212> TYPE: PRT
<213> ORGANISM: Rattus norvegicus

<400> SEQUENCE: 32

Asp Ile Gln Met Thr Gln Ser Pro Ser Ser Leu Ser Ala Ser Leu Gly
1               5                   10                  15

Asp Arg Val Thr Ile Thr Cys Arg Thr Ser Gln Asp Ile Gly Asn Tyr
            20                  25                  30

Leu Ser Trp Phe Gln Gln Lys Pro Gly Lys Ser Pro Arg Leu Met Ile
        35                  40                  45

Tyr Gly Ala Ser Asn Leu Glu Asp Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Thr Ala Ile Tyr Tyr Cys Leu Gln Tyr Asp Lys Tyr Pro Asn
                85                  90                  95

Thr Phe Gly Ala Gly Thr Lys Leu Glu Leu Lys Arg
            100                 105

<210> SEQ ID NO 33
<211> LENGTH: 117
<212> TYPE: PRT
<213> ORGANISM: Rattus norvegicus

<400> SEQUENCE: 33

Glu Val Gln Leu Glu Glu Ser Gly Gly Gly Leu Val Gln Pro Gly Arg
1               5                   10                  15
```

Ser Leu Lys Leu Ser Cys Ala Ala Ser Gly Phe Thr Phe Arg Asp Tyr
            20                  25                  30

Tyr Met Val Trp Val Arg Gln Ala Pro Lys Lys Gly Leu Glu Trp Val
        35                  40                  45

Ala Ser Ile Ser Tyr Glu Gly Ser Ser Ile Tyr Tyr Gly Glu Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Ala Arg His Gly Phe Asn Pro Phe Asp Tyr Trp Gly Arg Gly Val Met
            100                 105                 110

Val Thr Val Ser Ser
        115

<210> SEQ ID NO 34
<211> LENGTH: 11
<212> TYPE: PRT
<213> ORGANISM: Rattus norvegicus

<400> SEQUENCE: 34

Arg Thr Ser Gln Asp Ile Gly Asn Tyr Leu Ser
1               5                   10

<210> SEQ ID NO 35
<211> LENGTH: 7
<212> TYPE: PRT
<213> ORGANISM: Rattus norvegicus

<400> SEQUENCE: 35

Gly Ala Ser Asn Leu Glu Asp
1               5

<210> SEQ ID NO 36
<211> LENGTH: 9
<212> TYPE: PRT
<213> ORGANISM: Rattus norvegicus

<400> SEQUENCE: 36

Leu Gln Tyr Asp Lys Tyr Pro Asn Thr
1               5

<210> SEQ ID NO 37
<211> LENGTH: 10
<212> TYPE: PRT
<213> ORGANISM: Rattus norvegicus

<400> SEQUENCE: 37

Gly Phe Thr Phe Arg Asp Tyr Tyr Met Val
1               5                   10

<210> SEQ ID NO 38
<211> LENGTH: 17
<212> TYPE: PRT
<213> ORGANISM: artificial
<220> FEATURE:
<223> OTHER INFORMATION: Rat/Humanized 12E6 CDRH2

<400> SEQUENCE: 38

Ser Ile Ser Tyr Glu Gly Ser Ser Ile Tyr Tyr Gly Glu Ser Val Lys
1               5                   10                  15

Gly

<210> SEQ ID NO 39
<211> LENGTH: 8
<212> TYPE: PRT
<213> ORGANISM: Rattus norvegicus

<400> SEQUENCE: 39

His Gly Phe Asn Pro Phe Asp Tyr
1               5

<210> SEQ ID NO 40
<211> LENGTH: 132
<212> TYPE: PRT
<213> ORGANISM: Homo sapiens

<400> SEQUENCE: 40

Gly Ile Thr Ile Pro Arg Asn Pro Gly Cys Pro Asn Ser Glu Asp Lys
1               5                   10                  15

Asn Phe Pro Arg Thr Val Met Val Asn Leu Asn Ile His Asn Arg Asn
                20                  25                  30

Thr Asn Thr Asn Pro Lys Arg Ser Ser Asp Tyr Tyr Asn Arg Ser Thr
            35                  40                  45

Ser Pro Trp Asn Leu His Arg Asn Glu Asp Pro Glu Arg Tyr Pro Ser
    50                  55                  60

Val Ile Trp Glu Ala Lys Cys Arg His Leu Gly Cys Ile Asn Ala Asp
65                  70                  75                  80

Gly Asn Val Asp Tyr His Met Asn Ser Val Pro Ile Gln Gln Glu Ile
                85                  90                  95

Leu Val Leu Arg Arg Glu Pro Pro His Cys Pro Asn Ser Phe Arg Leu
            100                 105                 110

Glu Lys Ile Leu Val Ser Val Gly Cys Thr Cys Val Thr Pro Ile Val
        115                 120                 125

His His Val Ala
    130

<210> SEQ ID NO 41
<211> LENGTH: 134
<212> TYPE: PRT
<213> ORGANISM: Artificial
<220> FEATURE:
<223> OTHER INFORMATION: recombinant human IL-17A

<400> SEQUENCE: 41

Leu Glu Gly Ile Thr Ile Pro Arg Asn Pro Gly Cys Pro Asn Ser Glu
1               5                   10                  15

Asp Lys Asn Phe Pro Arg Thr Val Met Val Asn Leu Asn Ile His Asn
                20                  25                  30

Arg Asn Thr Asn Thr Asn Pro Lys Arg Ser Ser Asp Tyr Tyr Asn Arg
            35                  40                  45

Ser Thr Ser Pro Trp Asn Leu His Arg Asn Glu Asp Pro Glu Arg Tyr
    50                  55                  60

Pro Ser Val Ile Trp Glu Ala Lys Cys Arg His Leu Gly Cys Ile Asn
65                  70                  75                  80

Ala Asp Gly Asn Val Asp Tyr His Met Asn Ser Val Pro Ile Gln Gln
                85                  90                  95

Glu Ile Leu Val Leu Arg Arg Glu Pro Pro His Cys Pro Asn Ser Phe
            100                 105                 110

```
Arg Leu Glu Lys Ile Leu Val Ser Val Gly Cys Thr Cys Val Thr Pro
        115                 120                 125

Ile Val His His Val Ala
        130
```

<210> SEQ ID NO 42
<211> LENGTH: 141
<212> TYPE: PRT
<213> ORGANISM: Artificial
<220> FEATURE:
<223> OTHER INFORMATION: FLAG-tagged human IL-17A

<400> SEQUENCE: 42

```
Asp Tyr Lys Asp Asp Asp Asp Lys Leu Gly Ile Thr Ile Pro Arg Asn
1               5                   10                  15

Pro Gly Cys Pro Asn Ser Glu Asp Lys Asn Phe Pro Arg Thr Val Met
            20                  25                  30

Val Asn Leu Asn Ile His Asn Arg Asn Thr Asn Thr Asn Pro Lys Arg
        35                  40                  45

Ser Ser Asp Tyr Tyr Asn Arg Ser Thr Ser Pro Trp Asn Leu His Arg
    50                  55                  60

Asn Glu Asp Pro Glu Arg Tyr Pro Ser Val Ile Trp Glu Ala Lys Cys
65                  70                  75                  80

Arg His Leu Gly Cys Ile Asn Ala Asp Gly Asn Val Asp Tyr His Met
                85                  90                  95

Asn Ser Val Pro Ile Gln Gln Glu Ile Leu Val Leu Arg Arg Glu Pro
            100                 105                 110

Pro His Cys Pro Asn Ser Phe Arg Leu Glu Lys Ile Leu Val Ser Val
        115                 120                 125

Gly Cys Thr Cys Val Thr Pro Ile Val His His Val Ala
    130                 135                 140
```

<210> SEQ ID NO 43
<211> LENGTH: 137
<212> TYPE: PRT
<213> ORGANISM: Homo sapiens

<400> SEQUENCE: 43

```
Met Ile Val Lys Ala Gly Ile Thr Ile Pro Arg Asn Pro Gly Cys Pro
1               5                   10                  15

Asn Ser Glu Asp Lys Asn Phe Pro Arg Thr Val Met Val Asn Leu Asn
            20                  25                  30

Ile His Asn Arg Asn Thr Asn Thr Asn Pro Lys Arg Ser Ser Asp Tyr
        35                  40                  45

Tyr Asn Arg Ser Thr Ser Pro Trp Asn Leu His Arg Asn Glu Asp Pro
    50                  55                  60

Glu Arg Tyr Pro Ser Val Ile Trp Glu Ala Lys Cys Arg His Leu Gly
65                  70                  75                  80

Cys Ile Asn Ala Asp Gly Asn Val Asp Tyr His Met Asn Ser Val Pro
                85                  90                  95

Ile Gln Gln Glu Ile Leu Val Leu Arg Arg Glu Pro Pro His Cys Pro
            100                 105                 110

Asn Ser Phe Arg Leu Glu Lys Ile Leu Val Ser Val Gly Cys Thr Cys
        115                 120                 125

Val Thr Pro Ile Val His His Val Ala
    130                 135
```

<210> SEQ ID NO 44
<211> LENGTH: 384
<212> TYPE: DNA
<213> ORGANISM: Rattus norvegicus
<220> FEATURE:
<221> NAME/KEY: CDS
<222> LOCATION: (1)..(384)
<220> FEATURE:
<221> NAME/KEY: sig_peptide
<222> LOCATION: (1)..(60)
<220> FEATURE:
<221> NAME/KEY: mat_peptide
<222> LOCATION: (61)..(384)

<400> SEQUENCE: 44

```
atg ggc gtg ccc act cag ctc ctg ggg ttg ttg ctg tgg att aca          48
Met Gly Val Pro Thr Gln Leu Leu Gly Leu Leu Leu Trp Ile Thr
-20             -15                 -10                 -5 gat gtc ata tgt gac atc cag atg aca cag tct cca gct tcc ctg tct      96
Asp Val Ile Cys Asp Ile Gln Met Thr Gln Ser Pro Ala Ser Leu Ser
        -1  1               5                   10 gca tct ctg gga gaa act gtc acc atc caa tgt caa gca agt gag gac     144
Ala Ser Leu Gly Glu Thr Val Thr Ile Gln Cys Gln Ala Ser Glu Asp
        15                  20                  25 att tac agt ggt tta gcg tgg tat cat cag aag cca ggg aag tct cct     192
Ile Tyr Ser Gly Leu Ala Trp Tyr His Gln Lys Pro Gly Lys Ser Pro
        30                  35                  40 caa ctc ctg atc ctt ggt gct agt agg tta cac gac ggc gtc cca tca     240
Gln Leu Leu Ile Leu Gly Ala Ser Arg Leu His Asp Gly Val Pro Ser
45                  50                  55                  60 cga ttc agt ggc agt gga tct ggc ata gag tat tct ctc aag atc aac     288
Arg Phe Ser Gly Ser Gly Ser Gly Ile Glu Tyr Ser Leu Lys Ile Asn
                65                  70                  75 aac atg caa act gaa gat gaa ggg att tat ttc tgt caa cag ggt tta     336
Asn Met Gln Thr Glu Asp Glu Gly Ile Tyr Phe Cys Gln Gln Gly Leu
            80                  85                  90 aag tat cct ccg acg ttc ggt gga ggc acc aag ctg gaa ttg aaa cgg     384
Lys Tyr Pro Pro Thr Phe Gly Gly Gly Thr Lys Leu Glu Leu Lys Arg
        95                  100                 105
```

<210> SEQ ID NO 45
<211> LENGTH: 128
<212> TYPE: PRT
<213> ORGANISM: Rattus norvegicus

<400> SEQUENCE: 45

```
Met Gly Val Pro Thr Gln Leu Leu Gly Leu Leu Leu Trp Ile Thr
-20             -15                 -10                 -5

Asp Val Ile Cys Asp Ile Gln Met Thr Gln Ser Pro Ala Ser Leu Ser
        -1  1               5                   10

Ala Ser Leu Gly Glu Thr Val Thr Ile Gln Cys Gln Ala Ser Glu Asp
        15                  20                  25

Ile Tyr Ser Gly Leu Ala Trp Tyr His Gln Lys Pro Gly Lys Ser Pro
        30                  35                  40

Gln Leu Leu Ile Leu Gly Ala Ser Arg Leu His Asp Gly Val Pro Ser
45                  50                  55                  60

Arg Phe Ser Gly Ser Gly Ser Gly Ile Glu Tyr Ser Leu Lys Ile Asn
                65                  70                  75

Asn Met Gln Thr Glu Asp Glu Gly Ile Tyr Phe Cys Gln Gln Gly Leu
            80                  85                  90

Lys Tyr Pro Pro Thr Phe Gly Gly Gly Thr Lys Leu Glu Leu Lys Arg
        95                  100                 105
```

<210> SEQ ID NO 46
<211> LENGTH: 411
<212> TYPE: DNA
<213> ORGANISM: Rattus norvegicus
<220> FEATURE:
<221> NAME/KEY: CDS
<222> LOCATION: (1)..(411)
<220> FEATURE:
<221> NAME/KEY: sig_peptide
<222> LOCATION: (1)..(57)
<220> FEATURE:
<221> NAME/KEY: mat_peptide
<222> LOCATION: (58)..(411)

<400> SEQUENCE: 46

| atg | gct | gtc | ctg | gtg | ctg | ttg | ctc | tgc | ctg | gtg | aca | ttc | cca | aga | tgt | 48 |
|---|---|---|---|---|---|---|---|---|---|---|---|---|---|---|---|---|
| Met | Ala | Val | Leu | Val | Leu | Leu | Cys | Leu | Val | Thr | Phe | Pro | Arg | Cys | | |
| | | | -15 | | | | -10 | | | | | -5 | | | | |

| gtc | ctg | tcc | cag | gtg | cag | ttg | aag | gag | tca | gga | cct | ggt | ctg | gtg | cag | 96 |
|---|---|---|---|---|---|---|---|---|---|---|---|---|---|---|---|---|
| Val | Leu | Ser | Gln | Val | Gln | Leu | Lys | Glu | Ser | Gly | Pro | Gly | Leu | Val | Gln | |
| | -1 | 1 | | | | 5 | | | | | | 10 | | | | |

| ccc | tca | cag | acc | ctg | tct | ctc | acc | tgc | act | gtc | ttt | gga | ttc | tca | ttg | 144 |
|---|---|---|---|---|---|---|---|---|---|---|---|---|---|---|---|---|
| Pro | Ser | Gln | Thr | Leu | Ser | Leu | Thr | Cys | Thr | Val | Phe | Gly | Phe | Ser | Leu | |
| | 15 | | | | | 20 | | | | | 25 | | | | | |

| acc | aac | aat | ggt | gtg | acc | tgg | gtt | cgc | cag | cct | cca | gga | aag | ggt | ctg | 192 |
|---|---|---|---|---|---|---|---|---|---|---|---|---|---|---|---|---|
| Thr | Asn | Asn | Gly | Val | Thr | Trp | Val | Arg | Gln | Pro | Pro | Gly | Lys | Gly | Leu | |
| 30 | | | | 35 | | | | | 40 | | | | | 45 | | |

| gag | tgg | att | gca | gaa | gta | tca | agc | ggt | ggc | agc | aca | gat | tat | aat | tca | 240 |
|---|---|---|---|---|---|---|---|---|---|---|---|---|---|---|---|---|
| Glu | Trp | Ile | Ala | Glu | Val | Ser | Ser | Gly | Gly | Ser | Thr | Asp | Tyr | Asn | Ser | |
| | | | | 50 | | | | | 55 | | | | | 60 | | |

| gcc | ctc | aaa | tcc | cga | ctg | agc | atc | agt | agg | gac | acc | tcc | aag | agc | caa | 288 |
|---|---|---|---|---|---|---|---|---|---|---|---|---|---|---|---|---|
| Ala | Leu | Lys | Ser | Arg | Leu | Ser | Ile | Ser | Arg | Asp | Thr | Ser | Lys | Ser | Gln | |
| | 65 | | | | | 70 | | | | | 75 | | | | | |

| gtt | ttc | tta | aga | atg | aac | agt | ctg | cag | act | gaa | gac | aca | gcc | att | tac | 336 |
|---|---|---|---|---|---|---|---|---|---|---|---|---|---|---|---|---|
| Val | Phe | Leu | Arg | Met | Asn | Ser | Leu | Gln | Thr | Glu | Asp | Thr | Ala | Ile | Tyr | |
| | 80 | | | | | 85 | | | | | 90 | | | | | |

| ttc | tgt | gcc | aga | cag | gag | gta | ttt | acc | gga | tta | ttg | gat | tat | tgg | ggc | 384 |
|---|---|---|---|---|---|---|---|---|---|---|---|---|---|---|---|---|
| Phe | Cys | Ala | Arg | Gln | Glu | Val | Phe | Thr | Gly | Leu | Leu | Asp | Tyr | Trp | Gly | |
| | 95 | | | | | 100 | | | | | 105 | | | | | |

| caa | gga | gtc | atg | gtc | aca | gtc | tcc | tcg | | | | | | | | 411 |
|---|---|---|---|---|---|---|---|---|---|---|---|---|---|---|---|---|
| Gln | Gly | Val | Met | Val | Thr | Val | Ser | Ser | | | | | | | | |
| 110 | | | | 115 | | | | | | | | | | | | |

<210> SEQ ID NO 47
<211> LENGTH: 137
<212> TYPE: PRT
<213> ORGANISM: Rattus norvegicus

<400> SEQUENCE: 47

Met Ala Val Leu Val Leu Leu Cys Leu Val Thr Phe Pro Arg Cys
                -15                 -10                 -5

Val Leu Ser Gln Val Gln Leu Lys Glu Ser Gly Pro Gly Leu Val Gln
        -1  1               5                       10

Pro Ser Gln Thr Leu Ser Leu Thr Cys Thr Val Phe Gly Phe Ser Leu
        15                  20                  25

Thr Asn Asn Gly Val Thr Trp Val Arg Gln Pro Pro Gly Lys Gly Leu
30                  35                  40                  45

Glu Trp Ile Ala Glu Val Ser Ser Gly Gly Ser Thr Asp Tyr Asn Ser
                50                  55                  60

Ala Leu Lys Ser Arg Leu Ser Ile Ser Arg Asp Thr Ser Lys Ser Gln
        65                  70                  75

```
Val Phe Leu Arg Met Asn Ser Leu Gln Thr Glu Asp Thr Ala Ile Tyr
            80                  85                  90

Phe Cys Ala Arg Gln Glu Val Phe Thr Gly Leu Leu Asp Tyr Trp Gly
        95                 100                 105

Gln Gly Val Met Val Thr Val Ser Ser
110                 115

<210> SEQ ID NO 48
<211> LENGTH: 11
<212> TYPE: PRT
<213> ORGANISM: Rattus norvegicus

<400> SEQUENCE: 48

Gln Ala Ser Glu Asp Ile Tyr Ser Gly Leu Ala
1               5                   10

<210> SEQ ID NO 49
<211> LENGTH: 7
<212> TYPE: PRT
<213> ORGANISM: Rattus norvegicus

<400> SEQUENCE: 49

Gly Ala Ser Arg Leu His Asp
1               5

<210> SEQ ID NO 50
<211> LENGTH: 9
<212> TYPE: PRT
<213> ORGANISM: Rattus norvegicus

<400> SEQUENCE: 50

Gln Gln Gly Leu Lys Tyr Pro Pro Thr
1               5

<210> SEQ ID NO 51
<211> LENGTH: 10
<212> TYPE: PRT
<213> ORGANISM: Rattus norvegicus

<400> SEQUENCE: 51

Gly Phe Ser Leu Thr Asn Asn Gly Val Thr
1               5                   10

<210> SEQ ID NO 52
<211> LENGTH: 16
<212> TYPE: PRT
<213> ORGANISM: Rattus norvegicus

<400> SEQUENCE: 52

Glu Val Ser Ser Gly Gly Ser Thr Asp Tyr Asn Ser Ala Leu Lys Ser
1               5                   10                  15

<210> SEQ ID NO 53
<211> LENGTH: 10
<212> TYPE: PRT
<213> ORGANISM: Rattus norvegicus

<400> SEQUENCE: 53

Gln Glu Val Phe Thr Gly Leu Leu Asp Tyr
1               5                   10

<210> SEQ ID NO 54
<211> LENGTH: 108
```

```
<212> TYPE: PRT
<213> ORGANISM: Rattus sp.

<400> SEQUENCE: 54

Asp Ile Gln Met Thr Gln Ser Pro Ser Phe Leu Ser Ala Ser Val Gly
1               5                   10                  15

Glu Arg Val Thr Leu Ser Cys Lys Ala Ser Gln Asn Ile Asn Lys Tyr
            20                  25                  30

Leu Asp Trp Phe Gln Gln Lys Leu Gly Glu Ala Pro Lys Leu Leu Ile
        35                  40                  45

Tyr Asn Ala Asp Asn Leu His Thr Gly Ile Pro Ser Arg Phe Ser Gly
50                  55                  60

Ser Gly Ser Phe Ser Asp Phe Ile Leu Thr Ile Ser Ser Leu Gln Pro
65                  70                  75                  80

Glu Asp Asp Ala Thr Tyr Phe Cys Leu Gln Arg Glu Ser Trp Pro Tyr
                85                  90                  95

Thr Phe Gly Ala Gly Thr Lys Leu Glu Leu Lys Arg
            100                 105

<210> SEQ ID NO 55
<211> LENGTH: 122
<212> TYPE: PRT
<213> ORGANISM: Rattus sp.

<400> SEQUENCE: 55

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Tyr
            20                  25                  30

Tyr Val His Trp Val Arg Gln Pro Pro Gly Lys Gly Leu Glu Trp Met
        35                  40                  45

Gly Gly Val Trp Asn Asp Gly Asp Thr Ser Tyr Asn Ser Val Leu Arg
    50                  55                  60

Ser Arg Leu Ser Ile Thr Arg Asp Thr Ser Lys Ser Gln Val Leu Leu
65                  70                  75                  80

Lys Met Ser Ser Leu Gln Thr Glu Asp Thr Ala Thr Tyr Tyr Cys Ala
                85                  90                  95

Arg Glu Gly Arg Glu Gly Phe Val Gly Tyr Tyr Val Met Asp Ala Trp
            100                 105                 110

Gly Pro Gly Ala Ser Val Thr Val Ser Ser
        115                 120

<210> SEQ ID NO 56
<211> LENGTH: 11
<212> TYPE: PRT
<213> ORGANISM: Rattus sp.

<400> SEQUENCE: 56

Lys Ala Ser Gln Asn Ile Asn Lys Tyr Leu Asp
1               5                   10

<210> SEQ ID NO 57
<211> LENGTH: 7
<212> TYPE: PRT
<213> ORGANISM: Rattus sp.

<400> SEQUENCE: 57

Asn Ala Asp Asn Leu His Thr
1               5
```

<210> SEQ ID NO 58
<211> LENGTH: 9
<212> TYPE: PRT
<213> ORGANISM: Rattus sp.

<400> SEQUENCE: 58

Leu Gln Arg Glu Ser Trp Pro Tyr Thr
1               5

<210> SEQ ID NO 59
<211> LENGTH: 10
<212> TYPE: PRT
<213> ORGANISM: Rattus sp.

<400> SEQUENCE: 59

Ser Leu Thr Asn Tyr Tyr Val His Trp Val
1               5                   10

<210> SEQ ID NO 60
<211> LENGTH: 16
<212> TYPE: PRT
<213> ORGANISM: Rattus sp.

<400> SEQUENCE: 60

Gly Val Trp Asn Asp Gly Asp Thr Ser Tyr Asn Ser Val Leu Arg Ser
1               5                   10                  15

<210> SEQ ID NO 61
<211> LENGTH: 14
<212> TYPE: PRT
<213> ORGANISM: Rattus sp.

<400> SEQUENCE: 61

Glu Gly Arg Glu Gly Phe Val Gly Tyr Tyr Val Met Asp Ala
1               5                   10

<210> SEQ ID NO 62
<211> LENGTH: 720
<212> TYPE: DNA
<213> ORGANISM: Artificial sequence
<220> FEATURE:
<223> OTHER INFORMATION: Humanized 16C10 Antibody Light Chain with
      Signal Sequence

<400> SEQUENCE: 62 atggccccccg tgcagctgct gggcctgctg gtgctgttcc tgcccgccat gagatgcgac    60
atcgtgatga cccagagccc cctgagcctg cccgtgaccc aggcgagcc cgccagcatc    120 agctgcaaga gcagccagag cctgctgttc agcgagaacc agaagaacta cctggcctgg    180
tatctgcaga agcccggcca gtcccccag ctgctgatct actggaccag caccaggcag    240
agcggcgtgc ccgacaggtt cagcggcagc ggctccggca ccgacttcac cctgaagatc    300
agcagggtgg aggccgagga cgtgggcgtg tactactgcc agcagagcta ctacaccccc    360 tacacccttcg gccagggcac caaggtggag atcaagcgta cggtggctgc ccccagcgtg    420
ttcatcttcc cccccagcga cgagcagctg aagagcggca ccgccagcgt ggtgtgcctg    480
ctgaacaact ctacccccg ggaggccaag gtgcagtgga aggtggacaa cgccctgcag    540
agcggcaaca gccaggaaag cgtcaccgag caggacagca aggactccac ctacagcctg    600
agcagcaccc tgaccctgag caaggccgac tacgagaagc acaaggtgta cgcctgcgag    660
gtgacccacc agggcctgtc cagccccgtg accaagagct caacagggg cgagtgctag    720

<210> SEQ ID NO 63
<211> LENGTH: 1422
<212> TYPE: DNA
<213> ORGANISM: Artificial Sequence
<220> FEATURE:
<223> OTHER INFORMATION: Humanized 16C10 Antibody Heavy Chain with
      Signal Sequence

<400> SEQUENCE: 63

```
atggccgtgc tgggcctgct gttctgcctg gtgaccttcc ccagctgcgt gctgtcccag      60
gtgcagctgc aggaaagcgg cccaggcctg gtgaagccca gcgagaccct gagcctgacc     120
tgcaccgtga gcggcttcag cctgcccagc cacagcgtga gctggatcag cagcccccca     180
ggcaagggcc tggaatggat cggcatcatc tggaaccagg cggcaccga ctacaacagc      240
gccttcaaga gcagggtgac catcagcgtg gacaccagca agaaccagtt cagcctgaag     300
ctgtccagcg tgacagccgc cgacaccgcc gtgtactact gcgccaggaa cgcctacatc     360
accgactact actacgagaa ctacttcatg gacgcctggg gccagggcac cctggtgacc     420
gtgagcagcg ctagcaccaa gggcccaagc gtgttccccc tggcccccag cagcaagagc     480
acctccggcg gcacagccgc cctgggctgt ctggtgaagg actacttccc cgagcccgtg     540
accgtgtcct ggaacagcgg agccctgacc agcggcgtgc acaccttccc cgccgtgctg     600
cagagcagcg gcctgtacag cctgagcagc gtggtgacag tgcccagcag cagcctgggc     660
acccagacct acatctgcaa cgtgaaccac aagcccagca caccaaggt ggacaagaa       720
gtggagccca gagctgcga caagacccac acctgccccc cctgccctgc cccagagctg      780
ctgggcggac ccagcgtgtt cctgttcccc ccaagcccca ggacaccct gatgatcagc      840
aggaccccg aggtgacctg cgtggtggtg gacgtgagcc acgaggaccc agaggtgaag     900
ttcaactggt acgtggacgg cgtggaggtg cacaacgcca agaccaagcc cagagaggaa     960
cagtacaaca gcacctacag ggtggtgtcc gtgctgaccg tgctgcacca ggactggctg    1020
aacggcaagg agtacaagtg caaggtctcc aacaaggccc tgccagcccc catcgagaaa    1080
accatcagca aggccaaggg ccagccacgg gagccccagg tgtacaccct gcccccagc     1140
cgggacgagc tgaccaagaa ccaggtgtcc ctgacctgcc tggtgaaggg cttctacccc    1200
agcgacatcg ccgtggagtg ggagagcaac ggccagcccg agaacaacta caagaccacc    1260
cccccagtgc tggacagcga cggcagcttc ttcctgtaca gcaagctgac cgtggacaag    1320
agcaggtggc agcagggcaa cgtgttcagc tgcagcgtga tgcacgaggc cctgcacaac    1380
cactacaccc agaagagcct gagcctgtcc cccggcaagt ga                       1422
```

<210> SEQ ID NO 64
<211> LENGTH: 25
<212> TYPE: PRT
<213> ORGANISM: Homo sapiens

<400> SEQUENCE: 64

Pro Ser Val Ile Trp Glu Ala Lys Cys Arg His Leu Gly Cys Ile Asn
1               5                   10                  15

Ala Asp Gly Asn Val Asp Tyr His Met
            20                  25

<210> SEQ ID NO 65
<211> LENGTH: 12
<212> TYPE: PRT
<213> ORGANISM: Homo sapiens -continued

```
<400> SEQUENCE: 65

Leu Gly Cys Ile Asn Ala Asp Gly Asn Val Asp Tyr
1               5                   10
```

ANTIBODIES TO IL-17A

The present application claims the benefit of U.S. Provisional Patent Application No. 60/837,197, filed Aug. 11, 2006, which is incorporated by reference.

FIELD OF THE INVENTION

The present invention relates generally to IL-17A specific binding compounds such as antibodies, and uses thereof. More specifically, the invention relates to chimeric and humanized antibodies that recognize human IL-17A and modulate its activity, particularly in inflammatory, autoimmune and proliferative disorders.

BACKGROUND OF THE INVENTION

The immune system functions to protect individuals from infective agents, e.g., bacteria, multi-cellular organisms, and viruses, as well as from cancers. This system includes several types of lymphoid and myeloid cells such as monocytes, macrophages, dendritic cells (DCs), eosinophils, T cells, B cells, and neutrophils. These lymphoid and myeloid cells often produce signaling proteins known as cytokines. The immune response includes inflammation, i.e., the accumulation of immune cells systemically or in a particular location of the body. In response to an infective agent or foreign substance, immune cells secrete cytokines which, in turn, modulate immune cell proliferation, development, differentiation, or migration. Immune response can produce pathological consequences, e.g., when it involves excessive inflammation, as in the autoimmune disorders (see, e.g., Abbas et al. (eds.) (2000) *Cellular and Molecular Immunology*, W.B. Saunders Co., Philadelphia, Pa.; Oppenheim and Feldmann (eds.) (2001) *Cytokine Reference*, Academic Press, San Diego, Calif.; von Andrian and Mackay (2000) *New Engl. J. Med.* 343:1020-1034; Davidson and Diamond (2001) *New Engl. J. Med.* 345:340-350).

Interleukin-17A (IL-17A; also known as Cytotoxic T-Lymphocyte-associated Antigen 8 (CTLA8), IL-17) is a homodimeric cytokine produced by memory T cells following antigen recognition. The development of such T cells is promoted by interleukin-23 (IL-23). McKenzie et al. (2006) *Trends Immunol.* 27(1):17-23; Langrish et al. (2005) *J. Exp. Med.* 201(2):233-40. IL-17A acts through two receptors, IL-17 and IL-17RC to induce the production of numerous molecules involved in neutrophil biology, inflammation, and organ destruction. This cytokine synergizes with tissue necrosis factor (TNF) and or interleukin 1β (IL-1β) 1β) to promote a greater pro-inflammatory environment. Antagonizing the activity of IL-17A with antibodies or antigen binding fragments of antibodies has been proposed for the treatment of a variety of inflammatory, immune and proliferative disorders, including rheumatoid arthritis (RA), osteoarthritis, rheumatoid arthritis osteoporosis, inflammatory fibrosis (e.g., scleroderma, lung fibrosis, and cirrhosis), gingivitis, periodontitis or other inflammatory periodontal diseases inflammatory bowel disorders (e.g. Crohn's disease, ulcerative colitis and inflammatory bowel disease), asthma (including allergic asthma), allergies, chronic obstructive pulmonary disease (COPD), multiple sclerosis, psoriasis and cancer. (See, e.g., US 2003/0166862, WO 2005/108616, WO 2005/051422, and WO 2006/013107).

The most significant limitation in using antibodies as a therapeutic agent in vivo is the immunogenicity of the antibodies, As most monoclonal antibodies are derived from rodents, repeated use in humans results in the generation of an immune response against the therapeutic antibody, e.g., human against mouse antibodies or HAMA. Such an immune response results in a loss of therapeutic efficacy at a minimum and a potential fatal anaphylactic response at a maximum. Initial efforts to reduce the immunogenicity of rodent antibodies involved the production of chimeric antibodies, in which mouse variable regions (Fv) were fused with human constant regions. Liu et al. (1987) *Proc. Natl. Acad. Sci. USA* 84:3439-43. However, mice injected with hybrids of human variable regions and mouse constant regions develop a strong anti-antibody response directed against the human variable region, suggesting that he retention of the entire rodent Fv region in such chimeric antibodies may still result in unwanted immunogenicity in patients.

It is generally believed that complementarity determining region (CDR) loops of variable domains comprise the binding site of antibody molecules. Therefore, the grafting of rodent CDR loops onto human frameworks (i.e., humanization has been attempted to further minimize rodent sequences. Jones et al. (1986) *Nature* 321:522; Verhoeyen et al. (1988) *Science* 239:1534. However, CDR loop exchanges still do not uniformly result in an antibody with the same binding properties as the antibody of origin. Changes in framework residues (TR), residues involved in CDR loop support, in humanized antibodies also are often required to preserve antigen binding affinity. Kabat et al. (1991) *J. Immunol.* 147:1709. While the use of CDR grafting and framework residue preservation in a number of humanized antibody constructs has been reported, it is difficult to predict if a particular sequence will result in the antibody with the desired binding, and sometimes biological, properties. See, e.g., Queen et al. (1989) *Proc. Natl. Acad. Sci. USA* 86:10029, Gorman et al. (1991) *Proc. Natl. Acad. Sci. USA* 88:4181, and Hodgson (1991) *Biotechnology (NY)* 9:421-5. Moreover, most prior studies used different human sequences for animal light and heavy variable sequences, rendering the predictive nature of such studies questionable. Sequences of known antibodies have been used or, more typically, those of antibodies having known X-ray crystal structures, such as antibodies NEW and KOL, See, e.g., Jones et al., supra; Verhoeyen et al., supra; and Gorman et al., supra. Exact sequence information has been reported for a few humanized constructs.

The need exists for antagonists of IL-17A, such as anti-IL-17A monoclonal antibodies, for use in treatment of human disorders, such as inflammatory, autoimmune, and proliferative disorders. Such antagonists will preferably exhibit low immunogenicity in human subjects, allowing for repeated administration without adverse immune responses.

SUMMARY OF THE INVENTION

The present invention relates to anti-human IL-17A antibodies having one or more desirable properties, including high binding affinities, neutralizing activities, good pharmacokinetics and low antigenicity in human subjects. The invention also relates to use of the antibodies of the present invention in the treatment of disease.

Accordingly, in one embodiment the present invention provides a binding compound, for example an antibody molecule or binding fragment thereof, which binds human IL-17A and inhibits its activity. In some embodiments, the binding compound comprises at least one antibody light chain variable ($V_L$) domain and at least one antibody heavy chain variable ($V_H$) domain, or binding fragments of these domains, wherein the $V_L$ domain comprises at least a specified number of complementarity determining regions (CDRs) having a sequence selected from SEQ ID NOs: 11-13, and the $V_H$ domain comprises at least at least a specified number of CDRs having a sequence selected from SEQ ID NOs:14-20, wherein the specified number is one, two or three. The specified number of CDRs may be the same or different for the light and heavy chain variable domains in any given binding compound. In another embodiment, the VL domain CDRs are selected from SEQ ID NOs:14, 17 and 20. In yet another embodiment, the V$_H$ domain CDRs are selected from SEQ ID NOs:14, 16 and 19. In a further embodiment, the sequences of the V$_L$ and V$_H$ domains are the sequences of SEQ ID NOs: 5 and 6, respectively. In some embodiments, the IL-17A binding compound inhibits the activity of human IL-17A.

In other embodiments, the binding compound comprises at least one V$_L$ domain and at least one V$_H$ domain, or binding fragments of these domains, wherein the V$_L$ domain comprises one, two or three CDRs having a sequence selected from SEQ ID NOs: 26-28, and the V$_H$ domain comprises one, two or three CDRs having a sequence selected from SEQ ID NOs: 29-31. In another embodiment the sequence of the V$_L$ and V$_H$ domains are the sequences of SEQ ID NOs: 22 and 23, respectively. In another embodiment, the binding compound has the same CDRs as the antibody produced from the hybridoma having ATCC Accession No. PTA-7739 (rat 30C10, deposited as strain JL7-30C10.C3 on Jul. 20, 2006).

In a further embodiment, the binding compound comprises at least one V$_L$ domain and at least one V$_H$ domain, or binding fragments of these domains, wherein the V$_L$ domain comprises one, two or three CDRs having a sequence selected from SEQ ID NOs: 48-50, and the V$_H$ domain comprises one, two or three CDRs having a sequence selected from SEQ ID NOs: 51-53.

In yet other embodiments, the binding compound comprises at least one V$_L$ domain and at least one V$_H$ domain, or binding fragments of these domains, wherein the V$_L$ domain comprises one, two or three CDRs having a sequence selected from SEQ ID NOs: 34-36, and the V$_H$ domain comprises one, two or three CDRs having a sequence selected from SEQ ID NOs: 37-39, or the V$_L$ domain comprises one, two or three CDRs having a sequence selected from SEQ ID NOs: 56-58, and the V$_H$ domain comprises one, two or three CDRs having a sequence selected from SEQ ID NOs: 59-61.

In various other embodiments, the present invention provides a binding. compound that binds to human IL-17A that has V$_L$ and V$_H$ domains with at least 95%, 90%. 85%, 80%, 75% or 50% sequence homology with the sequences of SEQ ID NOs: 5 and 6, respectively. In other embodiments the binding compound of the present invention comprises V$_L$ and V$_H$ domains having up to 0, 1, 2, 3, 4, 5, 6, 7, 8, 9, 10 or more conservative amino acid substitutions with reference to the sequences of SEQ ID NOs. 5 and 6, respectively. In another embodiment, the binding compound of the present invention is an antibody having a light chain and a heavy chain with up to 0, 1, 2, 3, 4, 5, 6, 7, 8, 9, 10 or more conservative amino acid substitutions with reference to the mature forms of the sequences of SEQ ID NOs: 2 and 4, respectively.

In one embodiment, the binding compound is an antibody or binding fragment thereof, e.g. an antibody fragment selected from the group consisting of Fab, Fab', Fab'-SH, Fv, scFv, F(ab')$_2$, and a diabody. In one embodiment, the binding compound of the present invention is antibody hu16C10 comprising a light chain having the sequence of the mature form of SEQ ID NO.: 2 (residues 1-220) and a heavy chain having the sequence of the mature form of SEQ ID NO.: 4 (residues 1-454). In another embodiment, the binding compound is the antibody produced from the expression vector having ATCC Accession No. PTA-7675 (hu16C10 in plasmid pAIL17AV1, deposited Jun. 28, 2006).

In one embodiment, the binding compound of the present invention comprises a heavy chain constant region, for example a human constant region, such as γ1, γ2, γ3, or γ4 human heavy chain constant region or a variant thereof. In another embodiment, the binding compound comprises a light chain constant region, for example a human light chain constant region, such as lambda or kappa human light chain region or variant thereof.

In another embodiment, the invention relates to an isolated nucleic acid, for example DNA, encoding a binding compound of the present invention, for example an antibody (or binding fragment thereof) that binds to human IL-17A. In one embodiment, the isolated nucleic acid encodes a binding compound comprising at least one antibody light chain variable (V$_L$) domain and at least one antibody heavy chain variable (V$_H$) domain, or binding fragments of these domains, wherein the V$_L$ domain comprises at least a specified number of complementarity determining regions (CDRs) having a sequence selected from SEQ ID NOs: 11-13, and the Via domain comprises at least at least a specified number of CDRs having a sequence selected from SEQ ID NOs: 14-20, wherein the specified number is one, two or three.

In another embodiment, the isolated nucleic acid encodes one or both of the light and heavy chain variable region sequences of SEQ ID NOs:5 and 6, respectively. n yet another embodiment, the isolated nucleic acid encodes antibody 16C10 comprising a light chain having the sequence of the mature form of SEQ ID NO.: 2 and a heavy chain having the sequence of the mature form of SEQ ID NO:4. In some embodiments, the isolated nucleic acid comprises nucleotides 58-717 of SEQ ID NO:1 or SEQ ID NO:62 and in other embodiments the isolated nucleic acid comprises nucleotides 58-1419 of SEQ ID NO:3 or SEQ ID NO:63. In yet another embodiment, the isolated nucleic acid comprises the sequence of SEQ ED NO:1 and the sequence of SEQ ID NO:3. In still yet another embodiment, the isolated nucleic acid comprises the sequence of SEQ ID NO:62 and the sequence of SEQ ID NO:63. In some embodiments, the isolated nucleic acid encodes both a light chain and a heavy chain on a single nucleic acid molecule, and in other embodiments the light and heavy chains are encoded on two or more separate nucleic acid molecules.

In futher embodiments, the present invention relates to expression vectors comprising the isolated nucleic acids of the invention, wherein the nucleic acid is operably linked to control sequences that are recognized by a host cell when the host cell is transfected with the vector. In one embodiment, the expression vector has ATCC Accession No. PTA-7576 (hu16C10 in plasmid pAIL17AV1, deposited Jun. 28, 2006).

In another embodiment, the invention relates to a host cell comprising an expression vector of the present invention. The invention further relates to methods of producing a binding compound of the present invention comprising culturing a host cell harboring an expression vector encoding the binding compound in culture medium, and isolating the binding compound from the host cell or culture medium.

The invention also relates to binding compounds, such as antibodies or binding fragments thereof, that bind to the same epitope on human IL-17A as antibodies 16C10, 4C3, 30C10C, 12E6, 23E12 or 1D10; for example, antibodies that are able to cross-block binding of any of these antibodies of the present invention, or antibodies that bind within the epitope defined by amino acid residues 74-85 of human IL-17A (SEQ ID NO.: 40).

The invention also relates to high affinity human IL-17A binding compounds, such as antibodies or binding fragments thereof, such as binding compounds that bind with equilibrium dissociation constants ($K_d$) of 1000, 500, 100, 50, 20, 10, 5, 2 pM or less (i.e. higher affinity). The invention also relates to binding compounds that have potent biological activity, such as an $IC_{50}$ of 5000, 2000, 1000, 500 pM when measured in a biological activity assay where IL-17A stimulation is effected at a concentration of 1000 pM (1 nM), such as IL-17A-stimulated production of IL-6 from normal human dermal fibroblasts, foreskin fibroblasts, or synoviocytes. The invention also relates to binding compounds that have an $IC_{50}$ of 1000, 500, 200, 100, 50 pM or less when measured in a biological activity assay where the IL-17A stimulation is effected at a concentration of 100 pM, such as the Ba/F3-hIL-17Rc-mGCSFR proliferation assay. In general, the invention relates to binding compounds that are able to inhibit the activity of human IL-17A in biological assays at concentrations that range from 10×, 5×, 2×, 1× and as low as 0.5× the concentration of IL-17A, when the concentration of IL-17A is, e.g., 5, 10, 50, 100, 500 or 1000 pM or higher.

The invention also relates to binding compounds that are able to reduce IL-17A induced neutrophil recruitment to the lung by 50% or more when administered to mice to give a serum concentration of binding compound of 50, 40, 30, 20 µg/ml or lower.

In one embodiment, the binding compound binds to cynomolgus monkey IL-17A with an affinity ($K_d$) that is no more than 5, 10, or 20-fold lower than its affinity for human IL-17A. In another embodiment, the binding compound binds to human IL-17A with an affinity ($K_d$) that is 100, 500, 1000 or 2000-fold higher than its affinity for mouse or rat IL-17A.

The invention also relates to methods of treating subjects, including human subjects, in need of treatment with the human IL-17A-binding compounds of the present invention. Such subjects may have an inflammatory or autoimmune disorder, such as rheumatoid arthritis, inflammatory bowel disease, psoriasis, multiple sclerosis, chronic obstructive pulmonary disease, cystic fibrosis, systemic scleroderma, allograft rejection, autoimmune myocarditis or peritoneal adhesions. Such methods of treatment may further comprise administering one or more additional therapeutic agents, such as immunosuppressive or anti-inflammatory agents. In one embodiment, the subject has been diagnosed with an IL-71 A-mediated disease. In another embodiment, the subject has been diagnosed with rheumatoid arthritis. In yet another embodiment, the subject has been diagnosed with multiple sclerosis.

In a further embodiment, the invention provides methods of treatment comprising administration of a therapeutically effective amount of an anti-human IL-17A antibody or binding fragment in combination with one or more other therapeutic agents In one embodiment the other therapeutic agent is an anti-human TI-23 antibody, or binding fragment thereof. In various embodiments the anti-human IL-23 antibody or fragment is administered before, concurrently with, or after the anti-human IL-17A antibody or fragment. In one embodiment the anti IL-17A and anti IL-23 antibodies are administered together for a limited time during the acute phase of an adverse immunologic event, after which treatment with anti-IL-17A antibody is discontinued but treatment with anti IL-23 antibody is continued. In other embodiments, the one or more other agent comprises an antagonist of IL-1β, IL-6 or TGF-β, for example an anti-IL-6 or an anti-TGF-β antibody, or a combination of such antagonists.

The invention also relates to compositions and formulations of the binding compounds of the present invention, comprising the binding compound and a pharmaceutically acceptable carrier or diluent, and optionally one or more immunosuppressive or anti-inflammatory agents.

BRIEF DESCRIPTION OF THE DRAWINGS

FIG. 1A shows alignments of the light chain variable domains of several anti-human IL-17A antibodies according to the present invention. Rat 16C10C $V_L$=SEQ ID NO: 7; hum 16C10 $V_L$=SEQ ID NO: 5; rat 4C3 $V_L$=SEQ ID NO. 21; hum 4C3 $V_L$=SEQ ID NO: 5; rat 23E12 $V_L$=SEQ ID NO: 45; rat 30C10 $V_L$=SEQ ID NO: 24; hum 30C10 $V_L$=SEQ ID NO: 22; rat 12E6 $V_L$=SEQ ID NO: 32; rat 1D10 $V_L$=SEQ ID NO: 54. CDRs are indicated (and are provided at Table 3). Numbering is according to Kabat et al. (1991) "Sequences of Proteins of Immunological Interest", U.S. Department of Health and Human Services, NIH Pub. 91-3242, 5th Ed., referred to herein as "Kabat et al. (1991)".

FIG. 1B shows alignments of the heavy chain variable domains of several anti-human IL-17A antibodies according to the present invention. Rat 16C10 $V_H$=SEQ ID NO: 8; hum 16C10C $V_H$=SEQ ID NO: 6; rat 4C3 $V_H$=SEQ ID NO: 8; hum 4C3 $V_H$=SEQ ID NO: 6; rat 23E12 $V_H$=SEQ ID NO: 47; rat 30C10 $V_H$=SEQ ID NO: 25; hum 30C10 $V_H$=SEQ ID NO: 23; rat 12E6 $V_H$=SEQ ID NO: 33; rat 1D10 $V_H$=SEQ ID NO: 55. CDRs are indicated (and are provided at Table 4). Numbering is according to Kabat et al. (1991).

FIG. 2A shows the amino acid sequence of the light chain of humanized anti-IL-17 antibody 16C10 according to the present invention (the mature form of SEQ ID NO: 2 i.e. residues 1-220) CDRs are indicated.

FIG. 2B shows the amino acid sequence for the heavy chain of humanized anti-IL-17A antibody 16C10 according to the present invention (the mature form of SEQ ID NO: 4, i.e. residues 1-454). CDRs are indicated.

FIG. 3A presents visual disease severity score (DSS), a measure of visual paw swelling and redness, as a function of antibody treatment. Scoring is: 0=paw appears the same as control (untreated) paw; 1=inflammation of one finger on a given paw; 2=inflammation of two fingers or the palm of a given paw; 3=inflammation of the palm and finger(s) of a given paw.

FIG. 3B presents cartilage damage (by histopathology) as a function of antibody treatment. Scoring is: 0=normal; 1=minimal, 2=mild; 3=moderate; 4=severe.

FIG. 3C presents bone erosion (by histopathology) as a function of antibody treatment. Scoring is: 0=normal; 1=minimal, 2=mild; 3=moderate; 4=severe.

FIG. 3D presents bone erosion (by histopathology) for paws from CIA mice that scored 2 or 3 in visual DSS, i.e. highly inflamed paws. rIgG1 is an isotype control antibody. Scoring is: 0=normal; 1=minimal, 2=mild; 3=moderate; 4=severe.

FIG. 5A shows a nucleotide sequence (SEQ ID NO:62) encoding the light chain of humanized anti-IL-17A antibody 16C10.

FIG. 5B shows a nucleotide sequence encoding the heavy chain of humanized anti-IL-17A antibody 16C10 (SEQ ID NO:63).

DETAILED DESCRIPTION

I. Definitions

Figure 3A:
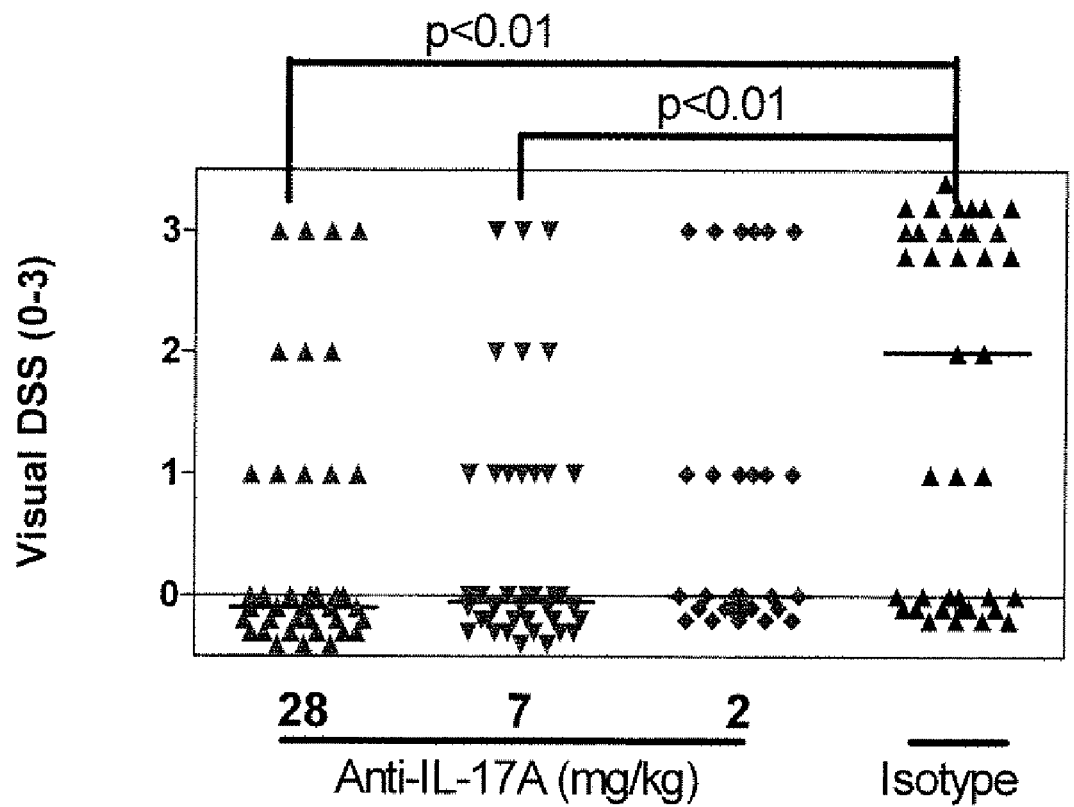
FIGS. 3A-3D shows the effects of anti-IL-17A antibody treatments on pathology in the CIA mouse model of rheumatoid arthritis. Treatments include administration of anti-IL-17A antibody 1D10 (at 28$ 7, and 2 mg/kg) and administration of an isotype control (7 mg/g).
Figure 3B:
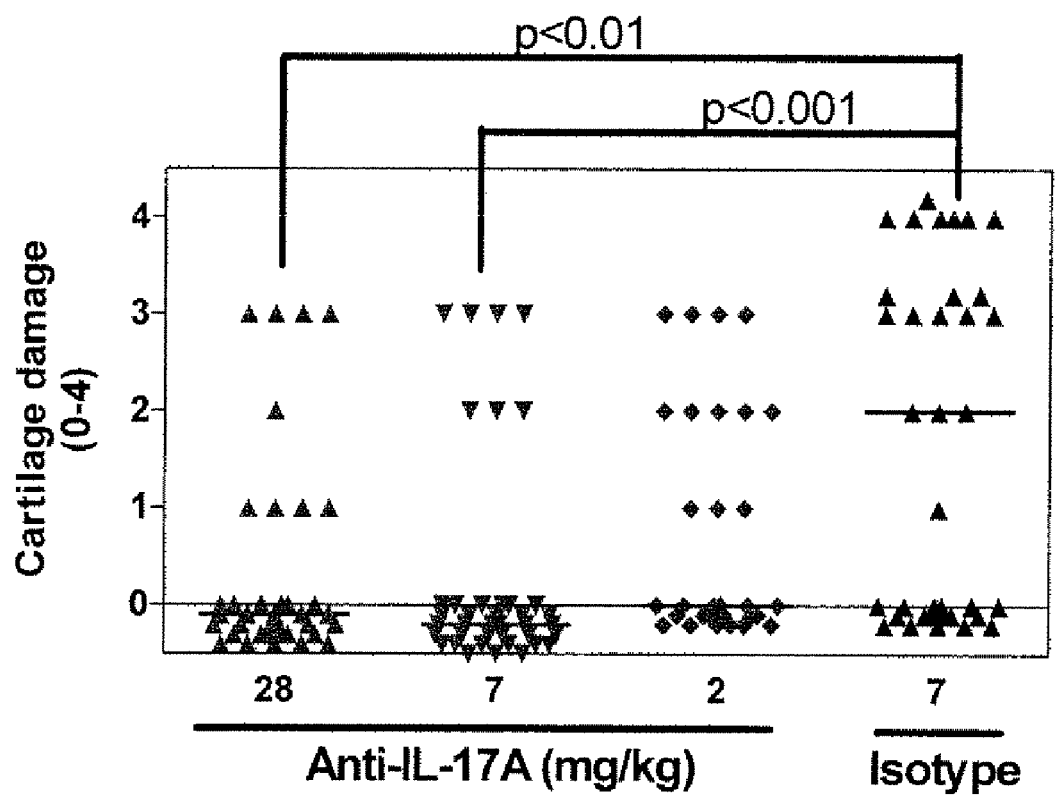

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g. of a cell, by a reagent, diagnostic, binding compound, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of an IL-17A agonist or IL-17A antagonist to a human or animal subject, a cell, tissue, physiological compartment, or physiological fluid. "Treatment of a cell" also encompasses situations where the IL-17A agonist or IL-17A antagonist contacts IL-17A receptor, e.g., in the fluid phase or colloidal phase, but also situations where the agonist or antagonist does not contact the cell or the receptor.

"Treat" or "treating" means to administer a therapeutic agent, such as a composition containing any of the binding compounds of the present invention, internally or externally to a patient having one or more disease symptoms for which the agent has known therapeutic activity. Typically, the agent is administered in an amount effective to alleviate one or more disease symptoms in the treated patient or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age and weight of the patient, and the ability of the drug to elicit a desired response in the patient. Whether a disease symptom has been alleviated can be assessed by any clinical measurement typically used by physicians or other skilled healthcare providers to assess the severity or progression status of that symptom While an embodiment of the present invention (e.g., a treatment method or article of manufacture) may not be effective in alleviating the target disease symptom(s) in every patient, it should alleviate the target disease symptom(s) in a statistically significant number of patients as determined by any statistical test known in the art such as the Student's t-test, the chi$^2$-test, the U-test according to Mann and Whitney, the Kruskal-Wallis test (H-test), Jonckheere-Terpstra-lest and the Wilcoxon-test.

Four variants of human IL-17A protein are referred to herein. i) As used herein, the terms "human IL-17A" and "native human IL-17A" ("huIL-17A" and "humIL-17A") refer to the mature forms (i.e. residues 24-155) of human IL-17A protein accession numbers NP_002181 and AAT22064, and naturally occurring variants and polymorphisms thereof. ii) As used herein, the term "rhIL-17A" refers to a recombinant derivative of native human IL-17A in which two additional amino acids (LE) are appended at the N-terminus of the mature form of native human IL-17A. This nomenclature is adopted for convenience in referring to various forms of IL-17A, and may not match usage in the literature. iii) As used herein, the term "FLAG-huIL-17A" refers to a variant of native human IL-17A having an N-terminal FLAG® peptide tag appended. In some experiments the FLAG-huIL-17A is biotinylated. iv) R&D Systems human IL-17A referred to herein is residues 20-155 of human IL-17A protein accession numbers NP_002181 and AAT22064, with an additional N-terminal methionine. Table 1 is a summary of the variant N-termini of the IL-17A molecules referenced herein.

TABLE 1

Variant Forms of Human IL-17A

| IL-17A Variant | Sequence (N→C) | SEQ ID NO: |
|---|---|---|
| huIL-17A (native) | GITIPRN . . . VHHVA | 40 |
| rhIL-17A | LEGITIPRN . . . VHHVA | 41 |
| FLAG-huIL-17A | DYKDDDDKLGITIPRN . . . VHHVA | 42 |
| R&D IL-17A | MIVKAGITIPRN . . . VHHVA | 43 |

Unless otherwise noted, any IL-17A used in the experiments described herein that is produced using adenoviral vectors is rhIL-17A. The term "IL-17A" refers to generally to human IL-17A, native or recombinant, and non-human homologs of human II-17A, Unless otherwise indicated, molar concentrations of IL-17A are calculated using the molecular weight of a homodimer of IL-17A (e.g., 30 kDa for human IL-17A).

As used herein, the term "antibody" refers to any form of antibody that exhibits the desired biological activity. Thus, it is used in the broadest sense and specifically covers, but is not limited to, monoclonal antibodies (including full length monoclonal antibodies), polyclonal antibodies, multispecific antibodies (e.g., bispecific antibodies). As used herein, the terms "IL-17A binding fragment or "binding fragment" of an antibody (the "parental antibody") encompass a fragment or a derivative of an antibody, typically including at least a portion of the antigen binding or variable regions (e.g. one or more CDRs) of the parental antibody, that retains at least some of the binding specificity of the parental antibody. Examples of antibody binding fragments include, but are not limited to, Fab, Fab', F(ab')$_2$, and Fv fragments; diabodies; linear antibodies; single-chain antibody molecules, e.g., sc-Fv; and multispecific antibodies formed from antibody fragments. Typically, a binding fragment or derivative retains at least 10% of its IL-17A binding activity when that activity is expressed on a molar basis. Preferably, a binding fragment or derivative retains at least 20%, 50%, 70%/, 80%, 90%, 95% or 100% or more of the IL-17A. binding affinity as the parental antibody. It is also intended that an IL-17A binding fragment can include conservative amino acid substitutions (referred to as "conservative variants" of the antibody) that do not substantially alter its biologic activity. The term "binding compound" refers to both antibodies and binding fragments thereof.

A "Fab' fragment" is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H1$ and $C_H2$ domains of an antibody. The two heavy chain fragments are held together by two or more disulfide bonds and by hydrophobic interactions of the $C_H3$ domains.

A "Tab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains.

The "Fv region" comprises the variable regions from both the heavy and light chains, but lacks the constant regions.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 13, Rosenburg and Moore eds. Springer-Verlag, New York, pp. 269-315. See also, International Patent Application Publication No. WO 88101649 and U.S. Pat. Nos. 4,946,778 and 5,260,203.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may he bispecific (see below).

As used herein, unless otherwise indicated, an "anti-IL-17A" antibody refers to an antibody that is raised against human IL-17A or a variant thereof, such as huIL-17A, rhIL-17A, FLAG-huIL-17A and R&D IL-17A, or any antigenic fragment thereof.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., (1984) *Proc. Natl. Acad. Sci. USA* 81: 6851-6855).

As used herein, a "chimeric antibody" is an antibody having the variable domain from a first antibody and constant domain from a second antibody, where the first and second antibodies are from different species. Typically the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental rodent antibody.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94104678; WO 94/25591; U.S. Pat. No. 6,005,079, which are hereby incorporated by reference in their entireties). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fe).

The antibodies of the present invention also include antibodies with modified (or blocked) Fe regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fe region include amino acid changes (substitutions, deletions and insertions), glycosylation or deglycosylation, and adding multiple Fe. Changes to the Fe can also alter the half-life of antibodies in therapeutic antibodies, enabling less frequent dosing and thus increased convenience ad decreased use of material. See Presta (2005) *J. Allergy Clin. Immunol.* 116:731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody that comprises mouse immunoglobulin sequences only. Alternatively, a fully human antibody may contain rat carbohydrate chains if produced in a rat, in a rat cell, or in a hybridoma derived from a rat cell. Similarly, "rat antibody" refers to an antibody that comprises rat immunoglobulin sequences only.

As used herein, the term "hypervariable region" refers to the amino acid residues of an antibody which are responsible for antigen-binding. The hypervariable region comprises amino acid residues from a "complementarity determining region" or "CDR" (i.e. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al. (1991) Sequences of Proteins of Immunological Interest, 5th Ed. Public Health Service, National Institutes of Health, Bethesda, Md.) and/or those residues from a "hypervariable loop" (i.e. residues 26-32 (CDRL1), 50-52 (CDRL2) and 91-96 (CDRL3) in the light chain variable domain and 26-32 (CDRH1), 53-55 (CDRH2) and 96-101 (CDRH3) in the heavy chain variable domain; Chothia and Lesk (1987) *J. Mol. Biol.* 196: 901-917). As used herein, the term "framework" or "FR" residues refers to those variable domain residues other than the hypervariable region residues defined herein as CDR residues.

"Binding substance" refers to a molecule, small molecule, macromolecule, antibody, a fragment or analogue thereof, or soluble receptor, capable of binding to a target. "Binding substance" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, that is capable of binding to a target. "Binding substance" may also refer to a molecule capable of binding to a target in combination with a stabilizer, excipient, salt, buffer, solvent, or additive. "Binding" may be defined as an association of the binding substance with a target where the association results in reduction in the normal Brownian motion of the binding substance, in cases where the binding substance can be dissolved or suspended in solution.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et at (1987) *Molecular Biology of the Gene*, The Benjamin/Cummings Pub. Co., p. 224 (4th Ed.)). In addition, substitutions of structurally or functionally similar amino acids are less likely to disrupt biological activity. Various embodiments of the binding compounds of the present invention comprise polypeptide chains with sequences that include up to 0 (no changes), 1, 2, 3, 4, 5, 6, 7, 8, 9, 10, 12, 15, 20 or more conservative amino acid substitutions when compared with the specific amino acid sequences disclosed herein, e.g. SEQ ID NOs: 2, 4, 5, or 6. As used herein, the phrase "up to X" conservative amino acid substitutions includes 0 substitutions and any number of substitutions up to and including X substitutions. Such exemplary substitutions are preferably made in accordance with those set forth in Table 2 as follows:

TABLE 2

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

The terms "consists essentially of," or variations such as "consist essentially of" or "consisting essentially of" as used throughout the specification and claims, indicate the inclusion of any recited elements or group of elements, and the optional inclusion of other elements, of similar or different nature than the recited elements, which do not materially change the basic or novel properties of the specified dosage regimen, method, or composition. As a nonlimiting example, a binding compound which consists essentially of a recited amino acid sequence may also include one or more amino acids that do not materially affect the properties of the binding compound.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side affects (see, e.g., U.S. Pat. No. 5,888,530 issued to Netti, et al.). An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject (see, e.g., Maynard, et al. (1996) *A Handbook of SOPs for Good Clinical Practice*, Interpharm Press, Boca Raton, Fla.; Dent (2001) *Good Laboratory and Good Clinical Practice*, Urch Publ., London, UK).

"Exogenous" refers to substances that are produced outside an organism, cell, or human body, depending on the context. "Endogenous" refers to substances that are produced within a cell, organism, or human body, depending on the context.

"Homology" refers to sequence similarity between two polynucleotide sequences or between two polypeptide sequences. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system. "Cancerous condition" includes, e.g., cancer, cancer cells, tumors, angiogenesis, and precancerous conditions such as dysplasia.

"Inflammatory disorder" means a disorder or pathological condition where the pathology results, in whole or in part, from, e.g., a change in number, change in rate of migration, or change in activation, of cells of the immune system. Cells of the immune system include, e.g., T cells, B cells, monocytes or macrophages, antigen presenting cells (APCs), dendritic cells, microglia, NK cells, NKT cells, neutrophils, eosinophils, mast cells, or any other cell specifically associated with the immunology, for example, cytokine-producing endothelial or epithelial cells.

"Isolated binding compound" refers to the purification status of a binding compound and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, "polymerase chain reaction" or "PCR" refers to a procedure or technique in which minute amounts of a specific piece of nucleic acid, RNA and/or DNA, are amplified as described in, e.g., U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) *Cold Spring Harbor Symp. Quant. Biol.* 51:263; Erlich, ed., (1989) PCR TECHNOLOGY (Stockton Press, N.Y.) As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

As used herein, the term "germline sequence" refers to a sequence of unrearranged immunoglobulin DNA sequences. Any suitable source of unrearranged immunoglobulin may be used.

"Inhibitors" and "antagonists," or "activators" and "agonists," refer to inhibitory or activating molecules, respectively, e.g., for the activation of e.g., a ligand, receptor, cofactor, a gene, cell, tissue, or organ. A modulator of, e.g., a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a compound that reduces, blocks, or inactivates a constitutive activity. An "agonist" is a compound that interacts with a target to cause or promote an increase in the activation of the target. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

To examine the extent of inhibition, for example, samples or assays comprising a given, e.g., protein, gene, cell, or organism, are treated with a potential activator or inhibitor and are compared to control samples without the inhibitor. Control samples, i.e., samples not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., indicia of inflammation, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis (see, e.g., Knight (2000) *Ann. Clin. Lab. Sci.* 30:145-158; Hood and Cheresh (2002) *Nature Rev. Cancer* 2:91-100; Timme, et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer, et al. (2001) *Glia* 36:235-243; Stanimirovic and Satoh (2000) *Brain Pathol* 10:113-126).

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least ten times the control.

"Ligand" refers, e.g., to a small molecule, peptide, polypeptide, and membrane associated or membrane-bound molecule, or complex thereof that can act as an agonist or antagonist of a receptor. "Ligand" also encompasses an agent that is not an agonist or antagonist, but that can bind to the receptor. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex."

Where a ligand and receptor are involved in a signaling pathway, the ligand occurs at an upstream position and the receptor occurs at a downstream position of the signaling pathway.

"Small molecule" is defined as a molecule with a molecular weight that is less than 10 kDa, typically less than 2 kDa, preferably less than 1 kDa, and most preferably less than about 500 Da. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins, have been described (see, e.g., Casset, et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos, et al. (2002) *Curr. Med. Chem.* 9:411-420; Monfardini, et al. (2002) *Curr. Pharm. Des.* 8:2185-2199; Domingues, et al. (1999) *Nat. Struct. Biol.* 6:652-656; Sato and Sone (2003) *Biochem. J.* 371:603-608; U.S. Pat. No. 6,326,482 issued to Stewart, et al).

"Specifically" or "selectively" binds, when referring to a ligand/receptor, antibody/antigen, or other binding pair, indicates a binding reaction that is determinative of the presence of the protein in a heterogeneous population of proteins and other biologics. Thus, under designated conditions, a specified ligand binds to a particular receptor and does not bind in a significant amount to other proteins present in the sample. The antibody, or binding compound derived from the antigen-binding site of an antibody, of the contemplated method binds to its antigen, or a variant or mutein thereof, with an affinity that is at least two fold greater, preferably at least ten times greater, more preferably at least 20-times greater, and most preferably at least 100-times greater than the affinity with any other antigen. In a preferred embodiment the antibody will have an affinity that is greater than about $10^9$ $M^{-1}$, as determined, e.g., by Scatchard analysis (Munsen et ad (1980) *Analyt. Biochem.* 107:220-239).

As used herein, the term "immunomodulatory agent" refers to natural or synthetic agents that suppress or modulate an immune response. The immune response can be a humoral or cellular response. Immunomodulatory agents encompass immunosuppressive or anti-inflammatory agents.

"Immunosuppressive agents", "immunosuppressive drugs", or "immunosuppressants" as used herein are therapeutics that are used in immunosuppressive therapy to inhibit or prevent activity of the immune system. Clinically they are used to prevent the rejection of transplanted organs and tissues (e.g. bone marrow, heart, kidney, liver), and/or in the treatment of autoimmune diseases or diseases that are most likely of autoimmune origin (e.g. rheumatoid arthritis, myasthenia gravis, systemic lupus erythematosus, ulcerative colitis, multiple sclerosis). Immunosuppressive drugs can be classified as. glucocorticoids; cytostatics; antibodies (biological response modifiers); drugs acting on immunophilins; other drugs, including known chemotherapeutic agents used in the treatment of proliferative disorders. For multiple sclerosis, in particular, the antibodies of the present invention can be administered in conjunction with a new class of myelin binding protein-like therapeutics, known as copaxones.

"Anti-inflammatory agents" or "antiinflammatory drugs" refer to both steroidal and non-steroidal therapeutics. Steroids, also known as corticosteroids, are drugs that closely resemble cortisol, a hormone produced naturally by adrenal glands. Steroids are used as the main treatment for certain inflammatory conditions, such as: systemic vasculitis (inflammation of blood vessels); and myositis (inflammation of muscle). Steroids might also be used selectively to treat inflammatory conditions such as: rheumatoid arthritis (chronic inflammatory arthritis occurring in joints on both sides of the body); systemic lupus erythematosus (a generalized disease caused by abnormal immune system function); Sjögren's syndrome (chronic disorder that causes dry eyes and a dry mouth).

Non-steroidal anti-inflammatory drugs, usually abbreviated to NSAIDs, are drugs with analgesic, antipyretic and anti-inflammatory effects—they reduce pain, fever and inflammation. The term "non-steroidal" is used to distinguish these drugs from steroids, which (amongst a broad range of other effects) have a similar eicosanoid-depressing, anti-inflammatory action. NSAIDs are generally indicated for the symptomatic relief of the following conditions: rheumatoid arthritis; osteoarthritis; inflammatory arthropathies (e.g. ankylosing spondylitis, psoriatic arthritis, Reiter's syndrome); acute gout; dysmenorrhoea; metastatic bone pain; headache and migraine; postoperative pain; mild-to-moderate pain due to inflammation and tissue injury; pyrexia; and renal colic. NSAIDs include salicylates, arlyalknoic acids, 2-arylpropionic acids (profens), N-arylanthranilic acids (fenamic acids), oxicams, coxibs, and sulphonanilides.

Disease-modifying anti-rheumatic drugs (DMARDs) maybe administered, often in combination with NSAIDs. Commonly prescribed DMARDs include hydroxychloroquine/chloroquine, methotrexate, gold therapy, sulfasalazine, and azathioprine.

II. Antibodies Specific for Human L-17A

The present invention provides engineered anti-IL-17A antibodies and uses thereof to treat various inflammatory, immune and proliferative disorders, including rheumatoid arthritis (R), osteoarthritis, rheumatoid arthritis osteoporosis, inflammatory fibrosis (e.g., scleroderma, lung fibrosis, and cirrhosis), inflammatory bowel disorders (e.g., Crohn's disease, ulcerative colitis and inflammatory bowel disease), asthma (including allergic asthma), allergies, COPD, multiple sclerosis, psoriasis and cancer.

Any suitable method for generating monoclonal antibodies may be used to generate the anti-IL-17A antibodies of the present invention. For example, a recipient animal may be immunized with a linked or unlinked (e.g. naturally occurring) form of the IL-17A homodimer, or a fragment thereof. Any suitable method of immunization can be used. Such methods can include adjuvants, other immunostimulants, repeated booster immunizations, and the use of one or more immunization routes.

Any suitable form of IL-17A can be used as the immunogen (antigen) for the generation of the non-human antibody specific for IL-17A, which antibody can be screened for biological activity. The eliciting immunogen may be full-length mature human IL-17A, including linked and naturally occurring homodimers, or peptides thereof encompassing single epitopes or multiple epitopes. The immunogen may be used alone or in combination with one or more immunogenicity enhancing agents known in the art. The immunogen may be purified from a natural source or produced in a genetically modified cell. DNA encoding the immunogen may be genomic or non-genomic (e.g., cDNA) in origin. Immunogen-encoding DNA may be expressed using suitable genetic vectors, including but not limited to adenoviral vectors, adenoassociated viral vectors, baculoviral vectors, plasmids, and non-viral vectors, such as cationic lipids.

Any suitable method can be used to elicit an antibody response with the desired biologic properties, e.g. to inhibit IL-17A binding to its receptor. In some embodiments, antibodies are raised in mammalian hosts such as mice, rodents, primates, humans, etc. Techniques for preparing monoclonal antibodies may be found in, e.g., Stites et al. (eds.) BASIC AND CLINICAL IMMUNOLOGY (4th ed.) Lange Medical Publications, Los Altos, Calif., and references cited therein; Harlow and Lane (1988) ANTIBODIES: A LABORATORY MANUAL CSH Press; Goding (i 986) MONOCLONAL ANTIBODIES: PRINCIPLES AND PRACTICE (2d ed.) Academic Press, New York, N.Y. Thus, monoclonal antibodies may be obtained by a variety of techniques familiar to researchers skilled in the art. Typically, spleen cells from an animal immunized with a desired antigen are immortalized, commonly by fusion with a myeloma cell. See Kohler and Milstein (1976) *Eur. J. Immunol.* 6:511-519. Alternative methods of immortalization include transformation with Epstein Barr Virus, oncogenes, or retroviruses, or other methods known in the art. See, e.g., Doyle et al. (eds.) (1994 and periodic supplements) CELL AND TISSUE CULTURE: LABORATORY PROCEDURES, John Wiley and Sons, New York, NY. Colonies arising from single immortalized cells are screened for production of antibodies of the desired specificity and affinity for the antigen. The yield of monoclonal antibodies produced by such cells may be enhanced by various techniques, including injection into the peritoneal cavity of a vertebrate host.

Other suitable techniques involve selection of libraries of antibodies in phage or similar vectors. See, e.g. Huse et al., *Science* 246:1275-1281 (1989); and Ward et al., *Nature* 341: 544-546 (1989). The antibodies of the present invention may be used without modification, e.g. as the parental rodent antibody, or with modifications to facilitate their use as therapeutic agents in human subjects, such as chimeric or humanized antibodies. In some embodiments, the antibodies will be labeled, covalently or non-covalently, with a substance that provides a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly U.S. Pat. No. 4,816,567; and Queen et al. (1989) *Proc. Nat'l Acad. Sci. USA* 86:10029-10033; or made in transgenic mice, see Mendez et al. (1997) *Nature Genetics* 15:146-156; also see Abgenix and Medarex technologies.

Antibodies against predetermined fragments of IL-17A can be raised by immunization of animals with conjugates of the predetermined fragment of IL-17A with carrier proteins. Monoclonal antibodies are prepared from cells secreting the desired antibody. These antibodies can be screened for binding to normal or defective IL-17A. These monoclonal antibodies will usually bind with at least a $K_d$ of about 1 μM, more usually at least about 300, 30, 10, or 3 nM, preferably at least about 300, 100, 30, 10, 3, or 1 pM. Because of the inverse relationship of $K_d$ values and affinity, references to binding with a given $K_d$ "or less" refers to binding with an affinity that is at least as high as the recited numerical value, i.e. with a $K_d$ that is at least as low as the cited value. Binding affinities may be determined by ELISA (see Examples 5-6, infra), or by Biacore® surface plasmon resonance spectroscopy, KinExA or ECL methods (see Example 7, infra). Suitable non-human antibodies may also be identified using the biological assays described in Examples 8-11 and 16-17, infra.

An exemplary method of producing anti-human IL-17A antibodies of the present invention is described at Example 2.

III. Humanization of IL-17A Specific Antibodies

Any suitable non-human antibody can be used as a source for the hypervariable region of an anti-IL-7A antibody of the present invention. Sources for non-human antibodies include, but are not limited to, rodents (e.g. mouse, rat), Lagomorphs (including rabbits), cows, and nonhuman primates. For the most part humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity and affinity. Furthermore, humanized antibodies may comprise residues that are not found in the recipient antibody or in the donor antibody, such as modifications made to further refine antibody performance of the desired biological activity. For further details, see Jones et al. (1986) *Nature* 321: 522-525; Reichmann et al. (1988) *Nature* 332: 323-329; and Presta (1992) *Curr. Op. Strict. Adol.* 2: 593-596.

Methods for recombinantly engineering and producing antibodies have been described, e.g., by Boss et al. (U.S. Pat. No. 4,816,397), Cabilly et al. (U.S. Pat. No. 4,816,567), Law et al. (European Patent Application Publication No. 438 310) and Winter (European Patent Application Publication No. 239 400).

Amino acid sequence variants of humanized anti-IL-17A antibodies of the present invention may be prepared by introducing appropriate nucleotide changes into the humanized anti-IL-17A antibody DNA, or by peptide synthesis. Any combination of deletion, insertion, and substitution may be made to arrive at the final construct, provided that the final construct possesses the desired characteristics. The amino acid changes also may alter post-translation-al processing of the humanized anti-IL-17A antibody such as changing the number or position of glycosylation sites.

One useful method for identifying residues or regions of a humanized anti-IL-17A antibody that are preferred locations for mutagenesis is called "alanine scanning mutagenesis." Cunningham and Wells (1989) *Science* 244: 1081-1085. A group of target residues is identified (e.g., charged residues such as Arg, Asp, H is, Lys, and Glu) and replaced by a neutral or negatively charged amino acid (most preferably alanine or polyalanine) to alter the interaction of the amino acids with IL-17A. The residues showing functional sensitivity to alanine substitutions are then refined by introducing further amino acid substitutions. In one embodiment, the effect of mutations at a given target codon is determined by alanine scanning or random mutagenesis followed by activity and binding analysis of the resulting humanized anti-IL-17A antibody variants.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include humanized anti-IL-17 antibody with an N-terminal methionyl residue or the antibody fused to an epitope tag. Other variants include the fusion of an enzyme or a polypeptide that increases the serum half-life of an antibody to the N- or C-terminus.

Another type of variant is an amino acid substitution variant. These variants have at least one amino acid residue in the humanized anti-IL-17A antibody molecule removed and a different residue inserted in its place. The sites of greatest interest for substitutional mutagenesis include the hypervariable loops, but FR alterations are also contemplated. Hypervariable region residues or FR residues involved in antigen binding are generally substituted in a relatively conservative manner.

Other amino acid variants of the antibody alter the original glycosylation pattern of the antibody, e.g. by eliminating one or more carbohydrate moieties and/or adding one or more glycosylation sites. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. O-linked glycosylation involves attachment of N-acetylgalactosamine, galactose, or xylose to a hydroxyamino acid, most commonly serine or threonine, although 5-hydroxyproline or 5-hydroxylysine may also be used.

Glycosylation sites can be added to the antibodies of the present invention by inserting one or more of the above-described tripeptide sequences (for N-linked glycosylation sites), or addition of one or more serine or threonine residues (for O-linked glycosylation sites).

Nucleic acid molecules encoding amino acid sequence variants of humanized IL-17A-specific antibody are prepared by a variety of methods known in the art. These methods include, but are not limited to, isolation from a natural source (in the case of naturally occurring amino acid sequence variants), or by oligonucleotide-mediated (or site-directed) mutagenesis, PCR mutagenesis, or cassette mutagenesis.

Ordinarily, amino acid sequence variants of the humanized anti-IL-17A antibody will have an amino acid sequence having at least 50% amino acid sequence identity with the original humanized antibody amino acid sequences of either the heavy or the light chain, preferably at least 70%, 80%, 85%, 90%, and most preferably at least 95%. Identity or homology with respect to this sequence is defined herein as the percentage of amino acid residues in the candidate sequence that are identical with the humanized anti-IL-17A residues when the sequences are optimally aligned (i.e. after aligning the sequences and introducing gaps, if necessary, to achieve the maximum percent sequence identity), and not considering any conservative substitutions as part of the sequence identity. None of N-terminal, C-terminal, or internal extensions, deletions, or insertions into the antibody sequence is considered to affect sequence identity or homology.

The humanized antibody can be selected from any class of immunoglobulins, including IgM, IgG, IgD, IgA, and IgE. In one embodiment, the antibody is an IgG antibody. Any isotype of IgG can be used, including $IgG_1$, $IgG_2$, $IgG_3$, and $IgG_4$. Variants of the IgG isotypes are also contemplated. The humanized antibody may comprise sequences from more than one class or isotype. Optimization of the necessary constant domain sequences to generate the desired biologic activity is readily achieved by screening the antibodies in the biological assays described below in the Examples.

Likewise, either class of light chain can be used in the compounds and methods herein. Specifically, kappa, lambda, or variants thereof are useful in the present compounds and methods.

Any suitable portion of the CDR sequences from the non-human antibody can be used to create the humanized antibodies of the present invention. The CDR sequences may be mutagenized by substitution, insertion or deletion, although such mutations would be minimal because of the need to maintain IL-17A binding affinity and specificity. Typically, at least 75% of the humanized antibody CDR residues will correspond to those of the non-human CDR residues, more often 90%, and most preferably greater than 95%, and frequently 100%.

Any suitable portion of the FR sequences from the human antibody can be used. The FR sequences can be mutagenized by substitution, insertion or deletion of at least one residue such that the FR sequence is distinct from the human and non-human antibody sequence employed. It is contemplated that such mutations would be minimal. Typically, at least 75% of the humanized antibody residues will correspond to those of the human FR residues, more often 90%, and most preferably greater than 95%.

Also contemplated are chimeric antibodies or fragments thereof, so long as they exhibit the desired biological activity (U.S. Pat. No. 4,816,567; and Morrison et al. (1984) *Proc. Natl. Acad Sci. USA* 81: 6851-6855). As noted above, typical chimeric antibodies comprise constant domain sequences from antibodies from one species linked to the variable domain of an antigen-specific antibody obtained from a different species.

The binding compounds of the invention may comprise bispecific antibodies. As used herein, the term "bispecific antibody" refers to an antibody, typically a monoclonal antibody, having binding specificities for at least two different antigenic epitopes. In one embodiment, the epitopes are from the same antigen. in another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) *Nature* 305: 537-39. Alternatively, bispecific antibodies can be prepared using chemical linkage. See, e.g., Brennan, et al. (1985) *Science* 229: 81. Bispecific antibodies include bispecific antibody fragments. See, e.g. Hollinger, et al. (1993) *Proc. Natl. Acad. Sci. U.S.A.* 90: 6444-48, Gruber, et al., *J. Immunol.* 152: 5368 (1994).

An exemplary method of humanizing anti-human IL-17A antibodies of the present invention is described at Example 3.

IV. Characterization of IL-17A Specific Antibodies

The methods described herein were used to generate monoclonal antibodies immunoreactive with human IL-17A, as described in greater detail in Examples 2 and 3. FIGS. 1A and 1B show sequence alignments of the variable regions of the light and heavy chains, respectively, of various anti-IL-17A antibodies of the present invention. CDR regions are indicated, and numbering is according to Kabat et al. (1991).

A plasmid containing the nucleic acid sequences encoding the humanized 16C10 light and heavy chains was deposited pursuant to the Budapest Treaty on Jul. 28, 2006, with American Type Culture Collection (ATCC-Manassas, Va., USA) under Accession Number PTA-7675. Hybridomas expressing antibodies 30C10 and 23E12 were deposited as JL7-30C10.C3 and JL7-23E12.B10, respectively, pursuant to the Budapest Treaty on Jul. 20, 2006, with American Type Culture Collection (ATCC—Manassas, Va., USA) under Accession Numbers PTA-7739 and PTA-7740.

The light and heavy chain CDRs of various humanized antibodies of the present invention are provided at Tables 3 and 4, respectively. h addition, Table 4 provides additional CDRs for $V_H$ of hu16C10 with variable positions at which more than one amino acid can be used.

TABLE 3

Variable Light Chain CDR Sequences

| Antibody | CDRL1 | CDRL2 | CDRL3 |
|---|---|---|---|
| hum 16C10 | KSSQSLLFSENQKNYLA (SEQ ID NO: 11) | WTSTRQS (SEQ ID NO: 12) | QQSYYTPYT (SEQ ID NO: 13) |
| hum 4C3 | KSSQSLLFSENQKNYLA (SEQ ID NO: 11) | WTSTRQS (SEQ ID NO: 12) | QQSYYTPYT (SEQ ID NO: 13) |
| hum 23E12 | QASEDIYSGLA (SEQ ID NO: 48) | GASRLHD (SEQ ID NO: 49) | QQGLKYPPT (SEQ ID NO: 50) |
| hum 30C10 | KSSQSLFWSESHMNYLA (SEQ ID NO: 26) | YASTRQS (SEQ ID NO: 27) | HHHYDSHT (SEQ ID NO: 28) |
| hum 12E6 | RTSQDIGNYLS (SEQ ID NO: 34) | GASNLED (SEQ ID NO: 35) | LQYDKYPNT (SEQ ID NO: 36) |
| rat 1D10 | KASQNINKYLD (SEQ ID NO: 56) | NADNLHT (SEQ ID NO: 57) | LQRESWPYT (SEQ ID NO: 53) | regions of antibodies 16C10/4C3 and 30C10 at SEQ ID NOs: 6 and 23, respectively. These humanized variable domains may be used to create full-length chimeric or humanized antibodies by adding the appropriate constant domain sequences. Other embodiments include various other alterations in the CDR amino acid residues in the 16C10C heavy chain, for example, as illustrated in Table 4. With reference to the residue numbering of FIG. 1B, the alterations described in Table 4 (and in SEQ ID NOs. 17 and 20) are N54A, N54Q, N60A, N60Q, M96L, M96A, M96K, M96F, M100hF, M100hL.

In one embodiment of the present invention, chimeric light and heavy chains of antibody 16C10 are created by appending human constant domains (human kappa light chain and human IgG1 constant domain, respectively) to the C-terminus of the humanized $V_L$ (SEQ ID NO: 5) and $V_H$ regions (SEQ ID NO: 6). Sequences of chimeric 16C10 light and heavy chains are provided at SEQ ID NOs: 9 and 10. In other embodiments, chimeric forms of antibodies 30C10 and 4C3 are created by fusing the same constant domains from chimeric 16C10 to their respective humanized $V_L$ and $V_H$ regions (SEQ ID NOs: 22 and 23 for 30C10; SEQ ID NOs: 5 and 6 for 4C3). The chimeric for of humanized 4C3 would, of course, be identical to the chimeric form of humanized 16C10.

In another embodiment, Fill length humanized antibodies are created by substituting framework residues (i.e. those

TABLE 4

Variable Heavy Chain CDR Sequences

| Antibody | CDRH1 | CDRH2 | CDRH3 |
|---|---|---|---|
| hum 16C10 | GFSLPSHSVS (SEQ ID NO: 14) | IIWNQGGTDYNSAFKS (SEQ ID NO: 16) | NAYITDYYYENYFMDA (SEQ ID NO: 19) |
| hum 16C10 variable | GFSLPSHSVS (SEQ ID NO: 14) | IIWNX$_1$GGTDYX$_2$SAPKS X$_1$ = N, A, Q X$_2$ = N, A, Q (SEQ ID NO: 17) | NX$_3$YITDYYYENYFX$_4$DA X$_3$ = M, L, A, K, F X$_4$ = N, F, L (SEQ ID NO: 20) |
| hum 4C3 | GFSLPSHSVS (SEQ ID NO: 14) | IIWNQGGTDYNSAFKS (SEQ ID NO: 16) | NAYITDYYYENYFMDA (SEQ ID NO: 19) |
| hum 23E12 | GFSLTNNGVT (SEQ ID NO: 51) | EVSSGGSTDYNSALKS (SEQ ID NO: 52) | QEVFTGLLDY (SEQ ID NO: 53) |
| hum 30C10 | GFTFNNYWMT (SEQ ID NO: 29) | SVSNTGSSTYYPASVKG (SEQ ID NO: 30) | EGAYYLDY (SEQ ID NO: 31) |
| hum 12E6 | GFTFRDYYMV (SEQ ID NO: 37) | SISYEGSSIYYGESVKG (SEQ ID NO: 38) | HGFNPFDY (SEQ ID NO: 39) |
| rat 1D10 | GFSLTNYYVH (SEQ ID NO: 59) | GVWNDGDTSYNSVLRS (SEQ ID NO: 60) | EGREGFVGYYVMDA (SEQ ID NO: 61) |

In general the CDRs for the humanized antibodies are identical to the CDRs of the parental rat antibodies, with the exception being CDRH2 and CDRH3 of hum 16C10 and hum 4C3, which each has a single amino acid change from the respective rat CDRs. Although they were obtained as independent clones, parental rat antibodies 16C10 and 4C3 are identical in the sequence of the $V_H$ region and differ in the $V_L$ region only by a framework substitution (isoleucine at position 15 in 16C10 is valine in 4C3). As a result, the CDRs are identical for these two parental rat antibodies, and thus for their humanized forms.

Sequences are provided for humanized $V_L$ regions of antibodies 16C10/4C3 and 30C10C at SEQ ID NOs: 5 and 22, respectively. Sequences are provided for humanized $V_H$ amino acid residues in the variable domain that are not part of a CDR) of the chimeric forms antibodies with human germline framework sequences, as described in more detail in Example 3, The resulting antibodies retain only the CDR sequences from the rat antibodies, with the constant domains and framework sequences replaced by human-derived sequences. Full-length light and heavy chains for humanized antibody 16C10, including signal sequences, are provided at SEQ ID NOs: 2 and 4, respectively. In other embodiments, humanized forms of antibodies 4C3 and 23E12 are created by analogy with the method described for 16C10, i.e. substituting the appropriate human framework sequences into the sequence of the chimeric versions of these antibodies (described supra). See Example 3.

In a further embodiment, the full-length light and heavy chains of the humanized antibodies of the present invention are cloned to have a signal peptide at their N-terminus to facilitate secretion from cells when the antibody is produced. In one embodiment, a 19 amino acid signal sequence is added to both the light and heavy chains of the humanized 16C10 antibody (residues −19 to −1 of SEQ ID NOs: 2 and 4). DNA sequences of the full length light and heavy chains of humanized 16C10, with signal sequence added, are provided at SEQ ID NOs: 1 and 3. Such DNA sequences can be cloned and expressed in any suitable expression vector for production of the humanized antibodies of the present invention. In other embodiments, signal sequences may be added to the light and heavy chains of humanized antibodies 30C10 and 4C3, as described for antibody 16C10. In other embodiments, signal sequence peptides are added that are different than the specific signal sequence provided in SEQ ID NOs: 1-4, depending on the intended method of production of the antibodies, Such signal sequences may be obtained from the scientific literature, for example Choo et al.(2005) "SPdb—a signal peptide database," BMO Bioinformatics 6:249.

In yet other embodiments, different constant domains may be appended to the humanized $V_L$ and $V_H$ regions provided herein. For example, if a particular intended use of an antibody (or fragment) of the present invention were to call for altered effector functions, a heavy chain constant domain other than IgG1 may be used. Although IgG1 antibodies provide for long half-life and for effector functions, such as complement activation and antibody-dependent cellular cytotoxicity, such activities may not be desirable for all uses of the antibody. In such instances an IgG4 constant domain, for example, may be used.

V. Affinity and Biological Activity of Humanized Anti-IL-17A

Antibodies having the characteristics identified herein as being desirable in a humanized anti-IL-17A antibody can be screened for inhibitory biologic activity in vitro, ill vivo, or by measuring binding affinity. To screen for antibodies that bind to the same epitope on human IL-17A bound by an antibody of interest (e.g., those which block binding of the cytokine to its receptor), a routine cross-blocking assay can be performed such as that described in ANTIBODIES, A LABORATORY MANUAL, Cold Spring Harbor Laboratory, Ed Harlow and David Lane (1988). Alternatively, epitope mapping can be performed to determine whether the antibody binds an epitope of interest, e.g., as described in Champe et al. (1995) *J. Biol. Chem.* 270:1388-1394. Antibody affinities (e.g. for human IL-17A) may be determined using standard methods, including those described in Example 7. Preferred humanized antibodies are those which bind human IL-17A with a $K_d$ value of no more than about 100 nM ($1 \times 10^{-7}$ M); preferably no more than about 10 nM; more preferably no more than about 1 nM. Even more preferred are embodiments in which the antibodies have $K_d$ values of no more than about 200 pM ($2 \times 10^{-10}$ M), 100 pM, 50 pM, 20 pM, 10 pM, 5 pM or even 2 pM.

The antibodies, and fragments thereof useful in the present compounds and methods include, but are not limited to, biologically active antibodies and fragments. As used herein, the term "biologically active" refers to an antibody or antibody fragment that is capable of binding the desired the antigenic epitope and directly or indirectly exerting a biologic effect. Typically, these effects result from the failure of IL-17A to bind its receptor. As used herein, the term "specific" refers to the selective binding of the antibody to the target antigen epitope. Antibodies can be tested for specificity of binding by comparing binding to IL-17A to binding to irrelevant antigen or antigen mixture under a given set of conditions. An antibody is considered to be specific if it binds to IL-17A with an affinity at least 10-fold, and preferably 50-fold higher than its affinity for an irrelevant antigen or antigen mixture. An antibody that "specifically binds" to a protein comprising IL-17A (or a fragment thereof) does not bind to proteins that do not comprise the IL-17A-derived sequences, i.e. "specificity" as used herein relates to IL-17A specificity, and not any other sequences that may be present in the protein in question. For example, as used herein, an antibody that "specifically binds" to FLAG-hIL-V17A, which is a fusion protein comprising IL-17A and a FLAG® peptide tag, does not bind to the FLAG® peptide tag alone or when it is fused to a protein other than IL-17A.

The data presented in the Examples below show (e.g. Example 7) that humanized antibody 16C10 (including the N54Q and M96A substitutions relative to the parental rat heavy chain CDRs) has a high affinity for binding to human IL-17A, with a $K_d$ in the 1-10 pM range as determined by KinExA analysis. In vitro activity assays, such as Ba/F3 hIL-17Rc-GCSFR cell proliferation assay (Example 11), normal human dermal fibroblast (NHDF) assay (Example 9), and human rheumatoid arthritis (RA) synoviocyte assay (Example 8) confirm that hu16C10 is a high affinity antibody since the observed IC50 values were typically less than or equal to 50% of the concentration of hIL-17A present in the assay (100 pM, 1000 pM, and 1000 pM in the three assays, respectively). The bivalent character of the antibodies used in the experiments, and the potential for IL-17A dimer formation, make it possible to achieve 50% inhibition of a given concentration of IL-17A with less than 0.5 molar equivalents of antibody. An vivo activity assays, such as administration to mice exhibiting collagen-induced arthritis (Example 16) and BAL neutrophil recruitment assay (Example 17) confirm the activity of several of the anti-L-17A antibodies of the present invention in animals. The in vitro and in vivo activity assays also confirm that humanized antibody 16C10 is a neutralizing antibody, which was not known from the binding experiments alone.

The ability of several of the antibodies of the present invention to bind to cyno IL-17A as well as human IL-17A is advantageous because such a potential therapeutic antibody can be used directly in cynomolgus monkey for toxicology studies, rather than having to develop a separate cyno-specific antibody for such studies. The high affinity of several of the antibodies of the present invention is also advantageous in that may reduce the required dosage in human (and other) subjects, which reduces the likelihood of certain adverse reactions. In addition, the high affinity may reduce the volume that must be administered to a subject and reduce the cost of treatment.

The serum hall-life of hu16C10 was measured in mouse and in cynomolgus monkeys. In cyno, half-life after intravenous (iv) administration was evaluated in a dose ranging study with 0.4, 4.0 and 40 mg/kg dosing. Serum concentrations of drug were measured periodically for 42 days. The half-life for subcutaneous (sc) administration in cyno was determined at 4 mg/kg dosing, which was also followed for 42 days. The half-life in cynomolgus monkeys was 10-19 days iv and 28 days sc as measured by the terminal slope of the drug concentration versus time profile. Certain anomalous datapoints at higher dosings were excluded from the analysis. Similar experiments in mice showed that the hu16C10 antibody had a half-life of 13-25 days iv and 12-22 days sc.

Example 19 describes methods used to determine the epitope bound by an exemplary anti-IL-17A antibody of the present invention (16C10C), i.e. residues in the region of L74-Y85 of human IL-17A (SEQ ID NO.: 40). Since the biological assay data presented herein demonstrate that antibody 16C10C is a high affinity neutralizing antibody, other antibodies that bind to the same epitope may also be expected to be neutralizing antibodies, and perhaps also have high binding affinity. The epitope as determined herein is obtained by functional measurements, rather than structure determinations, and the epitope reported herein may differ in detail from the epitope determined by structural methods. The epitope reported herein includes at least some, but not necessarily all, of the amino acid residues that are important for antibody 16C10 binding. The epitope bound by antibodies of the present invention may also be determined by other methods, such as cross-blocking experiments (see Example 12), or by structural methods such as X-ray crystal structure determination. Additional antibodies binding to the same epitope as antibody 16C10 may be obtained, for example, by screening of antibodies raised against hIL-17A, or by immunization of an animal with a peptide comprising the epitope sequence.

V. Antibody Production

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding he heavy and light chains of the antibody). Many vectors are available. The vector components generally include, but are not limited to, one or more of the following: a signal sequence, an origin of replication, one or more marker genes, an enhancer element, a promoter, and a transcription termination sequence. In one embodiment, both the light and heavy chains of he humanized anti-IL-17A antibody of the present invention are expressed from the same vector, e.g. a plasmid or an adenoviral vector.

Antibodies of the present invention may be produced by any method known in the art. In one embodiment, antibodies are expressed in mammalian or insect cells in culture, such as chinese hamster ovary (CHO) cells, human embryonic kidney (HEK) 293 cells, mouse myeloma NSO cells, baby hamster kidney (BHK) cells, *Spodoptera frugiperda* ovarian (Sf) cells. In one embodiment, antibodies secreted from CHO cells are recovered and purified by standard chromatographic methods, such as protein A, cation exchange, anion exchange, hydrophobic interaction, and hydroxyapatite chromatography. Resulting antibodies are concentrated and stored in 20 mM sodium acetate, pH 5.5.

In another embodiment, the antibodies of the present invention are produced in yeast according to the methods described in WO2005/040395. Briefly, vectors encoding the individual light or heavy chains of an antibody of interest are introduced into different yeast haploid cells, e.g. different mating types of the yeast *Pichia pastoris*, which yeast haploid cells are optionally complementary auxotrophs. The transformed haploid yeast cells can then be mated or fused to give a diploid yeast cell capable of producing both the heavy and the light chains. The diploid strain is then able to secret he fully assembled and biologically active antibody. The relative expression levels of the two chains can be optimized, for example, by using vectors with different copy number, using transcriptional promoters of different strengths, or inducing expression from inducible promoters driving transcription of the genes encoding one or both chains.

In one embodiment, the respective heavy and light chains of a plurality of different anti-IL-17A antibodies (the "original" antibodies) are introduced into yeast haploid cells to create a library of haploid yeast strains of one mating type expressing a plurality of light chains, and a library of haploid yeast strains of a different mating type expressing a plurality of heavy chains. These libraries of haploid strains can be mated (or fused as spheroplasts) to produce a series of diploid yeast cells expressing a combinatorial library of antibodies comprised of the various possible permutations of light and heavy chains. The combinatorial library of antibodies can then be screened to determine whether any of the antibodies has properties that are superior (e.g. higher affinity for IL-17A) to those of the original antibodies. See. e.g., WO2005/040395.

In another embodiment, antibodies of the present invention are human domain antibodies in which portions of an antibody variable domain are linked in a polypeptide of molecular weight approximately 13 kDa. See, e.g., U.S. Pat. Publication No. 2004/0110941. Such single domain, low molecular weight agents provide numerous advantages in terms of ease of synthesis, stability, and route of administration.

VI. Pharmaceutical Compositions and Administration

To prepare pharmaceutical or sterile compositions of the anti-huIL-17A antibodies of the present invention, the antibody is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.). In one embodiment, anti-IL-17A antibodies of the present invention are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antibody compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). Antibodies exhibiting high therapeutic indices are preferred. The data obtained from these cell culture assays and animal studies can be used in formulating a range of dosage for use in human. The dosage of such compounds ties preferably within a range of circulating concentrations that include the $ED_{50}$ with little or no toxicity. The dosage may vary within this range depending upon the dosage form employed and the route of administration.

The mode of administration is not particularly important. Suitable routes of administration include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration can be carried out in a variety of conventional ways, such as oral ingestion, inhalation, insufflation, topical application or cutaneous, transdermal, subcutaneous, intraperitoneal, parenteral, intra-arterial or intravenous injection. Intravenous administration to the patient is preferred.

Alternately, one may administer the antibody in a local rather than systemic manner, for example, via injection of the antibody directly into an arthritic joint or pathogen-induced lesion characterized by immunopathology, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being, treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et at. (2003) *New Eng. J. Med.* 348:601-608; Milgrom et al. (1999) *New Engl. J. Med.* 341:1966-1973; Slamon et al. (2001) *New Engl. J. Med.* 344:783-792; Beniaminovitz et at. (2000) *New Engl. J. Med.* 342:613-619; Ghosh et al. (2003) *New Engl. J. Med.* 348:24-32; Lipsky et al. (2000) *New Engl. J. Med.* 343: 1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing an inflammatory, autoimmune, or proliferative response to the reagent, In the case of human subjects, for example, chimeric, humanized and fully human antibodies are preferred.

Antibodies, antibody fragments, and cytokines can be provided by continuous infusion, or by doses administered, e.g., daily, 1-7 times per week, weekly, bi-weekly, monthly, bimonthly etc. Doses may be provided intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/kg, 10 m g, 25 mg/kg, 50 mg/kg or more (see, e.g., Yang, et al. (2003) *New Engl. J. Med.* 349:427-434; Herold, et al (2002) *New Engl. J. Med.* 346:1692-1698; Liu, et at (1999) *J. Neurol. Neurosurg. Psych.* 67:451-456; Portielji, et al. (20003) *Cancer Immunol. Immunother.* 52:133-144). Doses may also be provided to achieve a pre-determined target concentration of anti-IL-17A antibody in the subject's serum such as 0.1, 0.3, 1, 3, 10, 30, 100, 300 µg/ml or more. In other embodiments, a humanized anti-IL-17A antibody of the present invention is administered subcutaneously or intravenously, on a weekly, biweekly or "every 4 weeks" basis at 10, 20, 50, 80, 100, 200, 500, 1000 or 2500 mg/subject.

As used herein, "inhibit" or "treat" or ";treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to al amount of an IL-17A binding compound of the invention that, when administered alone or in combination with an additional therapeutic agent to a cell, tissue, or subject, is effective to prevent or ameliorate one or more symptoms of a disease or condition or the progression of such disease or condition. A therapeutically effective dose further refers to that amount of the binding compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%.

Methods for co-administration with a second therapeutic agent, e.g., cytokine, another therapeutic antibody, steroid, chemotherapeutic agent, or antibiotic are well known in the art, see, e.g., Hardman, et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) Cancer Chemotherapy and Biotherapy, Lippincott, Williams & Wilkins, Phila., PA. The pharmaceutical composition of the invention may also contain immunosuppressive or immunomodulating agents. Any suitable immunosuppressive agent can be employed, including but not limited to anti-inflammatory agents, corticosteroids, cyclosporine, tacrolimus (i.e., FK-506), sirolimus, interferons, soluble cytokine receptors (e.g., sTNRF and sIL-1R), agents that neutralize cytokine activity (e.g. inflixmab, etanercept), mycophenolate mofetil, 15deoxyspergualin, thalidomide, glatiramer, azathioprine, leflunomide, cyclophosphamide, methotrexate, and the like. The pharmaceutical composition can also be employed with other therapeutic modalities such as phototherapy and radiation.

The IL-17A binding compounds of the present invention can also be used in combination with one or more antagonists of other cytokines (e.g. antibodies), including but not limited to, IL-23, IL-1β, IL-6 and TGF-β. See, e.g., Veldhoen (2006) *Immunity* 24:179-189; Dong (2006) *Nat. Rev. Immunol.* 6(4): 329-333. In various embodiments, an IL-17A binding compound of the invention is administered before, concurrently with, or after administration of the another antagonist or antagonists. In one embodiment, an IL-17A binding compound of the present invention is used in treatment of the acute early phase of an adverse immune response (e.g. MS, Crohn's Disease) alone or in combination with an IL-23 antagonist. In the latter case, the IL-17A binding compound may be gradually decreased and treatment with the antagonist of IL-23 alone is continued to maintain suppression of the adverse response. Alternatively, antagonists to IL-1β, IL-6 and/or TGF-β may be administered concurrently, before or after an IL-17A binding compound of the present invention. See Cua and Kastelein (2006) *Nat. Immunol,* 7:557-559; Tato and O'Shea (2006) *Nature* 441:166-168; Iwakura and Ishigame (2006) *J. Clin. Invest.* 116:1218-1222.

Typical veterinary, experimental, or research subjects include monkeys, dogs, cats, rats, mice, rabbits, guinea pigs, horses, and humans.

VII. Uses

The present invention provides methods for using engineered anti-IL-17A antibodies for the treatment and diagnosis of inflammatory disorders and conditions, as well as autoimmune and proliferative disorders. Methods are provided for the diagnosis, prevention or treatment of inflammatory bowel disease (IBD), multiple sclerosis (MS), chronic obstructive pulmonary disease (COPD), cystic fibrosis (CF), psoriasis, systemic scleroderma, allograft rejection, autoimmune myocarditis and peritoneal adhesions (see, e.g., Chung et al. (2002) *J. Exp. Med.* 195:1471-78).

Psoriasis

The skin serves as an important boundary between the internal milieu and the environment, preventing contact with potentially harmful antigens. In the case of antigen/pathogen penetration, an inflammatory response is induced to eliminate the antigen. This response leads to a dermal infiltrate that consists predominantly of T cells, polymorphonuclear cells, and macrophages (see, e.g., Williams and Kupper (1996) *Life Sci.,* 58:1485-1507.) Normally, this inflammatory response, triggered by the pathogen, is under tight control and will be halted upon elimination of the pathogen.

In certain cases this inflammatory response occurs without external stimuli and without proper controls, leading to cutaneous inflammation. The present invention provides methods for treating and diagnosing cutaneous inflammation. Cutaneous inflammation, the result of the cellular infiltrate noted above as well as the secreted cytokines from these cells, encompasses several inflammatory disorders such as cicatricial pemphigoid, scleroderma, hidradenitis suppurativa, toxic epidermal necrolysis, acne, osteitis, graft vs. host disease (GvHD), pyoderma gangrenosum, and Behcet's Syndrome (see, e.g., Willams and Griffiths (2002) *Clin. Exp. Dermatol.,* 27:585-590). The most common for of cutaneous inflammation is psoriasis.

Psoriasis is characterized by T cell mediated hyperproliferation of keratinocytes coupled with an inflammatory infiltrate. The disease has certain distinct overlapping clinical phenotypes including chronic plaque lesions, skin eruptions, and pustular lesions (see, e.g., Gudjonsson et al. (2004) *Clin Exp. Immunol.* 135:1-8). Approximately 10% of psoriasis patients develop arthritis. The disease has a strong but complex genetic predisposition, with 60% concordance in monozygotic twins.

The typical psoriatic lesion is a well defined erythematous plaque covered by thick, silvery scales. The inflammation and hyperproliferation of psoriatic tissue is associated with a different histological, antigenic, and cytokine profile than normal skin. Among the cytokines associated with psoriasis are: TNFα, IL-19, IL-18, IL-15, IL-12, IL-7, IFNγ, IL-17A and IL-23 (see Gudjonsson et al., supra). IL-17A has been detected in psoriatic skin.

Anti-IL-17A antibodies of the present invention, either alone or in combination with other agents, may be used in prevention, treatment, diagnosis and prediction of psoriasis flare-ups. Use of anti-IL-17A antibodies in prediction and treatment of psoriatic outbreaks is described in commonly assigned U.S. Patent Application Publication 2005/0287593 and PCT Patent Publication WO 2005/108616, the disclosures of which are hereby incorporated by reference in their entireties.

Rheumatoid Arthritis (RA)

RA is a progressive, systemic disease characterized by inflammation of the synovial joints affecting about 0.5% of the world's population. Emery (2006) *BMJ* 332:152-155. Joint inflammation can lead to deformity, pain, stiffness and swelling, and ultimately to irreversible deterioration of the joint. Affected joints include knees, elbows, neck and joints of the hands and feet. Conventional treatment involves use of NSAIDs to alleviate symptoms, followed by administration of disease modifying antirheumatic drugs (DMARDs) such as gold, penicillamine, sulfasalazine and methotrexate. Recent advances include treatment with TNF-α inhibitors, including monoclonal antibodies, such as infliximab, adalumimab and golimumab, and receptor fusion proteins, such as etanercept. Treatment with these TNF-α inhibitors dramatically reduces structural damage from the disease.

The anti-IL-17A antibodies of the present invention may be used to treat RA in subjects in need of such treatment. Example 16 describes experiments involving the collagen-induced arthritis (CIA) model of RA, for which data are presented at FIGS. 3A-3D, and Table 15. The results show a reduction in the fraction of paws with high disease seventy scores in animals treated with an anti-IL-17A antibody of the present invention as compared with diluent and isotype controls.

The anti-IL-17A antibodies of the present invention may also be combined with other treatments for RA, e.g. methotrexate, azathioprine, cyclophosphamide, steroids, mycophenolate mofetil, NSAIDs, or TNF-α inhibitors (antibodies or receptor fragments).

In one embodiment, the anti-IL-17A antibodies of the present invention are used to treat human subjects who have not previously responded adequately to treatment with DMARDs alone. In another embodiment, treatment with the anti-IL-17A antibodies of the present invention is begun early in the course of disease, without requiring prior failure of DMARD therapy. Such early intervention may be appropriate, for example, once the safety of the antibody therapy has been firmly established.

Clinical improvement is measured by determining the ACR score, as described in more detail in Example 18. In various embodiments, ACR scores of 20, 50, and 70 are the desired endpoint, and these endpoints may be assessed at any appropriate point in the course of treatment, such as 5, 10, 15, 24, 40, 50 or more weeks.

Multiple Sclerosis (MS)

MS is thought to be an autoimmune disease of the central nervous system (CNS) involving loss of myelin from nerve fibers, resulting in plaques or lesions. The most common form is relapsing/remitting MS in which well defined symptomatic flare-ups occur, followed by periods of partial or complete remission. Conventional treatment options include interferon-β-1a and -1b, mitoxantrone, the tetrapeptide glatiramer acetate, therapeutic alpha-4-integrin-specific antibodies (natalizumab), or small molecule antagonists of alpha-4-integrin (e.g. those disclosed at WO2003/084984).

The anti-IL-17A antibodies of the present invention may be used to treat MS in subjects in need of such treatment. The anti-IL-17A antibodies may also be combined with other treatments for MS, e.g. interferon-β, interferon-α, steroids or alpha-4-integrin-specific antibodies.

Inflammatory Bowel Disease (IRD)

IBD is the name for a group of disorders (e.g. Crohn's disease and ulcerative colitis) in which the intestines become inflamed, resulting in abdominal cramps and pain, diarrhea, weight loss and intestinal bleeding. IBD affects over 600,000 Americans. Conventional treatment options include sulfasalazine, corticosteroids (e.g. prednisone), immune system suppressors such as azathioprine and mercaptopurine, or an antibiotic (e.g. metronidazole) for Crohn's disease. Therapeutic monoclonal antibody treatments include etanercept, natalizumab and infliximab.

The anti-IL-17A antibodies of the present invention may be used to treat DB in subjects in need of such treatment. Yen et al. (2006) *J. Clin. Invest.* 116:1310-1316; Fujimo et al. (2003) *Gut* 52:65-70. The anti-IL-17A antibodies of the present invention may also be combined with other treatments for IBD, e.g. IL-10 (see U.S. Pat. Nos. 5,368,854, 7,052,686), steroids and sulfasalazine.

In other embodiments, antibodies of the present invention that do not block binding of IL-7A to its receptor (e.g. non-neutralizing antibody 12E6) are used therapeutically to stabilize IL-17A in subjects in need to prolonged IL-17A activity. Such subjects include patients suffering from infections or cancers.

Many modifications and variations of this invention can be made without departing from its spirit and scope, as will be apparent to those skilled in the art. The invention is defined by the terms of the appended claims, along with the full scope of equivalents to which such claims are entitled. The specific embodiments described herein, including the following examples, are offered by way of example only, and do not by their details limit the scope of the invention.

Example 1

General Methods

Standard methods in molecular biology are described (Maniatis, et al (1982) *Molecular Cloning, A Laboratory Manual*, Cold Spring Harbor Laboratory Press, Cold Spring Harbor, N.Y.; Sambrook and Russell (2001) *Molecular Cloning*, 3$^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology, Vols.* 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) J. Biol. Chem. 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al., (1996) *Nature* Biotechnol. 14:309-314; Barbas (11995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Brain et al. (1999) *Nature Biotechnol.* 17:397-399).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Set. USA* 92:7021-7025; Carter (2001) *J. Immunol. Methods* 248: 7-15; Volkel, et al. (2001) *Protein Engineering* 14:815-823; Segal, et al. (2001) *J. Immunol Methods* 248:1-6; Brennan, et al. (1985) Science 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol. Chem.* 276:12999; Propst et al. (2000) *J. Immunol.* 165:2214; Long (1999) *Ann. Rev. Immunol.* 17:875).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies will usually bind with at least a $K_d$ of about $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M (see, e.g., Presta et al. (2001) *Thromb. Haemost.* 85:379-389; Yang et al. (2001) *Crit. Rev. Oncol. Hematol.* 38:17-23; Carnahan et al. (2003) *Clin. Cancer Res.* (Suppl.) 9:3982s-3990s).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146: 169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (994) *Flow Cytometry Principles for Clinical Laboratory Practice*, John Wiley and Sons, Hoboken, N.J.; Givan (2001) *Flow Cytometry; 2$^{nd}$* ed., Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et alt (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nevada); Menne, et al. (2000) *Boinformatics* 16: 741-742; Menne, et al. (2000) *Bioinformatics Applications Note* 16:741-742; Wren, et at (2002) *Comput. Methods Programs Biomed.* 68:177-181; von Heijne (1983) *Eur. J. Biochem.* 133:17-21; von Heijne (1986) *Nucleic Acids Res.* 14:4683-4690).

Example 2

Rat Anti Human IL-17A Monoclonal Antibodies

Monoclonal antibodies to human IL-17A were obtained as follows. Eight week old female Lewis rats (Harlan Sprague Dawley, Indianapolis, Ind., USA) were given a series of injections of recombinant human IL-17A (rhIL-17A) that had been expressed from adenoviral vectors in HEK 293 cells. The injections were given at days 0, 14, 32, 46, and 83.

The day 0 injection was a subcutaneous (sc) injection of 50 pg rhIL-17A, accompanied by intraperitoneal (ip) injection of Freund's Complete Adjuvant. Day 14, 32 and 46 sc injections of 25 μg rhIL-17A were accompanied by ip injection of Freund's Incomplete Adjuvant. The day 83 injection was a combination of an ip injection of 20 μg rhIL-17A in Freund's Incomplete Adjuvant and an intravenous (iv) tail vein injection of rhIL-17A in saline.

A test bleed was performed at day 53. Fusion of rat splenocytes was performed on day 87, using $1.6 \times 10^8$ splenocytes and $1.8 \times 10^8$ myeloma cells divided into in thirty 96-well plates, giving a total of $1.13 \times 10^5$ total cells per well.

Primary screening of the resulting monoclonal antibodies (thousands) was performed by indirect rhIL-17A ELISA (see Example 5). Secondary screens on the resulting antibodies included neutralization of rhIL-17A-induced expression of murine IL-6 by ST2 (mouse stromal) cells and neutralization of rhIL-17A-induced proliferation of Ba/F3 hIL-17Rc:mGC-SFR cells (see Example 11). Approximately eleven of the monoclonals were studied further after the first and second screens. Subsequent experiments were performed to confirm that the candidate antibodies were able to bind to native huIL-17A to ensure that they would be useful in various therapeutic, diagnostic and/or research purposes. Such screening may be done using binding assays (such as indirect ELISA or sandwich ELISA), by in vitro activity assay, or by in vivo activity assay, examples of which are provided herein.

Example 3

Humanization of Rat Anti Human IL-17A Antibodies

The humanization of rat anti human IL-17A monoclonal antibody 16C10 was performed essentially as described in WO 2005/047324 and WO 2005/047326, the disclosures of which are hereby incorporated by reference in their entireties. Briefly, human constant domains were used to replace the parental (rat) constant domains, and human germline sequences homologous to the rat variable domain sequences were selected and used to provide a human framework for the rat CDRs, as described in more detail below.

Procedure for Selection of Human Germline Framework Sequences

The following steps are used in selecting the appropriate germine framework sequences in humanizing the anti-human IL-17A antibodies of the present invention.

1) Clone and sequence non-human $V_L$ and $V_H$ domains and determine amino acid sequence.

Heavy Chain

2) Compare the non-human $V_H$ sequence to a group of five human $V_H$ germline amino acid sequences; one representative from subgroups IGHV1 and IGHV4 and three representatives from subgroup IGHV3. The $V_H$ subgroups are listed in M.-P. Lefranc (2001) "Nomenclature of the Human Immunoglobulin Heavy (IGH) Genes", *Experimental and Clinical Immunogenetics,* 18:100-116. Comparison to the five germline sequences is performed as follows:

A) Assign the non-human $V_H$ sequence residue numbers according to Kabat et al. (1991).

B) Align the non-human $V_H$ sequence with each of the five human germline sequences. Since the V genes only comprise $V_H$ residues 1-94, only these residues are considered in the alignment.

C) Delineate the complementarity-determining (CDR) and framework (FR) regions in the sequence. CDR and FR are defined as a combination of the definitions provided in Kabat et al. (1991) (Id.) and Chothia and Lesk (1987) "Canonical Structures for the Hypervariable Regions of Immunoglobulins", *Journal of Molecular Biology,* 196:

901-917. The definition is thus: $V_H$ CDR1=26-35, CDR2=50-65, CDR3=95-102.

D) For each listed residue position below (Table 1), assign numerical score at each residue position for which the non-human and human sequences are IDENTICAL:

TABLE 1

| Residue # | Score | Reason |
|---|---|---|
| 2 | 4 | Affects CDR-H1,3* |
| 4 | 3 | Affects CDR-H1,3 |
| 24 | 3 | Affects CDR-H1 |
| 26 | 4 | Affects CDR-H1* |
| 27 | 4 | Affects CDR-H1,3* |
| 29 | 4 | Affects CDR-H1* |
| 34 | 4 | Affects CDR-H1* |
| 35 | 2 | VH/VL interface |
| 37 | 2 | VH/VL interface |
| 39 | 2 | VH/VL interface |
| 44 | 2 | VH/VL interface |
| 45 | 2 | VH/VL interface |
| 47 | 4 | VH/VL interface, CDRL3 |
| 48 | 3 | Affects CDR-H2 |
| 49 | 3 | Affects CDR-H2 |
| 50 | 2 | VH/VL interface |
| 51 | 3 | Affects CDR-H2 |
| 58 | 2 | VH/VL interface |
| 59 | 3 | Affects CDR-H2 |
| 60 | 2 | VH/VL interface |
| 63 | 3 | Affects CDR-H2 |
| 67 | 3 | Affects CDR-H2 |
| 69 | 3 | Affects CDR-H2 |
| 71 | 4 | Affects CDR-H2* |
| 73 | 3 | Affects CDR-H1 |
| 76 | 3 | Affects CDR-H1 |
| 78 | 3 | Affects CDR-H1 |
| 91 | 2 | VH/VL interface |
| 93 | 3 | Affects CDR-H3 |
| 94 | 4 | Affects CDR-H3* |
| | max 89 | |

*Noted as affecting CDR conformation in C. Chothia et al. (1989) "Conformations of Immunoglobulin Hypervariable Regions", Nature 342: 877-883.

E) Add all residue position scores. Acceptor germline sequence is the one with the highest total score. In a case where two or more germline sequences have identical scores, then:

1) Among the following residue positions add 1 to the total for each position where the non-human and human sequences are IDENTICAL. 1, 3, 5-23, 25, 36, 38, 40-43, 46, 66, 68, 70, 72, 74, 75, 77, 79-90, 92 (max 49).

2) Acceptor germline sequence is the one with the highest total score. If two or more germline sequences still have identical scores, either one is acceptable as acceptor Light Chain III) If the Vim sequence is a member of the kappa subclass of $V_L$, compare non-human $V_L$ sequence to a group of four human $V_L$ kappa germline amino acid sequences. The group of four is comprised of one representative from each of four established human $V_L$ subgroups listed in Barbie and Lefranc (1998) "The Human Immunoglobulin Kappa Variable (IGKV) Genes and Joining (IGKJ) Segments", *Experimental and Clinical Immunogenetics,* 15:171-183, and M.-P. Lefranc (2001) "Nomenclature of the Human Immunoglobulin Kappa (IGK) Genes", *Experimental and Clinical Immunogenetics,* 18:161-174. The four subgroups also correspond to the four subgroups listed in Kabat et al. (1991) at pp. 103-130. Comparison to the four germline sequences is performed as follows:

A) Assign the non-human $V_L$ sequence residue numbers according to Kabat et al. (1991).

B) Align the non-human $V_L$ sequence with each of the four human germine sequences. Since the V genes only comprise $V_L$ residues 1-95, only these residues are considered in the alignment.

C) Delineate the complementarity-determining (CDR) and framework (FR) regions in the sequence. CDR and FR are defined as a combination of the definitions provided in Kabat et al. (1991) and Chothia and Lesk (1987) "Canonical Structures for the Hypervariable Regions of Immunoglobulins" *Journal of Molecular Biology,* 196: 901-917. The definition is thus: $V_L$ CDR1=24-34, CDRC2=50-56, CDR3=89-97.

D) For each listed residue position below (Table 2), assign numerical score at each residue position for which the non-human and human sequences are IDENTICAL:

TABLE 2

| Residue # | Score | Reason |
|---|---|---|
| 2 | 4 | Affects CDR-L1,3* |
| 4 | 3 | Affects CDR-L1,3 |
| 25 | 4 | Affects CDR-L1* |
| 29 | 4 | Affects CDR-L1,3* |
| 33 | 4 | Affects CDR-L1,3* |
| 34 | 2 | VL/VH interface |
| 36 | 2 | VL/VH interface |
| 38 | 2 | VL/VH interface |
| 43 | 2 | VL/VH interface |
| 44 | 2 | VL/VH interface |
| 46 | 4 | VL/VH interface, CDR-H3 |
| 47 | 3 | Affects CDR-L2 |
| 48 | 4 | Affects CDR-L2* |
| 49 | 2 | VL/VH interface |
| 55 | 2 | VL/VH interface |
| 58 | 3 | Affects CDR-L2 |
| 62 | 3 | Affects CDR-L2 |
| 64 | 4 | Affects CDR-L2* |
| 71 | 4 | Affects CDR-L1* |
| 87 | 2 | VL/VH interface |
| 89 | 2 | VL/VH interface |
| 90 | 4 | Affects CDR-L3* |
| 91 | 2 | VL/VH interface |
| 94 | 2 | VL/VH interface |
| 95 | 4 | Affects CDR-L3* |

*Noted as affecting CDR conformation in C. Chothia et al. "Conformations of Immunoglobulin Hypervariable Regions", Nature 342: 877-883, 1989.

E) Add all residue position scores. Acceptor germline sequence is the one with the highest total score. In a case where two or more germline sequences have identical scores, then:

1) Among the following residue positions add 1 to the total for each position where the non-human and human sequences are IDENTICAL: 1, 3, 5-23, 35, 37, 39-42, 57, 59-61, 63, 65-70, 72-86, 88.

2) Acceptor germ line sequence is the one with the highest total score. If two or more germline sequences still have identical scores, either one is acceptable as acceptor.

If the $V_L$ sequence is a member of the lambda subclass of $V_L$, an analogous procedure is performed using human $V_L$ lambda germline amino acid sequences from the literature sources cited above.

Humanization of Anti-human IL-17A Antibodies

With regard to modification of the constant domains, the variable light and heavy domains of antibody 16C10 (rat anti-human IL-17A IgG1) were cloned and fused to a human kappa light chain (CL domain) and human IgG1 heavy chain (CH1-hinge-CH2-CH3), respectively, This combination of the rat variable domains and human constant domains comprises a chimeric version of antibody 16C10. The sequences of the light and heavy chains of this chimeric 16C10C are provided at SEQ ID NOs: 9 and 10, respectively.

With regard to modification of the framework regions of the variable domains, the amino acid sequence of the $V_H$ domain of antibody 16C10 was compared to a group of five human $V_H$ germline amino acid sequences; one representative from subgroups IGHVI and IGHV4 and three representatives from subgroup IGHV3. The $V_H$ subgroups are listed in M.-P. Lefranc, "Nomenclature of the Human Immunoglobulin Heavy (IGH) Genes," *Experimental and Clinical Immunogenetics*, 18:100-116, 2001. Antibody 16C10 scored highest against human heavy chain germline DP-71 in subgroup IV.

The $V_L$ sequence of 16C10 was of the kappa subclass. This sequence was compared to a group of four human $V_L$ kappa germline amino acid sequences. The group of four is comprised of one representative from each of four established human $V_L$ subgroups listed in V. Barbie & M.-P. Lefranc, "The Hu-man Immunoglobulin Kappa Variable (IGKV) Genes and Joining (IGKM) Segments", *Experimental and Clinical Immunogenetics*, 15:171-183, 1998 and M.-P. Lefranc, "Nomenclature of the Human Immunoglobulin Kappa (CGK) Genes", *Experimental and Clinical Immunogenetics*, 18:161-174, 2001. The four subgroups also correspond to the four subgroups listed in Kabat et al. (1991) at pp. 103-130. Antibody 16C10C scored highest against human light chain germline Z-A19 in subgroup II.

Once the desired germline framework sequences were determined, a plasmid encoding the full-length humanized variable heavy and light chains was generated. Substitution of human framework residues in place of the framework residues of the parental rat antibody 16C10 can be viewed equivalently as the grafting of the rat 16C10 CDRs onto the human framework sequences. The resulting antibody is referred to herein as "16C10wt", with the "wt" designating the presence of the same CDRs as the parental rat 16C10, as distinguished from the optimized CDRs (having two single amino acid alterations) discussed below. Both the light and heavy chain variable domains were codon optimized, synthesized and inserted onto constant domains to provide for potentially optimal expression. Codon optimization, which may improve expression of cloned antibodies, is purely optional.

In addition to the substitution of human constant domain and framework sequences, the humanized 16C10 wt antibody was also modified at two CDR residues to provide for greater chemical stability of the final humanized antibody. The two changes are represented by bolded amino acid residues in the "hu16C10" $V_H$ sequence shown in FIG. 1B. With reference to the Kabat numbering used in FIG. 1B, residue 54 of CDR2 was changed from N (asparagine) in the rat antibody to Q (glutamine) in the humanized antibody to reduce the potential for formation of isoaspartate at the NG sequence at residues 54-55. Isoaspartate formation may debilitate or completely abrogate binding of an antibody to its target antigen. Presta (2005) *J. Allergy Clin Immunol.* 116:731 at 734. In addition, residue 96 of CDR3 was changed from M (methionine) in the rat antibody to A (alanine) in the humanized antibody to reduce the possibility that the methionine sulfur would oxidize, which could reduce antigen binding affinity and also contribute to molecular heterogeneity in the final antibody preparation. Id. These single-residue modifications can be represented as N54Q and M96A. The final humanized 16C10 antibody disclosed herein comprises these two substitutions relative to the parental rat 16C10 CDRs.

In another embodiment of the present invention, the chimeric (not humanized) 16C10 antibody is altered to incorporate the two single-residue modifications described above for the humanized form, i.e. N54Q and M96A.

The amino acid sequences of the light and heavy chains of humanized antibody 16C10 (hu 16C10) are provided at FIGS. 2A and 2B respectively, and at SEQ ID NOs. 2 and 4 (which include signal sequences). One embodiment of nucleotide sequences encoding the light and heavy chains of hu 6C10 are shown in SEQ ID NOs:1 and 3. Another embodiment of nucleotide sequences encoding the light and heavy chains of hu 16C10 are shown in FIG. 5A (SEQ ID NO:62) and FIG. 5B (SEQ ID NO:63).

In the interest of clarity with regard to nomenclature, it is important to recognize that the Kabat numbering system includes non-numerical amino acid residue designations (e.g. $V_H$ residues 83a, 83b, 83c) to accommodate variations in the lengths of CDRs and framework regions among various antibodies. Although this numbering system is advantageous in allowing easy reference to corresponding amino acid residues among various antibodies with CDRs of different lengths, it can result in conflicting designations for specific amino acid residues when compared with strict sequential-numeric sequence numbering (e.g. sequence listings). Amino acid residue designations herein are made with reference to the relevant sequence listing unless otherwise noted, for example by reference to "Kabat numbering".

As an additional point of clarification with regard to nomenclature. SEQ ID NOs: 2 and 4 (humanized 16C10) include the sequences of N-terminal signal peptides (the first 19 residues of each), which amino acids are removed in the mature form of the antibody. SEQ ID NOs: 1, 3, 62 and 63 include 57 nucleotides encoding the signal sequences. As used herein, a "mature" form of a protein refers to the protein without the signal sequence.

Humanized antibody 4C3 is created by methods analogous to those described above for antibody 16C10. Because the parental rat 4C3 antibody differed only at a single amino acid residue in the framework region of the light chain, and such framework regions are replaced with human germline framework sequences during humanization, the ultimate humanized 4C3 antibody sequence is identical to the sequence of humanized 16C10 antibody.

Humanized antibody 30C10C is also created by methods analogous to those described above for antibody 16C10. In determining the proper human framework sequences to be used, the parental rat 30C10 antibody scores highest against human heavy chain germline DP-46 in subgroup III and human light chain germine Z-A19 in subgroup II, so those framework sequences are substituted for the rat framework sequences. The humanized 30C10 $V_L$ and $V_H$ sequences are provided at SEQ ID NOs: 22 and 23, respectively. In other embodiments, one or more methionine residues in the CDRs of rat 30C10 are mutated to avoid the potential of oxidation of the methionine sulfur in the humanized 30C10 antibody. Specifically, heavy chain residue 34 (in CDRH1) and/or light chain residue 30f (Kabat numbering, see FIG. 1A) are changed from methionine to another amino acid, e.g. alanine. Such antibodies are subsequently screened to ensure that the methionine substitution does not decrease IL-17A binding affinity to unacceptable levels.

Chimeric, humanized, and signal sequence-containing versions of antibody 12E6 are created using the methods described herein, by analogy with preparation of such antibodies based on parental rat antibody 16C10. Light and heavy chain CDRs for parental rat antibody 12E6 are provided at SEQ I NOs: 34-36 and 37-39. Human constant domain and variable domain framework sequences are introduced as described above. In one embodiment, heavy chain residue 34 (in CDRH1) is changed from a methionine to another amino acid, e.g. alanine, to avoid the potential of oxidation of the methionine sulfur in the humanized 12E6 antibody. The resulting antibodies are subsequently screened to ensure that the methionine substitution does not decrease IL-17A binding affinity to unacceptable levels.

Chimeric, humanized, and signal sequence-containing versions of antibody 23E12 are created using the methods described herein, by analogy with preparation of such antibodies based on parental rat antibody 16C10. Light and heavy chain variable domain sequences for the parental rat antibody 23E12 are provided at SEQ ID NOs: 44 and 46 (DNA), and 45 and 47 (amino acid). CDRs for parental rat antibody 23E12 are provided at SEQ ID NOs: 48-50 (light chain) and 51-53 (heavy chain). Human constant domain and variable domain framework sequences are introduced into the parental rat antibodies as described above.

Example 4

Fully Human Anti-IL-17A Antibodies

Fully human anti-IL-17A monoclonal antibodies are generated using transgenic mice carrying parts of the human immune system rather than the mouse system. These transgenic mice, referred to herein as "HuMAb" mice, contain human immunoglobulin gene miniloci that encode unrearranged human heavy (μ and γ) and κ light chain immunoglobulin sequences, together with targeted mutations that inactivate the endogenous μ and κ chain loci (Lonberg et al. (1994) *Nature* 368(6474):856-859). Accordingly, the mice exhibit reduced expression of mouse IgM or κ, and in response to immunization, the introduced human heavy and light chain transgenes undergo class switching and somatic mutation to generate high affinity human IgG κ monoclonal antibodies (Lonberg et al. (1994), supra; reviewed in Lonberg (1994) *Handbook of Experimental Pharmacology* 113:49-101; Lonberg et al. (1995) *Intern. Rev. Immunol.* 13:65-93, and Harding et al. (1995) *Ann. N.Y. Acad. Sci.* 764:536-546). The preparation of HuMab mice is commonly known in the art and is described, for example, in Taylor et al. (1992) *Nucleic Acids Research* 20:6287-6295; Chen et al. (1993) *International Immunology* 5: 647-656; Tuaillon et al. (1993) *Proc. Nat'l. Acad. Sci. USA* 90:3720-3724; Choi et al. (1993) *Nature Genetics* 4:117-123; Chen et al. (1993) *EMBO J.* 12: 821-830; Tuaillon et al. (1994) *J. Immunol.* 152:2912-2920; Lonberg (1994) *Handbook of Experimental Pharmacology* 113:49-101; Taylor et al. (1994) *International Immunology* 6: 579-591; Lonberg et al. (1995) *Intern. Rev Immunol.* 13: 65-93; and Fishwild et al. (1996) *Nature Biotechnology* 14: 845-851; the contents of which are hereby incorporated by reference in their entireties. See also U.S. Pat. Nos. 5,545,806; 5,569,825; 5,625,126; 5,633,425; 5,789,650; 5,877,397; 5,661,016; 5,814,318; 5,874,299; 5,770,429 and 5,545,807; and International Patent Application Publication Nos. WO 98/24884; WO 94/25585; WO 93/1227; WO 92/22645 and WO 92/03918, the disclosures of all of which are hereby incorporated by reference in their entireties.

To generate fully human monoclonal antibodies to IL-17A, HuMab mice are immunized with an antigenic IL-17A polypeptide as described by Lonberg et al. (1994); Fishwild et al. (1996) and WO 98/24884. Preferably, the mice are 6-16 weeks of age upon the first immunization. For example, a purified preparation of IL-17A can be used to immunize the HuMab mice intraperitoneally. The mice can also be immunized with whole HEK293 cells that are stably transformed or transfected with an IL-17A gene. An "antigenic IL-17A polypeptide" may refer to an IL-17A polypeptide of any fragment thereof, which elicits an anti-IL-17A immune response in HuMab mice.

In general, HuMAb transgenic mice respond best when initially immunized intraperitoneally (IP) with antigen in complete Freund's adjuvant, followed by every other week IP immunizations (usually up to a total of 6) with antigen in incomplete Freund's adjuvant. Mice are immunized first with cells expressing IL-17A (e.g., stably transformed HEK293 cells), then with a soluble fragment of IL-17A, followed by alternating immunizations with the two antigens. The immune response is monitored over the course of the immunization protocol with plasma samples being obtained by retroorbital bleeds. The plasma are screened for the presence of anti-IL-17A antibodies, for example by ELISA, and mice with sufficient titers of immunoglobulin are used for fusions. Mice are boosted intravenously with antigen three days before sacrifice and removal of the spleen. Two to three fusions for each antigen may be necessary. Several mice are immunized for each antigen. For example, a total of twelve HuMAb mice of the HCO7 and HCO12 strains can be immunized.

Hybridoma cells producing the monoclonal, fully human anti-TL-7A antibodies are produced by methods commonly known in the art, such as the hybridoma technique originally developed by Kohler et al. (1975) (*Nature* 256:495-497); the trioma technique (Hering et al. (1988) *Biomed. Biochim. Acta.* 47:211-216 and Hagiwara et al. (1993) *Hum. Antibody Hybridomas* 4:15); the human B-cell hybridoma technique (Kozbor et al. (1983) *Immunology Today* 4:72 and Cote et al. (1983) *Proc. Nat'l. Acad. Sci. U.S.A.* 80:2026-2030); and the EBV-hybridoma technique (Cole et al. (1985) in *Monoclonal Antibodies and Cancer Therapy*, Alan R. Liss, Inc., pp. 77-96). Preferably, mouse splenocytes are isolated and fused with PEG to a mouse myeloma cell line based on standard protocols. The resulting hybridomas may then be screened for the production of antigen-specific antibodies. In one embodiment, single cell suspensions of splenic lymphocytes from immunized mice are fused to one-sixth the number of P3X63-Ag8.653 nonsecreting mouse myeloma cells (ATCC, CRL 1580) with 50% PEG. Cells are plated at approximately $2 \times 10^5$ cells/mL in a flat bottom microtiter plate, followed by a two week incubation in selective medium containing 20% fetal Clone Serum, 18% "653" conditioned media, 5% origen, 4 mM L-glutamine, 1 mM sodium pyruvate, 5 mM HEPES, 0.055 mM 2-mercaptoethanol, 50 units/ml penicillin, 50 mg/nm streptomycin, 50 mg/ml gentamicin and 1×HAT (Sigma; the HAT is added 24 hours after the fusion). After two weeks are cultured in medium in which the HAT is replaced with HT. Individual wells are then screened by ELISA for human anti-IL-17A monoclonal IgG antibodies. Once extensive hybridoma growth occurs, medium is observed usually after 10-14 days. The antibody secreting hybridomas are replated, screened again, and if still positive for human IgG, anti-IL-17A monoclonal antibodies are subcloned at least device by limiting dilution. The stable subclones are then cultured in vitro to generate small amounts of antibody in tissue culture medium for characterization.

In another embodiment, the anti-IL-17A antibody molecules of the present invention are produced recombinantly (e.g., in an *E. coli*/T7 expression system). In this embodiment, nucleic acids encoding the antibody molecules of the invention (e.g., $V_H$ or $V_L$) are inserted into a pET-based plasmid and expressed in the *E. coli*/T7 system. There are several methods to produce recombinant antibodies known in the art, e.g. U.S.

Pat. No. 4,816,567 which is hereby incorporated by reference. The antibody molecules may also be produced recombinantly in CHO or NSO cells.

Example 5

Indirect ELISA of anti-IL-17A Monoclonal Antibodies

Binding of anti-human-IL-17A monoclonal antibodies to rhIL-17A is assessed using an indirect enzyme-linked immunosorbent assay (ELISA). Briefly, a fixed concentration of rhIL-17A is bound directly to the wells of a microtiter plate. The monoclonal anti-IL-17A to be assayed is then is added to the rhIL-17A coated plate, where the antibody is captured and quantitated. A more detailed protocol follows.

A 96-well U-bottom MaxiSorp plate is coated with 50 μl/well of rhIL-17A (0.5 μg/ml) in carbonate coating buffer (the "assay plate"). Carbonate coating buffer is 2.9 g/L NaH-FCO$_3$, 1.6 g/L Na$_2$CO$_3$, pH 9.4. Plates are incubated covered at 4° C. overnight. Monoclonal antibodies to be screened are serially diluted in duplicate across the rows of a V-bottom plate such that the final volume is 60 μl/well (the "serial dilution plate"). The assay plate is washed three times with PBS-Tween in a plate washer (SkanWasher, Molecular Devices, Sunnyvale, Calif., USA) and blotted dry. PBS-Tween is obtained by adding 0.5 ml/L Tween 20 to 1×PBS. Fifty μl from each well of the serial dilution plate is transferred to the assay plate and incubated at 25° C. for one hour. Secondary antibodies are diluted 1/2000 in diluent (PBS-BSA-Tween, which is PBS-Tween with 1 g/L BSA). The secondary antibody for rat monoclonal antibodies is goat anti-rat IgG (H+L)—HRP (Jackson ImmunoResearch Laboratories, Inc., West Grove, Pa., USA). The secondary antibody for chimeric and humanized monoclonal antibodies is F(ab')$_2$ goat anti-human IgG Fcγ—HRP (Jackson ImmunoResearch Laboratories, Inc.). The assay plate is washed as before. Diluted secondary antibodies (100 μl/well) are added to the appropriate wells in the assay plate, and the plate is incubated at 25° C. for 45 minutes. The assay plate is washed as before. ABTS (100 μl/well) (Kirkegaard & Perry Laboratories, Gaithersburg, Md., USA) is added, and the plate is incubated at 25° C. for 5-10 minutes, after which absorbance is read at 405 nm on a plate reader (Versamax, Molecular Devices, Sunnyvale, Calif., USA) with a 5 second shake before reading.

Indirect ELISA results for various forms of antibody 16C10 of the present invention are shown in Table 5. Binding is reported as an EC50 (the concentration of antibody necessary to obtain half-maximal signal). The results show that binding is detected with all forms of 16C10. Although such indirect ELISA assays are useful in quickly determining the presence or absence of anti-IL-17A antibodies, the EC50 numbers obtained may be assay-dependent and are typically not used to assess the absolute binding affinity for any given antibody.

TABLE 5

Indirect Anti-IL-17A Antibody ELISA

| mAb | rhIL-17A (μg) | EC50 (pM) |
|---|---|---|
| rat 16C10 | 0.025 | 274 |
| chimeric 16C10 | 0.025 | 157 |
| humanized 16C10 wt | 0.025 | 212 |

Example 6

ELISA of Anti-IL-17A Monoclonal Antibodies

Binding of anti-human-IL-17A monoclonal antibodies to rhIL-17A is assessed using an ELISA as follows. Briefly, a capture antibody is bound to the wells of a microtiter plate, after which a fixed concentration of rhIL-17A is added. The monoclonal anti-IL-17A to be assayed is then titrated versus the bound rhIL-17A on the plate to determine the concentration of antibody needed to achieve half-maximal binding. A more detailed protocol follows.

A 96-well microtiter plate is coated with 100 μl/well of capture antibody (rat anti-hIL-17A 12E6, 0.5 μg/ml) in carbonate coating buffer pH 9.5 (the "assay plate"). Plates are incubated covered at 4° C. for 24 to 48 hours. The assay plate is washed three times in a plate washer (SkanWasher, Molecular Devices, Sunnyvale, Calif., USA) and blotted dry. The plate is then blocked with 200 μl/well of ELISA assay buffer (20 mM Tris-HCl, 0.15 M NaCl, pH7.4, 0.5% BSA, 0.05% Tween-20, 5M EDTA) for one hour at 25° C. on an orbital shaker. The plate is washed, and 100 μl/well of either adenovirus-derived rhIL-17A or *E. coli*-derived human IL-17 (IL-17A) (R&D Systems, Minneapolis, Minn., USA) (0.1 g/ml) is added in ELISA assay buffer and incubated for 2 hours at 25° C. on an orbital shaker. The plate is washed and the monoclonal antibodies to be screened are serially diluted across a row of seven wells in the range of 1000 ng/ml to 0.0813 ng/ml using 4-fold serial dilutions. Plates are incubated for 1.5 hours at 25° C. on an orbital shaker. Plates are washed and 100 μl/well secondary antibody (F(ab')$_2$ goat anti-human kappa light chain—HRP, 1:20,000 dilution, BioSource, Carlsbad, Calif., USA) is added, except for assay blank wells. Plates are washed twice (i.e. two cycles of 3 washes per cycle) with plate rotation between cycles. TMB substrate (Kirkegaard & Perry Laboratories, Gaithersburg, Md., USA) is added at 100 μl/well and incubated 3-5 minutes on an orbital shaker. Stop solution is added (100 μl/well) and the plate is read for absorbance at 450-570 um on a plate reader (Versamax, Molecular Devices, Sunnyvale, Calif., USA).

ELISA results for various forms of antibody 16C10 of the present invention are shown in Table 6. Binding is reported as an EC50 (the concentration of antibody necessary to obtain half-maximal signal). The results show that binding is detected with all forms of 16C10. Values presented with error ranges represent the mean of multiple determinations with the standard deviation.

TABLE 6

Anti-IL-17A Antibody ELISA

| mAb | human IL-17A | EC50 (pM) |
|---|---|---|
| hu 16C10 wt | rhIL-17A | 66 ± 14 |
| hu 16C10 wt | R&D Systems | 130 ± 19 |
| hu 16C10 VH N54A | rhIL-17A | 75 |
| hu 16C10 VH N54Q | rhIL-17A | 65 |
| hu 16C10 VH N60A | rhIL-17A | 63 |
| hu 16C10 VH N60Q | rhIL-17A | 74 |
| hu 16C10 VH M96L | rhIL-17A | 66 |
| hu 16C10 VH M96A | rhIL-17A | 60 |
| hu 16C10 VH M96K | rhIL-17A | 68 |
| hu 16C10 VH M96F | rhIL-17A | 125 |
| hu 16C10 VH M100hF | rhIL-17A | 49 |
| hu 16C10 VH M100hL | rhIL-17A | 53 |
| hu 16C10 (= VH N54Q/M96A) | rhIL-17A | 92 |
| hu 16C10 (= VH N54Q/M96A) | R&D Systems | 136 |

TABLE 6-continued

Anti-IL-17A Antibody ELISA

| mAb | human IL-17A | EC50 (pM) |
|---|---|---|
| hu 16C10 VH 54Q/M96A/M100hF | rhIL-17A | 80 |
| hu 16C10 VH 54Q/M96A/M100hF | R&D Systems | 118 |

Example 7

Binding Affinity of Anti-Human IL-17A Antibodies

Measuring binding of Rat and Chimeric Anti-Human IL-17A Antibodies using an Electrochemiluminescence (ECL) Assay Origen electrochemiluminescence technology, developed by IGEN, Inc. (Gaithersburg, Md., USA), and was employed to measure the binding of rat anti-human IL-17A antibodies (and one chimeric antibody) to FLAG-huL-17A. See the Elecsys® immunoassay system, Roche Diagnostics (Indianapolis, Ind., USA). Electrochemiluminescence technology uses a stable ruthenium metal chelate (Ori-TAG) which, in the presence of tripropylamine (TPA), generates electrochemiluminescence upon voltage application. Paramagnetic beads, microns in diameter, act as the solid phase and facilitate rapid assay kinetics. The bead/complex is channeled through a flow cell and captured at an electrode by magnetic application. Voltage is applied and resulting electrochemiluminescence is measured.

ECL assays were performed as follows. Three-fold serial dilutions of anti-human IL-17A mAbs in 50 µl of the assay buffer were made in a 96-well microtiter plate to give 1-3 µg/ml final concentration in the first well. Fifty µl of the assay buffer and 50 µl of biotinylated FLAG-huIL-17A at 50 ng/ml was added to each well, followed by the addition of either OriTag-labeled goat anti-rat IgG (H+L) pAb (50 µl at 450 ng/ml) or an anti-hIgG mAb (50 µl at 500 ng/ml). Finally 50 µl of Origen Streptavidin-Dynabeads at 0.1 mg/ml was added to each well. After 1 hr incubation at 25° C. the plate was processed by the Origen M-series M8/384 analyzer. Graph-Pad Prism software (GraphPad Software, San Diego, Calif., USA) was used to plot the data and calculate area under the curve, which is a rough measure of binding.

Results are presented in Table 7 (which includes some duplicate determinations). The two rows showing binding of rat 16C10 to FLAG-huIL-17A represent duplicate determinations. All rat anti-human IL-17A antibodies in the table (ID10, 16C10, 30C10, 23E12) bound to FLAG-huIL-17A, as did the chimeric 16C10. All four antibodies also bound to cyno IL-17A. Antibodies 16C10C and 30C10 did not bind to mouse IL-17A under the conditions of this assay, whereas antibodies ID10 and 23E12 did.

TABLE 7

Antibody Binding Determined by ECL

| mAb | Antigen | Area Under Peak |
|---|---|---|
| rat 1D10 | FLAG-hu-IL-17A | 477474 |
| rat 16C10 | FLAG-hu-IL-17A | 285792 |
| rat 16C10 | FLAG-hu-IL-17A | 374445 |
| rat 30C10 | FLAG-hu-IL-17A | 311752 |
| rat 23E12 | FLAG-hu-IL-17A | 285145 |
| chimeric 16C10 | FLAG-hu-IL-17A | 345982 |
| rat 1D10 | cyno IL-17 | 136497 |
| rat 16C10 | cyno IL-17 | 151543 |
| rat 30C10 | cyno IL-17 | 123916 |
| rat 23E12 | cyno IL-17 | 111242 |
| rat 1D10 | mu IL-17 | 252121 |
| rat 1D10 | mu IL-17 | 384999 |
| rat 16C10 | mu IL-17 | no binding |
| rat 16C10 | mu IL-17 | no binding |
| rat 30C10 | mu IL-17 | no binding |
| rat 30C10 | mu IL-17 | no binding |
| rat 23E12 | mu IL-17 | 143206 |
| rat 23E12 | mu IL-17 | 289185 |

Determining the Equilibrium Dissociation Constant (KCh) for Rat and Humanized Anti-Human IL-17A Antibodies using KinExA Technology The equilibrium dissociation constants ($K_d$) for anti human IL-17A antibodies were determined using the KinExA 3000 instrument (Sapidyne Instruments Inc., Boise, Id., USA). KinExA uses the principle of the Kinetic Exclusion Assay method based on measuring the concentration of uncomplexed antibody in a mixture of antibody, antigen and antibody-antigen complex. See, e.g., Darling and Brault (2004) *Assay Drug Dev. Technol.* 2(6):647-57. The concentration of free antibody is measured by exposing the mixture to a solid-phase immobilized antigen for a very brief period of time. 1 practice, this is accomplished by flowing the solution phase antigen-antibody mixture past antigen-coated particles trapped in a flow cell. Data generated by the instrument are analyzed using custom software. Equilibrium constants are calculated using a mathematical theory based on the following assumptions:

1. The binding follows the reversible binding equation for equilibrium:

$$k_{on}[Ab][Ag]=k_{off}[AbAg], \text{ where } K_d=k_{off}/k_{on}$$

2. Antibody (Ab) and antigen (Ag) bind 1:1 and total antibody equals antigen-antibody complex (AbAg) plus free antibody.

3. Instrument signal is linearly related to free antibody concentration.

KinExA analysis was performed on several rat anti-human IL-17A antibodies, humanized variants thereof and sequence variants of these humanized antibodies. IL-17A was derived from either human ("hu"), cynomolgus monkey ("cyno"), or mouse ("mu"). IL-17A from the same species was used in both the immobilized and solution phases for each KinExA determination. Poly(methyl-methacrylate) (PMMA) particles (98 micron) were coated with human, cyno or mouse IL-17A according to Sapidyne "Protocol for coating PMMA particles with biotinylated ligands having short or nonexistent linker arms." All experimental procedures were done according to the KinExA 3000 manual. All runs were done in duplicate.

The conditions for KinExA are provided at Table 8.

TABLE 8

| KinExA Conditions | | |
|---|---|---|
| IL-17A: | human, cyno | mouse |
| Sample volume: | 2 ml | 4 ml |
| Sample flow rate: | 0.25 ml/min | 0.25 ml/min |
| Label volume: | 1 ml | 1 ml |
| Label flow rate: | 0.25 ml/min | 0.25 ml/min |
| Antibody conc.: | 0.02-0.1 nM | 0.1 nM |
| Highest antigen conc.: | 4 nM | 64 nM (23E12) |
| | | 4.0 nM (1D10) |
| Lowest antigen conc.: | 1 pM | 62 pM (23E12) |
| | | 3.9 pM (1D10) |

Two-fold serial dilutions of the antigen were prepared and mixed with the antibody at constant concentration. The mixture was incubated for 2 hours at 25° C. to equilibrate.

Table 9 shows the results of the KinExA analysis. Molar concentrations for the KinexA analysis were calculated on the basis of a molecular weight of 75 kDa for antibodies and 15 kDa for IL-17A to account for the presence of two binding sites on the antibodies and the dimeric nature of IL-17A. For some antibodies, replicate experiments were performed with different batches of antibody and/or antigen, in which cases mean values are provided in Table 9 along with standard errors. Binding constants for the humanized 16C10 wt antibody and the parental rat 16C10 antibody were similar at approximately 5-10 pM, showing that humanization did not significantly reduce the high affinity of the parental rat 16C10 for human IL-17A. Humanized 16C10 incorporating various amino acid substitutions (N54Q, M96A, M100hF), including the final humanized 16C10 antibody (having N54Q and M96A substitutions compared to rat 16C10) were also assayed and found to have similar, high binding constants in the 1-10 pM range. The Fab fragment of hu 16C10 bound retained high affinity (16 pM) compared with the complete antibody. Other antibodies of the present invention (rat 1D10, rat 23E12, rat 30C10) also bound with high affinity to FLAG-huIL-17A, and to cyno IL-17A. Although rat 1D10 bound to mouse with 10 pM affinity, similar to its affinity for human and cyno IL-17A, rat 23E12 had 200-2000 lower affinity for mouse IL-17A (7000 pM). Antibodies 16C10 and 30C10 did not bind to mouse IL-17A (data not shown).

TABLE 9

| $K_d$ Values Determined by KinExA | | |
|---|---|---|
| mAb | Antigen | Kd (pM) |
| rat 16C10 | rhIL-17A | 6.0 |
| rat 16C10 | FLAG-huIL-17A | 3.6 |
| hu 16C10 wt | rhIL-17A | 8.8 ± 3.0 |
| hu 16C10 [= VH N54Q/M96A] | rhIL-17A | 3.9 ± 2.7 |
| hu 16C10 Fab | rhIL-17A | 16.1 |
| hu 16C10 VH N54A | rhIL-17A | 10.8 |
| hu 16C10 VH N54Q | rhIL-17A | 7.0 |
| hu 16C10 VH M96A | rhIL-17A | 9.9 |
| hu 16C10 VH N54Q/M96A/M100hF | rhIL-17A | 10.0 |
| rat 1D10 | FLAG-huIL-17A | 1.7 |
| rat 23E12 | FLAG-huIL-17A | 2.8 |
| rat 30C10 | FLAG-huIL-17A | 11.0 |
| rat 1D10 | cyno IL-17A | 9.8 |
| rat 23E12 | cyno IL-17A | 28.0 |
| rat 30C10 | cyno IL-17A | 32.6 |
| rat 16C10 | cyno IL-17A | 1.7 |
| hu 16C10 | cyno IL-17A | 16.3 |

TABLE 9-continued

| $K_d$ Values Determined by KinExA | | |
|---|---|---|
| mAb | Antigen | Kd (pM) |
| rat 1D10 | mu IL-17A | 10.3 |
| rat 23E12 | mu IL-17A | 7,000 |

Other methods known in the art, such as Biacore® surface plasmon resonance spectroscopy may be used to measure the affinity of antibodies of the present invention. Although Biacore® analysis was performed on several of the antibodies of the present invention, the binding affinity was generally too high to be measured accurately, specifically, the dissociation rate was too slow to be measured by this method. Such analysis may, however, be of use in the analysis of lower-affinity anti-IL-17A antibodies or anti-IL-17A antibodies having faster dissociation rate constants, Example 8

Synoviocyte Assay for Anti-IL-17A Antibodies

The ability of the anti-IL-17A antibodies of the present invention to block the biological activity of IL-17A (either rhIL-17A or native huIL-17A) is measured by monitoring IL-17A-induced expression of IL-6 and IL-8 in primary culture of human synoviocytes, as follows. Synoviocyes are isolated by collagenase digestion of a rheumatoid arthritis synovium obtained from a knee replacement patient. Synoviocytes are enriched by continuous passage in Growth Medium (DMEM, 10% BCS, 1× Pen-Strep (50 IU/ml penicillin 55 µg/ml streptomycin), 1× beta-mercaptoethanol (50 µM), 1× glutamine (20 mM), 25 mM HEPES), frozen down at passage number tree, and stored in liquid nitrogen when ready for use in an assay, a vial of the cells is thawed, plated, and the cells are allowed to grow to near confluence. The cells are then passaged 1:2 into larger flasks using typsin/EDTA. When sufficient cells have expanded, an experiment is initiated by trypsinizing the cells, plating into 96 well or 48 well plates, and allowing them to grow to total confluence.

IL-17A is diluted to 120 ng/ml, i.e. 4× the final concentration of 30 ng/ml (1 nM) IL-17A is either human (rhIL-17A and native huIL-17A) or from anon-human primate, in this case cynomolgus monkeys (cyno). 100 and 300 µl aliquots of the 4× IL-17A stocks are added to empty 96-well and 48-well plates, respectively.

Anti-IL-17A antibodies to be assayed are diluted in Growth Medium to 4× the maximum concentration to be tested in an experiment. The 4× anti-IL-17A stock is serially diluted 1:2 to cover the dynamic inhibition range of the assays Each of the serially diluted antibody samples (all are 4× their final concentration) are mixed 1:1 with the 4× IL-17A solutions in empty plates to generate mixtures with 2× concentrations of both IL-17A and anti-IL-17A antibodies. These mixtures are allowed to equilibrate at 37° C. in a tissue culture incubator for more than four hours.

Medium is removed from the adherent confluent synoviocytes and replaced with 100 µl (96-well plate) or 200 µl (48-well plate) of Growth Medium. An equal volume of the 2× ligand/2× antibody solution is added to synoviocytes to give 1× IL-17A (30 ng/ml final) and 1× antibody. Each well (data point) is run in duplicate. Synoviocytes are activated (i.e. exposed to the IL-17A/antibody mixture) for three days, at which point supernatants are transferred to 96 well plates, and optionally frozen, and stored at −80° C. until analyzed.

Microtiter plates containing supernatants are thawed and each solution is diluted 1:10 using Growth Medium. Supernatants are analyzed for IL-6 and IL-8 using Luminex bead pairs (Upstate, Charlottesville, Va., USA) following manufacturer's instructions.

Results are provided at Tables 10 (IL-6) and 11 (IL-8). Values presented with error ranges represent the mean of multiple determinations with the standard deviation. Results for various forms of antibody 16C10 are shown, including a humanized form of 16C10 having the original rat CDRs ("hu16C10 (wt)") as well as several variants having one, two or three changes in the heavy chain CDRs (generally "hu16C10X##Z", where X is the amino acid at residue ## in the heavy chain of hu16C10 (wt) and Z is the new amino acid). "NHP IL-17A" is non-human primate-derived IL-17A, in this case cynomolgus monkey IL-17A. "Native huIL-17A" refers to mature huIL-17A produced when the precursor protein is produced using the natural signal sequence, and differs from rhIL-17A by the absence of two N-terminal amino acids. Concentrations and $IC_{50}$ values are expressed in ng/ml, but may be expressed in pM units as well. For example, 30 ng/ml rhIL-17A corresponds to 1000 pM (MW=30 kDa) and 70 ng/ml anti-IL-17A antibody corresponds to approximately 470 pM (MW 150 kDa).

TABLE 10

IC50 (ng/ml) of Anti-IL-17A Measured by Synoviocyte IL-6 Production

| Antibody | rhIL-17A (30 ng/ml) | NHP IL-17A (30 ng/ml) | Native huIL-17A (10 ng/ml) |
|---|---|---|---|
| rat 1D10 | 105 ± 28 | 65 ± 15 | 25 |
| rat 16C10 | 63 ± 7 | 60 ± 10 | — |
| hu16C10 (wt) | 80 ± 10 | — | — |
| hu16C10 (N54A) | 60 | — | — |
| hu16C10 (N54Q) | 60 | — | — |
| hu16C10 (M96A) | 60 | — | — |
| hu16C10 (M96K) | 60 | — | — |
| hu16C10 (M100hF) | 70 | — | — |
| hu16C10 (N54Q/M96A) | 70 ± 8 | 70 ± 0 | 25 |
| hu16C10 (N54Q/M96A/M100hF) | 70 | — | — |

TABLE 11

IC50 (ng/ml) of Anti-IL-17A Measured by Synoviocyte IL-8 Production

| Antibody | rhIL-17A (30 ng/ml) | NHP IL-17A (30 ng/ml) | Native huIL-17A (10 ng/ml) |
|---|---|---|---|
| 1D10 | 59 ± 41 | 38 ± 13 | 40 |
| 16C10 | 38 ± 14 | 33 ± 8 | — |
| hu16C10 (wt) | 42 ± 16 | — | — |
| hu16C10 (N54A) | 25 | — | — |
| hu16C10 (N54Q) | 25 | — | — |
| hu16C10 (M96A) | 25 | — | — |
| hu16C10 (M96K) | 25 | — | — |
| hu16C10 (M100hF) | 50 | — | — |
| hu16C10 (N54Q/M96A) | 38 ± 10 | 38 ± 13 | 50 |
| hu16C10 (N54Q/M96A/M100hF) | 40 | — | — |

Example 9

NHDF Assay for Anti-IL-17A Antibodies

The ability of the anti-IL-17A antibodies of the present invention to block the biological activity of IL-17A is measured by monitoring rhIL-17A-induced expression of IL-6 in a normal human (adult) dermal fibroblast NHDF) primary cell line. Briefly, various concentrations of anti-IL-17A antibody to be assayed are incubated with rhIL-17A, and the resulting mixture is then added to cultures of NHDF cells. IL-6 production is determined thereafter as a measure of the ability of the antibody in question to inhibit IL-17A activity. A more detailed protocol follows.

A series two-fold dilutions of anti-IL-17A antibodies of interest are prepared (in duplicate) starting with a stock solution at 40 µg/ml. A stock solution of rhIL-17A is prepared at 120 ng/ml. Seventy µl of the rhIL-17A stock solution is mixed with 70 µl of the anti-IL-17A antibody dilutions in wells of a microtiter plate and incubated at room temperature for 20 minutes. One hundred µl of each of these mixtures is then added to wells of a microliter plate that had been seeded with $1 \times 10^4$ NHDF cells/well (100 µl) the previous night and allowed to incubate at 37° C. NHDF cells (passage 4) were obtained from Cambrex Bio Science (Baltimore, Md., USA). The resulting final concentration of rhIL-17A is 30 ng/ml (1 nM), and the antibodies range downward in two-fold intervals from 10 µg/ml. Plates are incubated at 37° C. for 24 hours, followed by harvesting of the supernatant and removal of 50 µl for use in an IL-6 ELISA.

The ELISA for detection of human IL-6 is performed as follows. Reagents are generally from R&D Systems (Minneapolis, Minn., USA). An hIL-6 capture antibody (50 µl/well of a 4 µg/ml solution) is transferred to wells of a microtiter plate, which is sealed and incubated overnight at 4° C. The plate is washed three times, and then blocked with 100 µl/well of blocking buffer for 1 hour or more The plate is then washed again three times. Experimental samples (50 µl of the culture supernatant) and controls (serial dilutions of IL-6 protein) are added to the wells in 50 µl and incubated for two hours. Plates are washed three times, and 50 µl/well of a biotinylated anti-IL-6 detection antibody (300 ng/ml) is added. The plates are incubated at room temperature for two hours, washed three times, and 100 µl/well of streptavidin HRP is added and incubated for 20 minutes. The plate is washed again, ABTS (BioSource, Carlsbad, Calif., USA) is added (100 µl/well), and incubated for 20 minutes. Stop solution is added (100 µl/well) and the absorbance at 405 nm is measured.

The $IC_{50}$ for an anti-IL-7A antibody of interest is the concentration of antibody required to reduce the level of rhIL-17A-induced IL-6 production to 50% of the level observed in the absence of any added anti-IL-17A antibody.

Results are provided at Table 12.

TABLE 12

Anti-IL-17A Antibody Inhibition of IL-6 Production in NHDF Cells

| Antibody | rhIL-17A IC50 (nM) | cyno IL-17A IC50 (nM) |
|---|---|---|
| rat 4C3 | 0.5 | 0.2 |
| rat 16C10 | 0.5 | 0.2 |
| rat 30C10 | 0.5 | 0.2 |
| rat 6C3 | 0.8 | 0.2 |
| rat 1D10 | 1 | 0.4 |
| rat 8G9 | 1 | 0.4 |
| rat 12B12 | 1 | 0.4 |

TABLE 12-continued

Anti-IL-17A Antibody Inhibition of IL-6 Production in NHDF Cells

| Antibody | rhIL-17A IC50 (nM) | cyno IL-17A IC50 (nM) |
|---|---|---|
| rat 18H6 | 1 | 0.3 |
| 23E12 | 1 | 0.3 |
| 29G3 | 1.5 | 2 |
| 29H1 | 1.5 | 0.5 |
| 12E6 | >70 | >70 |

Example 10

Foreskin Fibroblast Assay Anti-IL-17A Antibodies

The ability of the anti-IL-17A antibodies of the present invention to block the biological activity of IL-17A is measured by monitoring rhIL-17A-induced expression of IL-6 in HS68 foreskin fibroblast cell line. Reduced production of IL-6 in response to rhIL-17A is used as a measure of blocking activity by anti-IL-17A antibodies of the present invention.

Analysis of the expression of IL-17RC (an IL-17A receptor) in a panel of fibroblast cell lines identified the human foreskin fibroblast cell line HS68 (ATCC CRL1635) as a potential IL-17A responsive cell line. This was confirmed by indirect immunofluorescence staining with polyclonal goat anti-human IL-17R antibody (R&D Systems, Gaithersburg, Md., USA) followed by phycoerythrin (PE)-F(ab')$_2$ donkey anti-goat TgG (Jackson Immunoresearch, Inc., West Grove, Pa., USA), and analyzing the PE immunofluorescence signal on a flow cytometer (FACScan, Becton-Dickinson, Franklin Lakes, N.J., USA). As further validation of the model, IL-17A (both adenovirus-derived rhIL-17A and commercially available E. coli-derived IL-17A, R&D Systems) induced a dose-responsive induction of IL-6 in the HS68 cells with an EC50 of 5-10 ng/ml, which induction was blocked by pre-incubation with commercial polyclonal and monoclonal anti-L-17A antibodies (R&D Systems).

The IL-17A inhibition assay is performed as follows. A confluent T-75 flask of HS68 cells (approximately 2×10$^6$ cells) is washed with Dulbecco's PBS without Ca++ and Mg++ and then incubated with 5 ml of cell dissociation medium (Sigma-Aldrich, St. Louis, Mo., USA) for 2-5 minutes at 37° C. in an incubator at 5% CO$_2$. Cells are then harvested with 5 ml of tissue culture (TC) medium and centrifuged for 5 minutes at 1000 rpm. TC medium is Dulbecco's Modified Eagle's Medium (with glutamine), 10% heat-inactivated fetal bovine serum (Hyclone), 10 mM Hepes, 1 mM sodium pyruvate, penicillin, and streptomycin. Cells are resuspended in 2 ml TC medium, diluted 1:1 with trypan blue and counted. Cell concentrations are adjusted to 1×10$^5$ cells/ml in TC medium, and 0.1 ml/well is aliquoted into the wells of a flat-bottom plate containing 0.1 ml TC medium. Cells are grown overnight and the supernatant is aspirated and cells are washed with 0.2 ml of fresh TC medium.

Anti-IL-17A antibodies to be assayed are serially diluted in two-fold or -fold steps to give a series of stock solutions that can be used to create final antibody concentrations of 1 to 0.001 μm/ml in the IL-17A inhibition assay. A rat IgG control is used in each assay as well as media-only samples, as controls to measure spontaneous IL-6 production in HS68 cells. The TC medium is aspirated from the wells of the plate containing the HS68 cells. Aliquots of the various concentrations of anti-IL-17A antibody (0.1 ml of each) are pre-incubated in the wells with the HS68 cells 37° C. for 5 minutes prior to addition of 0.1 ml of 20 ng/ml rhIL-17A, to give a final concentration of rhIL-17A of 10 ng/ml (approximately 330 pM of IL-17A dimer). Cells are incubated 24 hours at 37° C., and supernatants (50-100 μl) are harvested and assayed for IL-6, for example using a human IL-6 ELISA kit from Pharmingen (OptEIA-BD Biosciences, Franklin Lakes, N.J., USA).

Results for several rat anti-human IL-17A antibodies of the present invention in the foreskin fibroblast IL-17A inhibition assay are provided at Table 13.

TABLE 13

Foreskin Fibroblast Assay

| anti-IL-17A antibody | IC50 (pM) |
|---|---|
| rat 16C10 | 67 |
| rat 1D10 | 65 |
| rat 8G9 | 29 |
| rat 29H1 | 247 |
| rat 29G3 | 63 |
| rat 23E12 | 126 |
| rat 6C3 | 192 |
| rat 4C2 | 107 |
| rat IgG1 | no binding |

Example 11

Ba/F3-hIL-17Rc-mGCSFR Proliferation Assay

The ability of the anti-IL17A antibodies of the present invention to block the biological activity of IL-17A is measured by monitoring rhIL-17A-induced proliferation of a cell line engineered to proliferate in response to IL-17A stimulation. Specifically, the Ba/F3 cell line (IL-3 dependent murine pro-B cells) was modified to express a fusion protein comprising the extracellular domain of a human IL-17A receptor (hIL-17RC) fused to the transmembrane domain and cytoplasmic region of mouse granulocyte colony-stimulating factor receptor (GCSFR). The resulting cell line is referred to herein as Ba/F3 hIL-17Rc-mGCSFR. Binding of homodimeric IL-17A to the extracellular IL-17RC domains causes dimerization of the hIL-17Rc-mGCFR fusion protein receptor, which signals proliferation of the Ba/F3 cells via their mGCSFR cytoplasmic domains. Such cells proliferate in response to IL-17A, providing a convenient assay for IL-17A inhibitors, such as anti-IL-17A antibodies.

The sensitivity of the Ba/F3-hIL-17Rc-mGCSFR proliferation assay to IL-17A stimulation makes it possible to perform experiments at relatively low concentrations of rhIL-17A (e.g. 3 ng/ml, 100 pM) compared with other assays, while still maintaining a robust and readily measurable proliferative response. This means that lower concentrations of anti-IL-17A antibodies are required to achieve a molar excess over rhIL-17A in the assay. Experiments performed at lower antibody concentrations make it possible to discriminate between high affinity antibodies that might otherwise be indistinguishable (i.e. experiments can be performed closer to the linear range in the antibody-IL-17A binding curve, rather than in the plateau).

Antibodies and IL-L17A were filtered through 0.22 μm filters after dilution to working stock concentrations but prior to addition to experimental samples. Four sets of samples were prepared, in duplicate, across rows of a 96-well flat bottom tissue culture plates. As used in this Example, Growth Medium is RPMI 1640 w/Glutamax (Invitrogen, Carlsbad, Calif., USA), 55 μM 2-mercaptoethanol, 10% formula fed Bovine Calf Serum (Irvine Scientific, Santa Ana, Calif., USA), 50 µg/mL gentamicin, 2 µg/mL puromycin, and 10 ng/mL mIL-3 BioAssay Medium is the same as Growth Medium but without puromycin and mIL-3. All serial dilutions in this Example were made into BioAssay Medium.

The following experimental samples (75 µl) were prepared: 1) a serial dilution of Growth Medium (including 10 ng/ml mIL-3); 2) a serial dilution of rhIL-17A; 3) a serial dilution of anti-IL-17A antibodies of the present invention mixed with 3 ng/ml IL-17A (final concentration after cells were added), including a "no antibody" control; and 4) a "cells only" control with no added antibodies, IL-17A or mIL-3. Ba/F3 hIL-7Rc-mGCSFR cells (7500 cells/well) were then added to bring the total volume to 100 µl/well, and the plates were incubated at 37° C./5% $CO_2$ for approximately 40 hours. AlamarBlue® indicator dye (11 µl/well) was added and the plates were incubated at 37° C./5% $CO_2$ for 6-8 hours. Plates were then read for the difference in absorbance at 570 nm and 600 nm. IC50 values were determined using nonlinear fit/sigmoidal dose-response/variable slope.

The results of the Ba/F3 hIL-17Rc-mGCSFR proliferation assay are provided at Table 14.

TABLE 14

Ba/F3 hIL-17Rc-mGCSFR Proliferation Assay

| mAb | IL-17A | [rhIL-17A] (pM) | IC50 (pM) |
| --- | --- | --- | --- |
| rat 16C10 | human | 100 | 20 ± 8 |
| rat 16C10 | human | 276 | 162 |
| rat 16C10 | cyno | 100 | 27 |
| chimeric 16C10 | human | 100 | 29 |
| hu 16C10 | human | 100 | 15 ± 2 |
| hu 16C10 VH N54Q/M96A | human | 100 | 13 |
| hu 16C10 | human | 100 | 27 |
| hu 16C10 | human | 276 | 149 |
| hu 16C10 | cyno | 100 | 17 |
| hu 16C10 N54Q/M96A/M100hF | human | 100 | 11 |
| rat 1D10 | human | 276 | 223 |
| rat 1D10 | cyno | 100 | 19 |
| rat 29H1 | human | 28 | ≥30 |
| rat 4H12 | human | 28 | ≥400 |
| rat 29G3 | human | 28 | ≥400 |

Example 12

Cross-Blocking of Anti-IL-17A Antibodies

Different anti-IL-17A antibodies of the invention may bind to the same epitope, epitopes that overlap, or epitopes that do not overlap, including epitopes that are sufficiently distinct that two or more antibodies can bind to one IL-17A monomer simultaneously. Antibodies that bind to portions of IL-17A critical to receptor binding will block the receptor-mediated biological activity of IL-17A. Such antibodies are referred to herein as "neutralizing antibodies." Antibodies that bind but do not block receptor binding are referred to as non-neutralizing antibodies.

When performing experiments on L-17A and anti-IL-17A antibodies it is useful to be able to determine the level of IL-17A (or anti-IL-17A) in a sample, such as by a sandwich ELISA. See, e.g., Example 6. In one format, an IL-17A ELISA involves coating the wells of a microtiter plate with a capture antibody, addition of an experimental sample possibly containing IL-17A, and binding of a detection antibody. The capture antibody and the detection antibody must be able to bind IL-17A at the same time.

A similar assay may be used to determine the level of an anti-IL-17A antibody, wherein a standard solution of IL-17A is bound to the wells coated with capture antibody, followed by addition of a an experimental sample possibly containing an anti-IL-17A antibody, and binding of a secondary detection antibody (e.g. an anti-human IgG antibody in the case of IgG humanized antibodies of the present invention). As in the IL-17A sandwich ELISA, the capture antibody cannot interfere with binding of the antibody to be assayed.

Preferred pairs of antibodies for use in the ELISA experiments outlined in this Example can be determined by performing cross-blocking experiments. In cross blocking experiments, a first antibody is coated onto the wells of a microtiter plate. A biotinylated second antibody is then mixed with IL-17A and allowed to bind, after which the mixture is added to the coated well and incubated. The biotinylated second antibody may be added at various concentrations (i.e. titrated) to ensure that in at least some samples the antibody is present at a two-fold (or greater) molar excess over homodimeric IL-17A. The plate is then washed and the presence or absence of the biotinylated second antibody bound in the well is determined by standard methods.

If the two antibodies cross-block there will be a reduction of signal (IL-17A binding) to the plate in the presence of the second anti-IL-17A antibody compared with control samples containing no second anti-IL-17A antibody (or containing an isotype control). Pairs of antibodies that do not cross-block can be used together in assays, such as sandwich ELISAs. Although the dimeric nature of IL-17A makes it possible to use pairs of cross-blocking antibodies in ELISAs in certain formats (e.g. where IL-17A is bound to the capture antibody on the plate prior to addition of the detection antibody), non-cross-blocking pairs of antibodies are generally preferable.

Several anti-1-17A antibodies of the present invention (clones 4C3, 6C3, SG9, 12E6, 16C10, 18H6, 23E12, 29H1, 30C10C, 1D10, 21B12, 29G33) were tested pairwise for cross-blocking. All pairs cross-blocked with the exception of 29G3/1D10 and 29G3/21B12, which pairs of antibodies could therefore be used in ELISAs. In addition to identifying pairs of anti-IL-17A antibodies that can be used in an ELISA, these results show that the epitope bound by antibody 29G3 is functionally or physically distinct from the epitope or epitopes bound by antibodies 1D10 and 21B12. These data also demonstrated that the epitopes for 1D10 and 21B12 overlap with, but are not identical to, the epitope for 16C10.

Such pairs of anti-IL-17A antibodies that bind to functionally distinct epitopes are useful, e.g., in validating anti-IL-17A immunohistochemistry (IHC). For example, if a tissue sample exhibits the same pattern of IL-17A expression in IHC performed with two different anti-IL-17A antibodies that bind to functionally distinct epitopes then it is even more likely that the assay is detecting IL-17A, rather than some other spurious cross-reacting protein in the tissue sample.

Such pairs of non-cross-blocking antibodies are also useful in designing ELISAs for detection of IL-17A in the presence of therapeutic anti-IL-17A antibodies e.g. in samples from patients undergoing anti-IL-17A antibody therapy, in which the presence of an excess of the therapeutic anti-IL-17A antibody would block detection by anti-IL-17A ELISA unless the ELISA antibodies were non-cross-blocking with the therapeutic antibody.

Example 13

Gene Therapy with Anti-IL-17A Antibodies

The anti-IL-17A antibodies of the invention may also be administered to a subject by gene therapy. In a gene therapy approach, the cells of a subject are transformed with nucleic acids that encode the antibodies of the invention. Subjects comprising the nucleic acids will then produce the antibody molecules (intrabodies) endogenously. For example, Alvarez et al. introduced single-chain anti-ErbB2 antibodies to subjects using a gene therapy approach. Alvarez et al. (2000) *Clinical Cancer Research* 6:3081-3087. The methods disclosed by Alvarez et at may be easily adapted for the introduction of nucleic acids encoding an anti-IL-17A antibody molecule of the present invention to a subject. In one embodiment, the antibody molecule introduced by gene therapy is a fully human, single-chain antibody.

The gene therapy approach described herein has the potential advantage that treatment need only be carried out once, or at most a limited number of times, provided that long-term gene expression is achieved. This is contrasted with antibody administration, which must be repeated periodically to maintain proper therapeutic levels in the subject, The nucleic acids may be introduced to the cells of a subject by any means known in the art. In some embodiments, the nucleic acids are introduced as part of a viral vector. Examples of viruses from which the vectors may be derived include lentiviruses, herpes viruses, adenoviruses, adeno-associated viruses (AAV), vaccinia virus, baculovirus, alphavirus, influenza virus, and other recombinant viruses with desirable cellular tropism. Various companies produce viral vectors commercially, for example Avigen, Inc. (Alameda, Calif.; AAV vectors); Cell Genesys (Foster City, Calif.; retroviral, adenoviral, TV vectors, and lentiviral vectors); Clontech (retroviral and baculoviral vectors); Genovo, Inc. (Sharon Hill, Pa.; adenoviral and AAV vectors); Genvec (adenoviral vectors); IntroGene (Leiden, Netherlands; adenoviral vectors); Molecular Medicine (retroviral, adenoviral, V, and herpes viral vectors); Norgen (adenoviral vectors); Oxford BioMedica (Oxford, United Kingdom; lentiviral vectors); and Transgene (Strasbourg, France; adenoviral, vaccinia, retroviral, and lentiviral vectors).

Methods of constructing and using viral vectors are know in the art (see, e.g., Miller et al. (1992) *BioTechniques* 7:980-990). Preferably, the viral vectors are replication defective (unable to replicate autonomously) and thus not infectious in the target cell. Preferably, the replication defective virus is a minimal virus retaining only the sequences of its genome that are necessary for encapsidating the genome to produce viral particles. Defective viruses that entirely or almost entirely lack viral genes are most preferred. Use of defective viral vectors allows for administration to cells in a specific localized area without concern that the vector can infect other cells, enabling tissue-specific targeting. See, e.g., Kanno et al. (1999) *Cancer Gen. Ther.* 6.147-154; Kaplitt et al. (1997) *J. Neurosci. Meth.* 71:125-132; and Kaplitt et al. (1994) *J. Neuro-Onc.* 19:137-142.

Adenoviruses are eukaryotic DNA viruses that can be modified to efficiently deliver a nucleic acid of the invention to a variety of cell types. Attenuated adenovirus vectors, such as the vector described by Stratford-Perricaudet et al (1992) (*J. Clin. Invest.* 90:626-630) are desirable in some instances.

Various replication defective adenovirus and minimal adenovirus vectors have been described (PCT Publication Nos. WO94/26914, WO94/28938, WO94/28152, WO94/12649, WO95/02697 and WO96/22378). The replication defective recombinant adenoviruses of the present invention can be prepared by any technique known to a person skilled in the art (see Levrero et al. (1991) *Gene* 101:195; EP 185573; Graham (1984) *EMBO J.* 3 :2917; Graham et al. (1977) *J. Gen. Virol.* 36:59).

Adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The use of AAV-derived vectors for transferring genes in vitro and in vivo has been described (see Donsante et al. (2001) *Gene Ther.* 8:1343-1346; Larson et al. (2001) *Adv. Emp. Med. Bio.* 489:45-57; PCT Publication Nos. WO91/18088 and WO93/09239; U.S. Pat. Nos. 4,797,368 and 5,139,941; ad EP 488528B1).

In another embodiment, the gene can be introduced in a retroviral vector, e.g., as described in U.S. Pat. Nos. 5,399,346, 4,650,764, 4,980,289, and 5,124,263; Mann et al. (1983) *Cell* 33:153; Markowitz et al. (1988) *J. Virol.* 62:1120; EP 453242 and EP178220. Retroviruses are integrating viruses that infect dividing cells.

Lentiviral vectors can be used as agents for the direct delivery and sustained expression of nucleic acids encoding an antibody molecule of the invention in several tissue types, including brain, retina, muscle, liver and blood. The vectors can efficiently transduce dividing and nondividing cells in these tissues, and maintain long-term expression of the antibody molecule. For a review, see Zufferey et al. (1998) *J. Virol.* 72:9873-80 and Kafri et al. (2001) *Curr. Opin. Mol. Ther.* 3:316-326. Lentiviral packaging cell lines are available and known generally in the art, facilitating the production of high-titer lentivirus vectors for gene therapy. An example is a tetracycline-inducible VSV-G pseudotyped lentivirus packaging cell line which can generate virus particles at titers greater than $10^6$ IU/ml for at least 3 to 4 days; see Kafri et al. (1999) *J. Virol.* 73: 576-584. The vector produced by the inducible cell line can be concentrated as needed for efficiently transducing nondividing cells in vitro and in vivo.

Sindbis virus is a member of the alphavirus genus that has been studied extensively since its discovery in various parts of the world beginning in 1953. Gene transduction based on alphavirus, particularly Sindbis virus, has been well-studied in vitro (see Straus et al. (994) *Microbiol Rev.* 58:491-562; Bredenbeek et al. (1993) *J. Virol.* 67; 6439-6446; Iijima et al. (1999) *Int. J. Cancer* 80:110-118; and Sawai et al. (1998) *Biochim. Biophys. Res. Comm.* 248:315-323). Many properties of alphavirus vectors make them a desirable alternative to other virus-derived vector systems being developed, including rapid engineering of expression constructs, production of high-titered stocks of infectious particles, infection of nondividing cells, and high levels of expression (Strauss et al. (1994) *Microbiol. Rev.* 58:491-562). Use of Sindbis virus for gene therapy has been described. (Wahlfors et al. (2000) *Gene. Ther.* 7:472-480 and Lundstrom (1999) *J. Recep. Sig. Transduct. Res.* 19(1-4):673-686).

In another embodiment, a vector can be introduced to cells by lipofection or with other transfection facilitating agents (peptides, polymers, etc.). Synthetic cationic lipids can be used to prepare liposomes for in vivo and in vitro transfection of a gene encoding a marker (Felgner et al. (1987) *Proc. Nat'l. Acad. Sci. USA* 84:7413-7417 and Wang et al. (1987) *Proc.*

*Nat.'l Acad. Sci. USA* 84:7851-7855). Useful lipid compounds and compositions for transfer of nucleic acids are described in PCT Publication Nos. WO 95/138863 and WO96/7823, and in U.S. Pat. No. 5,459,127.

It is also possible to introduce the vector in vivo as a naked DNA plasmid. Naked DNA vectors for gene therapy can be introduced into the desired host cells by methods known in the art, e.g., electroporation, microinjection, cell fusion, DEAE dextran, calcium phosphate precipitation, use of a gene gun, or use of a DNA vector transporter (see, e.g., Wilson et al. (1992) *J. Biol. Chem.* 267:963-967; Williams et al. (1991) *Proc. Nat'l. Acad. Sci. USA* 88:2726-2730). Receptor-mediated DNA delivery approaches can also be used (Wu et al (1988) *J. Biol. Chem.* 263:14621-14624). U.S. Pat. Nos. 5,580,859 and 5,589,466 disclose delivery of exogenous DNA sequences, free of transfection facilitating agents, in a mammal. A relatively low voltage, high efficiency in vivo DNA transfer technique, termed electrotransfer, has also been described (Vilquin et al. (2001) *Gene Ther.* 8:1097; Payen et al. (2001) *Exp. Hematol.* 29:295-300; Mir (2001) *Bioelectrochemistry* 53:1-10; PCT Publication Nos. WO99/01157, WO99/01158 and WO99/01175).

The gene therapy methods outlined herein may be carried out in vivo, or they may be performed ex vivo, in which cells are obtained from a subject, transformed with a gene therapy method in vitro, and subsequently reintroduced into the subject. See, e.g., Worgall (2005) *Pediatr. Nephrol.* 20(2):118-24.

Example 14

Cassette Mutagenesis of CDRs of Parental Antibodies

Optimization of the CDR sequences of anti-human IL-17A antibodies of the present invention (e.g. 16C10) is performed using shotgun scanning mutagenesis. Alanine scanning mutagenesis is used to determine which residues within the CDRs are most critical to IL-17A binding (see Example 19). The codon for one or more residues within one or more CDRs is replaced with an alanine codon, or an alanine codon is replace with a glycine codon, and the resulting antibody is tested for a relevant activity (e.g. IL-17A binding affinity, IC50 for receptor blocking in a competition assay, bioassay, as provided in various other Examples herein). Codon substitution may be performed by any method known in the art, including but not limited to site-directed mutagenesis (e.g. Kunkel, *Proc. Nat'l. Acad. Sci. USA* (1985) 82:488) and PCR mutagenesis. Residues crucial to IL-17A binding may also be determined by inspection of the structure of an IL-17A-antibody complex, e.g. an X-ray crystal structure. Antibody CDR residues within contact distance of IL-17A, or which are substantially buried in formation of the IL-17A-antibody complex, are candidates for further optimization.

Those residues with the greatest sensitivity to mutation are then studied further, for example by homolog scanning mutagenesis. In this embodiment, conservative amino acid substitutions with homologous amino acids are performed at the target residues to search for antibodies with superior qualities. Non-conservative mutations are also possible, albeit at the risk of disrupting IL-17A binding altogether.

Alternatively, improved antibody sequences may be generated using affinity maturation, in which selected residues in a CDR are mutated to generate all possible amino acid substitutions at that position. In another embodiment, fewer than all 20 possible natural amino acids are used as substitutions to reduce the number of potential sequences to more manageable levels, while still providing for chemical diversity at each position using a limited number of amino acids selected to be optimally diverse (e.g. representative hydrophobic, polar-uncharged, basic and acidic amino acids), as in WO2005/044853. Such affinity maturation can be performed by substitution with any number of amino acids at a position of interest, including 2, 3, 4, 5, 6, 7, 8, 9, 10, 11, 12, 13, 14, 15, 16, 17, 18, 19, 20, or even more if non-standard or modified amino acids are included.

Example 15

Cross-Reactivity with Human Tissue

The propensity of humanized anti-human IL-17 antibody hu16C10 to cross-reactivity with non-target tissues in human subjects was assessed as follows hu16C10 was preincubated with a biotinylated secondary antibody to form a pre-complex prior to exposure to tissue samples. Antibody complexes (with 20 µg/ml of antibody) were then mixed with a tissue or other sample and incubated to allow binding. Bound secondary antibodies were then detected using ABC immunoperoxidase detection (Vector Labs, Burlingame, Calif., USA). Tuson et al. (1990) *J. Histochem Cytochem.* 38(7):923-6. A sample with an unrelated human IgG1 antibody was included as a negative control.

Immunohistochemical (IHC) staining was performed with hu16C10 against several positive control target tissues including rhIL-17A protein spots on UV-resin slides (Adhesive Coated Slides, Instrumedics, Inc., St. Louis, Mo., USA), mouse liver cells infected with an adenovirus-encoding IL-17A, and human rheumatoid arthritis tissue. IHC revealed binding (+++) in all three positive controls IHC was then performed against a panel of human tissues (32 in all) to assess cross-reactivity. All these human tissue samples were mounted on UV-resin slides. Samples were obtained from three donors for each tissue. The human tissues screened were adrenal gland, bladder, cerebellum, cerebral cortex, colon, fallopian tube, cardiac muscle, kidney, liver, lung, lymph node, mammary gland, ovary, pancreas, parathyroid, pituitary gland, placenta, prostate, retina, skeletal muscle, skin, small intestine, spinal cord, spleen, stomach, testis, thymus, thyroid gland, ureter, uterus, and cervix (uterus). IHC was negative in all 32 tissues.

This lack of cross-reactivity has several potential benefits in therapeutic uses of the anti-IL-17A antibodies of the present invention, such as reducing the loss of antibody due to non-specific binding to other tissues (with consequent reduction in therapeutic effect), and reducing the likelihood of adverse effects associated with binding to undesired tissues.

Example 16

Treatment of Collagen-Induced Arthritis Using Anti-IL-17A Antibodies

Collagen-induced arthritis (CIA) is a widely accepted mouse model for rheumatoid arthritis in humans. Anti-IL-17A antibody 1D10 of the present invention (the parental rat antibody, rather than a humanized forms thereof is administered to mice expressing CIA to assess the ability of anti-IL-17A therapy to treat rheumatoid arthritis.

The procedure was as follows. On Day 0 male B10.RIII mice were immunized intradermally at the tail base with bovine type II collagen emulsified in Complete Freund's Adjuvant. On Day 21 mice were challenged intradermally with bovine type II collagen emulsified in Incomplete Freund's Adjuvant delivered at the tail base. When the first sign of severe arthritis in the immunized group occurred (post-Day 21), all remaining immunized mice were randomized to the various treatment groups. Animals were treated with either 800 µg, 200 µg, or 50 µg of anti-IL-17A antibody 1D10; 200 µg isotype control antibody; or diluent. Treatments were given subcutaneously on the first day of disease onset in the immunized mice, and then weekly four more times. Mice were sacrificed at day 35 and paws were fixed in 10% neutral-buffered formalin for tissue processing and sectioning. Paws were analyzed by a pathologist for the following histopathology parameters: reactive synovium, inflammation, pannus formation, cartilage destruction, bone erosion, and bone formation. Each parameter was graded using the following disease scale: 0=no disease; 1=minimal, 2=mild, 3=moderate, 4=severe. In addition paws were assessed using visual disease severity score (DSS), which measures swelling and redness on a scale of 0 to 3, with 0 being a normal paw, 1 being inflammation of one finger on the paw, 2 being inflammation of two fingers or the palm of that paw, and 3 being inflammation of the palm and finger(s) of the paw. Scores of 2 and 3 are referred to herein as severely or highly inflamed paws.

Figure 3C:
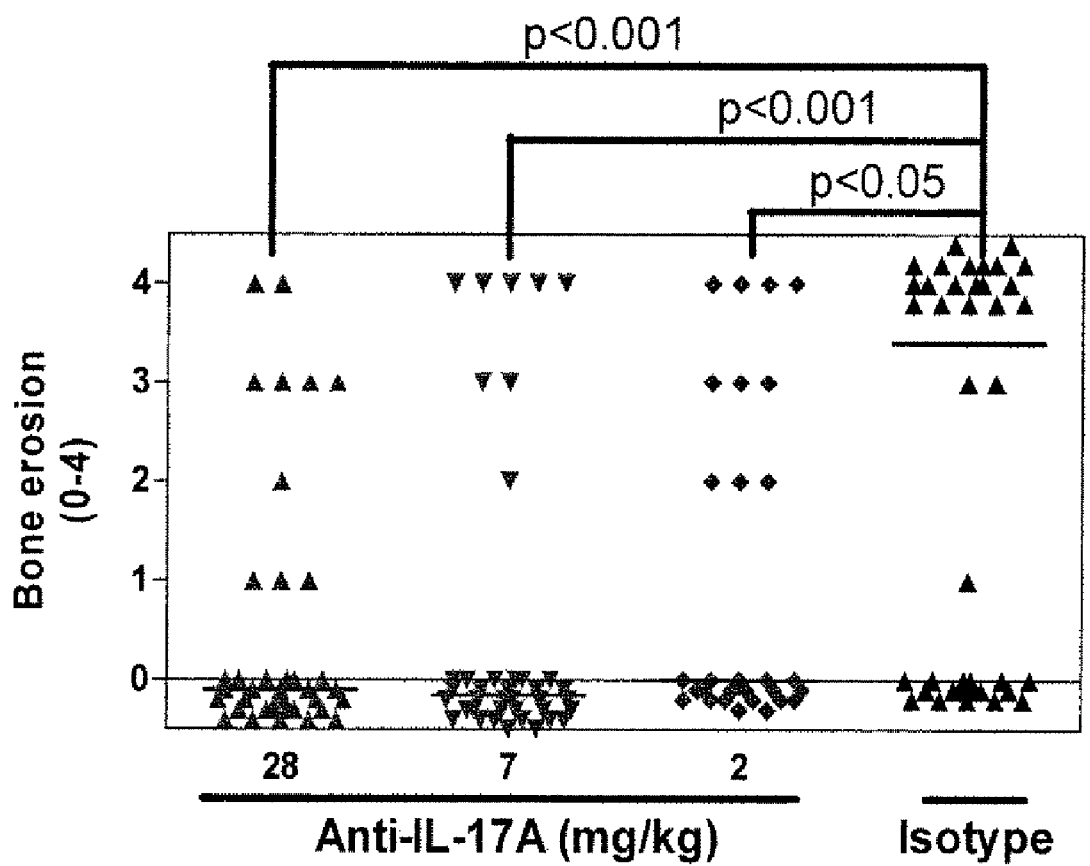

Results are presented at FIGS. 3A 3C. Each data point represents one paw, rather than an average for all four paws for an animal or an average over all animals. Reduction in the number of paws showing high pathology scores was statistically significant by three measures of pathology (visual DSS—paw swelling and redness, cartilage damage and bone erosion) with higher anti-IL-17A 1D10 concentrations tested (28 and 7 mg/kg). Results with the lowest concentration (2 mg/kg) were statistically significant for bone erosion and reduced for visual DSS and cartilage damage. Similar benefits were observed in reduction of production of cartilage degradative enzymes within inflamed paws (matrix metalloproteases MMP-2, MMP-3, MMP-13).

Figure 3D:
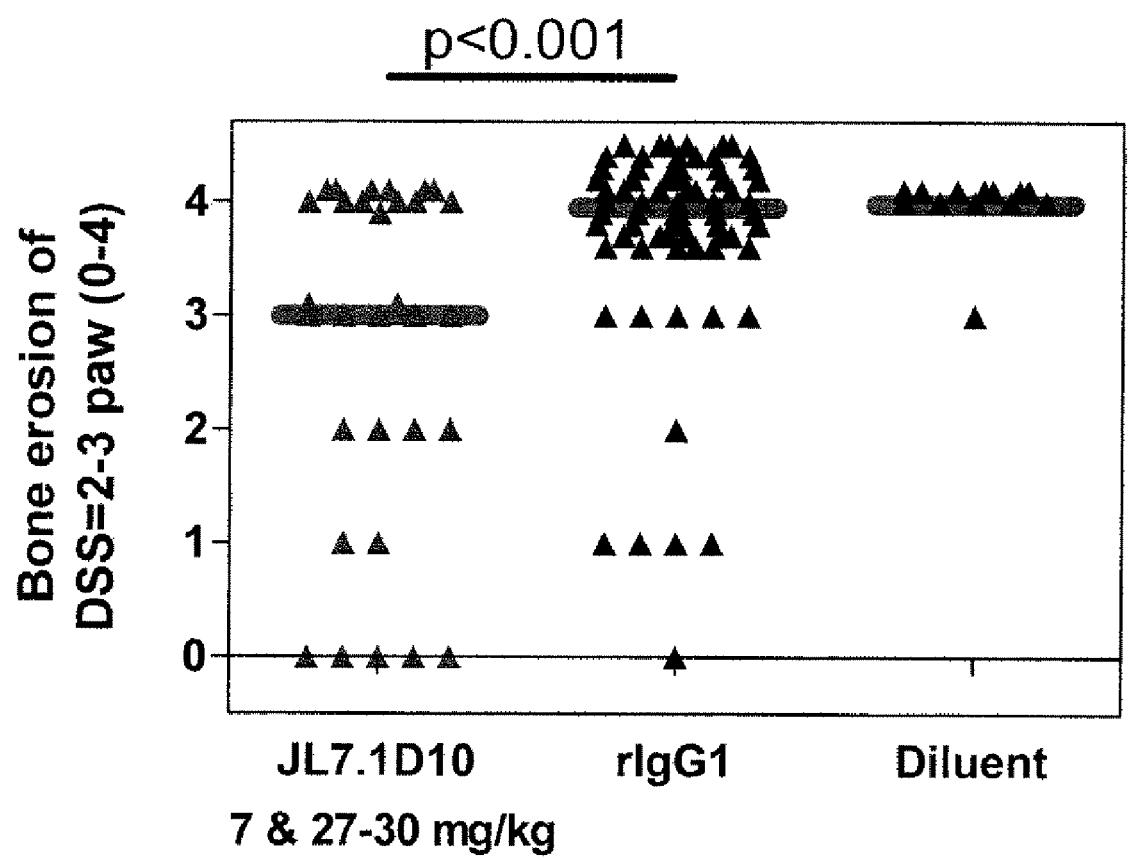

Visual evaluation of paw inflammation, however, may underestimate the therapeutic benefit of anti-IL-17A treatment of CIA mice, e.g. decreased bone erosion. In other experiments, highly inflamed paws (DSS scores of 2 or 3) from CIA mice were analyzed for bone erosion using histopathology or micro-computed tomography (micro-CT). This study was possible because even though anti-IL-17A-treated animals had drastically reduced percentages of highly inflamed paws (see, e.g., FIG. 3A), there remained a number of highly inflamed paws, and it was possible to compare highly inflamed paws (DSS 2 or 3) from all treatment groups, including the no-antibody controls. FIG. 3D shows a plot of bone erosion for highly inflamed paws from diluent treated, isotype control (rIgGI) treated, and anti-IL-17A antibody treated animals. Bone erosion, as measured by histopathology, was significantly reduced in paws from animals treated with anti-IL-17A when compared with no-antibody controls, despite their similar DSS scores. The results suggest that sparing of bone erosion may be achieved with anti-IL-17A treatment even in paws where there is no apparent improvement in inflammation as measured by DSS score.

Similar results were obtained when micro-CT was used to measure bone mineral density (BMD) for joints in highly inflamed paws in CIA mice. Table 15 provides BMD for paws with disease severity scores of 0 or 3 from CIA animals treated with either an anti-IL-17A antibody of the present invention (1D10) or an isotype control (25D2). Even for joints with the same visual disease severity, 1D10 antibody treated had only approximately half the decrease in bone mineral density observed with isotype control treated animals.

TABLE 15

Bone Density for Joints in CIA Mice

| Treatment | DSS | BMD (mg/cc) |
|---|---|---|
| 25D2 | 3 | 95 |
| 25D2 | 3 | 108 |
| 1D10 | 3 | 288 |
| 1D10 | 3 | 299 |
| 1D10 | 0 | 502 |
| 1D10 | 0 | 480 |

As with bone erosion, cartilage destruction and pannus formation (proliferation of the synovial lining forming excessive folds of inflamed tissue) were also reduced in anti-hIL-17A (1D10)-treated CIA mice. Histopathology showed that anti-IL-17A antibody treatment not only reduced the number of paws showing severe pathology, but also reduced pathology in paws that appeared equally inflamed based on visual inspection (DSS scores of 2 and 3) when compared with diluent or isotype treated controls.

The observation that treatment with anti-IL-17A antibodies significantly reduced bone erosion in the CIA model of joint inflammation suggests that such therapy may be useful in preventing one of the most debilitating and irreversible effects of RA in humans. In addition, the observation that bone erosion is reduced even in highly inflamed paws suggests that simple visual assessment of joint inflammation may not accurately measure therapeutic efficacy in the lab, or ultimately in the clinic. Measurement of bone erosion may be necessary to track the effects of therapeutic treatments. Such methods include, but are not limited to, standard 2-D X-ray detection, computed tomography (CT), magnetic resonance imaging $(MRI)_5$ ultrasound (US), and scintigraphy. See, e.g., Guermazi et al. (2004) *Semin. Musculoskelet Radiol.* 8(4): 269-285.

Example 17

BAL Neutrophil Recruitment Assay of Anti-IL-17A Antibodies

The ability of anti-IL-17A antibodies of the present invention to block the activity of IL-17A in vivo was assessed in a bronchoalveolar lavage (BAL) neutrophil recruitment assay. Briefly, at day −4, five week old female BALB/cAnN mice (Taconic Farms, Germantown, N.Y., USA) were treated with anti-IL-17A antibodies of the present invention, or an isotype control, by subcutaneous injection of 0, 10, 30, 40, 60, or 100 µg of antibody per mouse. At day −1 the mice were stimulated by nasal administration of 1 µg of rhIL-17A in 50 µl of PBS (or a PBS only control) under light isoflurane anesthesia, At day 0 the level of neutrophils present in BAL fluid was determined as follows. Mice were euthanized with $CO_2$ and blood samples were collected, from which the concentration of anti-IL-7A antibody was determined. A needle was inserted into the upper cervical trachea through a tracheotomy and BAL fluid was collected by introduction and removal of 0.3 ml of PBS three times. The BAL fluid was centrifuged (400×g for 10 minutes at 4° C.) and the cell pellet was resuspended in PBS. Total cell counts were determined in a hemocytometer using trypan blue solution. Differential cell counts were performed on cytospin preparations by Wright-Giemsa staining (Sigma-Aldrich, St. Louis, Mo., USA), according to standard morphologic criteria with use of oil immersion microscopy (original magnification×1000). Cell counts were carried out on 200 or 300 cells (lymphocytes, monocytes, neutrophils, eosinophils) to determine the percent BAL neutrophil.

Figure 4:
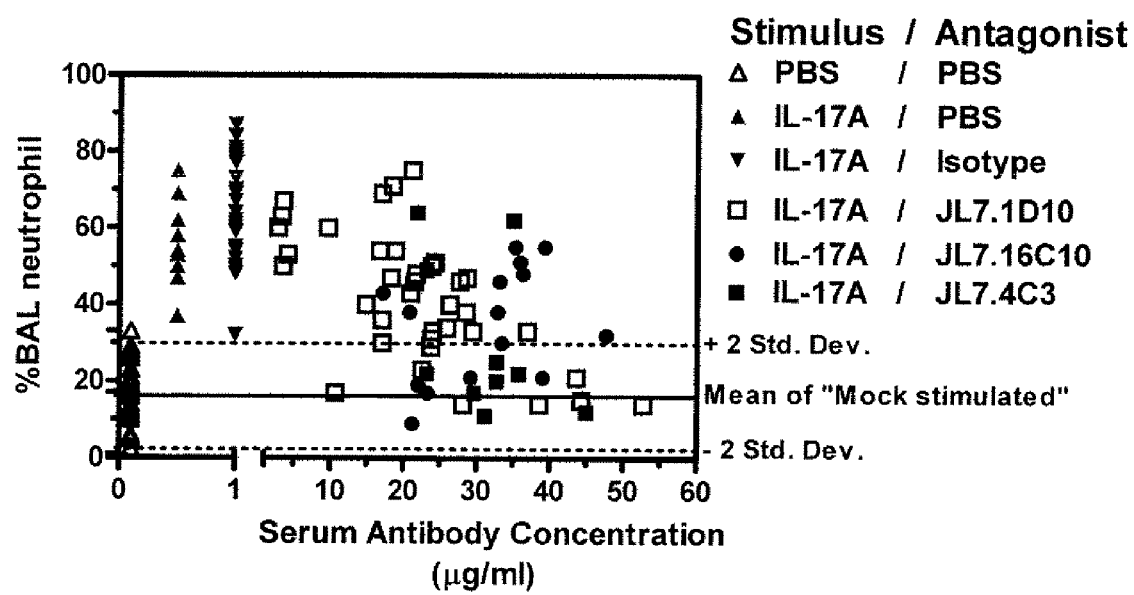
FIG. 4 presents % BAL neutrophil (a measure of neutrophil recruitment to the lung) in mice that had been treated intranasally with human IL-17A, as a function of the serum concentration of various anti-human IL-17A antibodies of the present invention (1D10, 16C10, 4C3) and an isotype control. Solid triangles represent control experiments without any added anti-IL-17A antibody, and the leftmost data points (open triangles) are unstimulated controls.

Results are provided at FIG. 4. Data are provided for three anti-IL-17A antibodies of the present invention (1D10, 16C10 and 4C3), as well as controls. The percentage of neutrophils in HAL fluid as a percentage of all leukocytes for individual experimental animals is plotted as a function of serum antibody concentration, with the left segment of the abscissa ("0" to "1") representing controls, as indicated in the legend. The controls show that rhIL-17A stimulus induces significant neutrophil recruitment that is not reduced by administration of an isotype control antibody (dosed at the same levels as the anti-IL-17A antibodies). In contrast, the anti-IL-17A data show a dose-dependent reduction in rhIL-17A-induced neutrophil recruitment, with neutrophil recruitment essentially blocked at serum antibody concentrations above 40-60 µg/ml.

Example 18

Treatment of Rheumatoid Arthritis (RA) Using Anti-IL-17A Antibodies

Human subjects diagnosed with RA who have had an inadequate response to one or more DMARDs are selected for treatment with a humanized anti-IL-17A antibody of the present invention. Subjects are maintained on methotrexate (10 mg/week), and are optionally treated with prednisone for two weeks. Subjects are also dosed monthly with 50 or 100 mg of anti-IL-17A antibody, administered subcutaneously. Doses are adjusted for specific subjects according to standard clinical criteria and on the basis of clinical response.

Response to treatment is assessed by determining the ACR score, which is based on criteria developed by the American College of Rheumatology. The ACR score is a composite score that integrates multiple clinical parameters and radiographic scores, such as reduction in the number of swollen and tender joints, patient global assessment, physician global assessment, pain scale, self-assessed disability, and acute phase reactants (erythrocyte sedimentation rate or C-reactive protein). See Felson et al. (1995) *Arthritis & Rheumatology* 38; 727-735. A subject is considered to have improved if he or she exhibits a score of ACR20 or higher at week 24 or treatment. In addition, the proportion of subjects achieving various ACR scores (e.g. ACR20, ACR50 and ACR70) can be used to compare treatment and placebo groups in clinical trials to assess the clinical efficacy of the humanized anti-IL-17A antibody of the present invention Example 19

Epitope Determination

Amino acid residues critical to binding of the antibodies of the present invention, e.g. rat 16C10, were determined a follows.

A first set of experiments was based on the observation that rat antibody 16C10 was able to bind human IL-17A (hIL-17A) but was unable to bind mouse IL17A (mIL-17A) or related cytokine human IL-17F. Each of these three proteins was linked to an N-terminal FLAG® peptide tag (see residues 1 to 9 of SEQ ID NO.: 42). In order to identify amino acid residues critical for 16C10 binding, various peptide subsequences of FLAG-tagged hIL-17A, mIL-17A and IL-17F were combined by mixing restriction fragments of the relevant genes to form hybrid polypeptides. Binding of these hybrid polypeptides to antibody 16C10 was determined in an Amplified Luminescent Proximity Homogeneous Assay (AlphaScreen, Packard BioScience, Wellesley, Mass., USA) to determine which segments of hIL-17A were critical to binding. Biotinylated antibody 16C10 was bound to streptavidin donor beads, and hybrid polypeptides were bound to acceptor beads having anti-FLAG® antibodies (Packard BioSience). Donor and acceptor beads were mixed, illuminated at 680 nm, and emission was measured at 520-620 nm. Binding was measured as enhanced fluorescence in samples containing hybrid polypeptides that bound to antibody 16C10 because acceptor beads were held in close proximity to donor beads and emitted light when singlet oxygen from the exited donor bead diffused to the acceptor bead.

The results showed that antibody 16C10 binds to hybrid polypeptides comprising amino acid residues 50-132, 63-132, 1-87, 1-112 and 63-87 from hIL-17A, demonstrating that residues critical to 16C L O binding are present in residues 63-87 of hIL-17A (PSVIWEAKCR HLGCINADG NVDYHM). All residue numbering in this example is with reference to the sequence of hIL-17A (SEQ ID NO.: 40). For example, mIL-17A and IL-17F polypeptides substituted with residues 63-87 of hIL-17A were able to bind antibody 16C10, whereas the intact mIL-17A and IL-17F were not.

Point mutations were also introduced into hIL-17A to determine which amino acid residues were critical to antibody 16C10 binding. In one experiment, alanine-scanning mutagenesis was performed in which an alanine codon was introduced in place of the native amino acid at several residues (45, 46, 51, 52, 54, 55, 56, 57, 58, 60, 61, 62, 67, 68, 70, 72, 73, 78, 80, 82, 84,85,86, 88,93,94,95, 100, 101, 102, 105, 108, 110, 111, 113, 114). Mammalian expression plasmids with genes encoding the mutant forms of hIL-17A were transiently transfected into human embryonic kidney (HEK) 293T cells. The supernatants were analyzed for FLAG® peptide tag quantification and for antibody 16C10 binding by AlphaScreen, as described supra. None of the single amino acid alamine substitutions significantly reduced binding of antibody 16C10. Other point mutations were made in which human IL-17F or mouse L-17A residues were substituted at various positions within the 63-87 fragment, i.e. L74Q, G75R, V83E, Y85H. Although none of these individual point mutations inhibited antibody 16C10C binding, an hIL-17A having all four changes exhibited substantially decreased binding, confirming that residues in the 63-87 fragment of hIL-17A, and more specifically residues in the 74-85 fragment (LGCINADGNVDY), are important for 16C10 binding.

TABLE 16

| SEQ ID NO: | Description |
|---|---|
| | Sequence Identifiers |
| 1 | hu 16C10 light chain DNA with signal sequence |
| 2 | hu 16C10 light chain amino acid with signal sequence |
| 3 | hu 16C10 heavy chain DNA with signal sequence |
| 4 | hu 16C10 heavy chain amino acid with signal sequence |
| 5 | hu 16C10/4C3 light chain variable domain |
| 6 | hu 16C10/4C3 heavy chain variable domain |
| 7 | rat 16C10 light chain variable domain |
| 8 | rat 16C10/4C3 heavy chain variable domain |
| 9 | chimeric 16C10 light chain |
| 10 | chimeric 16C10 heavy chain |
| 11 | rat/hu 16C10/4C3 CDRL1 |
| 12 | rat/hu 16C10/4C3 CDRL2 |
| 13 | rat/hu 16C10/4C3 CDRL3 |
| 14 | rat/hu 16C10/4C3 CDRH1 |
| 15 | rat 16C10/4C3 CDRH2 |

TABLE 16-continued

Sequence Identifiers

| SEQ ID NO: | Description |
| --- | --- |
| 16 | hu 16C10/4C3 CDRH2 (N54Q) |
| 17 | rat 16C10 CDRH2 (N54N/Q/A) |
| 18 | rat 16C10/4C3 CDRH3 |
| 19 | hu 16C10/4C3 CDRH3 (M96A) |
| 20 | rat 16C10 CDRH3 (M96M/A/K, M100hM/F) |
| 21 | rat 4C3 light chain variable domain |
| 22 | hu 30C10 light chain variable domain |
| 23 | hu 30C10 heavy chain variable domain |
| 24 | rat 30C10 light chain variable domain |
| 25 | rat 30C10 heavy chain variable domain |
| 26 | rat/hu 30C10 CDRL1 |
| 27 | rat/hu 30C10 CDRL2 |
| 28 | rat/hu 30C10 CDRL3 |
| 29 | rat/hu 30C10 CDRH1 |
| 30 | rat/hu 30C10 CDRH2 |
| 31 | rat/hu 30C10 CDRH3 |
| 32 | rat 12E6 light chain variable domain |
| 33 | rat 12E6 heavy chain variable domain |
| 34 | rat/hu 12E6 CDRL1 |
| 35 | rat/hu 12E6 CDRL2 |
| 36 | rat/hu 12E6 CDRL3 |
| 37 | rat/hu 12E6 CDRH1 |
| 38 | rat/hu 12E6 CDRH2 |
| 39 | rat/hu 12E6 CDRH3 |
| 40 | huIL-17A (native) |
| 41 | rhIL-17A |
| 42 | FLAG-IL-17A |
| 43 | R&D IL-17A |
| 44 | rat 23E12 light chain variable domain DNA with signal sequence |
| 45 | rat 23E12 light chain variable domain amino acid with signal sequence |
| 46 | rat 23E12 heavy chain variable domain DNA with signal sequence |
| 47 | rat 23E12 heavy chain variable domain amino acid with signal sequence |
| 48 | rat/hu 23E12 CDRL1 |
| 49 | rat/hu 23E12 CDRL2 |
| 50 | rat/hu 23E12 CDRL3 |
| 51 | rat/hu 23E12 CDRH1 |
| 52 | rat/hu 23E12 CDRH2 |
| 53 | rat/hu 23E12 CDRH3 |
| 54 | rat 1D10 light chain variable domain |
| 55 | rat 1D10 heavy chain variable domain |
| 56 | rat 1D10 CDRL1 |
| 57 | rat 1D10 CDRL2 |
| 58 | rat 1D10 CDRL3 |
| 59 | rat 1D10 CDRH1 |
| 60 | rat 1D10 CDRH2 |
| 61 | rat 1D10 CDRH3 |
| 62 | hu 16C10 light chain DNA with signal sequence |
| 63 | hu 16C10 heavy chain DNA with signal sequence |

Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

What is claimed is:

1. An isolated binding compound that binds to human IL-17A, comprising:
   at least one antibody light chain variable region and
   at least one antibody heavy chain variable region,
   wherein the light chain variable region comprises the CDR sequences of SEQ ID NOs: 11, 12 and 13; and
   wherein the heavy chain variable region comprises the CDR sequences of SEQ ID NOs: 14, 17 and 20.

2. The binding compound of claim 1, wherein the heavy chain variable region comprises the CDR sequences of SEQ ID NOs: 14, 16 and 19.

3. The binding compound of claim 2, wherein the light chain variable region comprises the sequence of SEQ ID NO:5 having the CDR sequences of SEQ ID NOs: 11, 12 and 13 and up to ten conservative amino acid substitutions in the framework residues and wherein the heavy chain variable region comprises the sequence of SEQ ID NO:6 having the CDR sequences of SEQ ID NOs: 14, 16 and 19 and up to ten conservative amino acid substitutions in the framework residues.

4. The binding compound of claim 1, wherein the binding compound is an antibody comprising:
   a light chain variable region that comprises SEQ ID NO: 5; and
   a heavy chain variable region that comprises SEQ ID NO: 6.

5. The binding compound of claim 1, wherein the light chain consists essentially of amino acids 1-220 of SEQ ID NO:2 having the CDR sequences of SEQ ID NOs: 11, 12 and 13 and up to ten conservative amino acid substitutions in the constant region.

6. The binding compound of claim 4, wherein the light chain consists essentially of amino acids 1-220 of SEQ ID NO: 2 and the heavy chain consists essentially of amino acids 1-454 of SEQ ID NO: 4.

7. The binding compound of claim 6, wherein the light chain consists of amino acids 1-220 of SEQ ID NO: 2 and the heavy chain consists of amino acids 1-454 of SEQ ID NO: 4.

8. An isolated binding compound that binds to human IL-17A, wherein the binding compound comprises:
   an antibody light chain having the CDR sequences of SEQ ID NOs: 11, 12 and 13 and at least 95% sequence identity with amino acids 1-220 of SEQ ID NO: 2; and
   an antibody heavy chain having the CDR sequences of SEQ ID NOs: 14, 16 and 19 and at least 95% sequence identity with amino acids 1-454 of SEQ ID NO: 4.

9. An isolated anti-human IL-17A antibody hu16C10, wherein the amino acid sequence of the antibody is encoded by the expression vector having ATCC Accession No. PTA-7675.

10. The binding compound of claim 1, wherein the binding compound is a humanized or fully-human monoclonal antibody.

11. A composition comprising:
    a binding compound that binds to human IL-17A and neutralizes human IL-17A activity, wherein the binding compound comprises an antibody light chain variable region and an antibody heavy chain variable region, wherein the light chain variable region comprises SEQ ID NO: 5 and the heavy chain variable region comprises SEQ ID NO: 6; and
    a pharmaceutically acceptable carrier or diluent.

12. The composition of claim 11, further comprising another immunosuppressive or anti-inflammatory agent.

13. The binding compound of claim 2, further comprising a heavy chain constant region, wherein the heavy chain constant region comprises a γ1, γ2, γ3, or γ4 human heavy chain constant region.

14. The binding compound of claim 13, wherein the heavy chain constant region comprises a γ1 human heavy chain constant region.

15. The binding compound of claim 13, wherein the heavy chain constant region comprises a γ4 human heavy chain constant region.

16. The binding compound of claim 2, further comprising a light chain constant region, wherein the light chain constant region comprises a kappa human light chain constant region.

17. The binding compound of claim 2, wherein the binding compound is an antibody fragment selected from the group consisting of Fab, Fab', Fab'-SH, Fv, scFv, F(ab')$_2$, and a diabody.

18. The binding compound of claim 3, wherein the binding compound is an antibody fragment selected from the group consisting of Fab, Fab', Fab'-SH, Fv, scFv, F(ab')$_2$, and a diabody.

19. The binding compound of any of claim 1 or 8, wherein the binding compound inhibits human IL-17A activity.

* * * * *